United States Patent
Sugihara

(10) Patent No.: US 10,724,046 B2
(45) Date of Patent: Jul. 28, 2020

(54) METHOD OF PRODUCING LIPID

(71) Applicant: KAO CORPORATION, Chuo-ku, Tokyo (JP)

(72) Inventor: Shinji Sugihara, Wakayama (JP)

(73) Assignee: Kao Corporation, Tokyo (JP)

( * ) Notice: Subject to any disclaimer, the term of this patent is extended or adjusted under 35 U.S.C. 154(b) by 96 days.

(21) Appl. No.: 15/755,240

(22) PCT Filed: Sep. 1, 2016

(86) PCT No.: PCT/JP2016/075722
§ 371 (c)(1),
(2) Date: Feb. 26, 2018

(87) PCT Pub. No.: WO2017/043418
PCT Pub. Date: Mar. 16, 2017

(65) Prior Publication Data
US 2018/0223299 A1 Aug. 9, 2018

(30) Foreign Application Priority Data
Sep. 11, 2015 (JP) .................. 2015-179166

(51) Int. Cl.
| C12N 9/16 | (2006.01) |
| C12N 15/82 | (2006.01) |
| C12P 7/64 | (2006.01) |
| C07K 14/405 | (2006.01) |
| C12N 9/10 | (2006.01) |

(52) U.S. Cl.
CPC ........ *C12N 15/8247* (2013.01); *C07K 14/405* (2013.01); *C12N 9/1029* (2013.01); *C12N 9/16* (2013.01); *C12P 7/64* (2013.01); *C12P 7/6409* (2013.01); *C12P 7/6436* (2013.01); *C12Y 203/01041* (2013.01); *C12Y 301/02014* (2013.01)

(58) Field of Classification Search
None
See application file for complete search history.

(56) References Cited

U.S. PATENT DOCUMENTS

| 5,512,482 A | 4/1996 | Voelker et al. |
| 2006/0168684 A1 | 7/2006 | Renz et al. |
| 2009/0083882 A1 | 3/2009 | Zank et al. |
| 2009/0298143 A1 | 12/2009 | Roessler et al. |
| 2013/0149754 A1 | 6/2013 | Dulermo et al. |
| 2015/0307860 A1 | 10/2015 | Ozaki et al. |
| 2017/0044580 A1 | 2/2017 | Sugihara et al. |

FOREIGN PATENT DOCUMENTS

| JP | 7-501924 A | 3/1995 |
| JP | 2011-505838 A | 3/2011 |
| JP | 2014-511140 A | 5/2014 |
| WO | WO 92/20236 A | 11/1992 |
| WO | WO 01/21820 A1 | 3/2001 |
| WO | WO 2009/076559 A1 | 6/2009 |
| WO | WO 2012/106560 A9 | 8/2012 |
| WO | WO 2014/058295 A1 | 4/2014 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

International Search Report (ISR) for PCT/JP2016/075722; I.A. fd Sep. 1, 2016, dated Nov. 15, 2016 from the Japan Patent Office, Tokyo, Japan.

International Preliminary Report on Patentability (IPRP), Chapter I of the Patent Cooperation Treaty, including the Written Opinion for PCT/JP2016/075722; I.A. fd Sep. 1, 2016, dated Mar. 13, 2018, by the International Bureau of WIPO, Geneva, Switzerland.

Yao, Y. et al., "Glycerol and neutral lipid production in the oleaginous marine diatom *Phaeodactylum tricornutum* promoted by overexpression of glycerol-3-phosphate dehydrogenase," Biotechnology for Biofuels, 2014, 7:110, doi.org/10.1186/1754-6834-7-110, Published: Jul. 21, 2014, BioMed Central Ltd., London, England.

Vigeolas, H. et al., "Increasing seed oil content in oil-seed rape (*Brassica napus* L.) by over-expression of a yeast glycerol-3-phosphate dehydrogenase under the control of a seed-specific promoter," Plant Biotechnol J. May 2007;5(3):431-41, Oxford Wiley, Oxford, England.

Database GenBank[online], 2014, [retrieval date Oct. 21, 2016], (excerpted) Nannochloropsis gaditana strain B-31 contig00217, whole genome shotgun sequence, locus_tag=Naga=100217g6, protein_id=EWM24210.1, 3 pages.

Database GenBank[online], 2014, [retrieval date Oct. 21, 2016], (excerpted) Nannochloropsis gaditana strain B-31 contig00002, Whole genome shotgun sequence, locus_tag:Naga_100002g173, protein_id=EWM28742.1, 4 pages.

* cited by examiner

*Primary Examiner* — Richard G Hutson
(74) *Attorney, Agent, or Firm* — Sterne, Kessler, Goldstein & Fox P.L.L.C.

(57) ABSTRACT

A method of improving lipid productivity, containing the steps of:

enhancing the expression of a gene encoding the following protein (A) or (B), and improving the productivity of medium-chain fatty acids or lipids containing these fatty acids as components produced in a cell of a transformant, or the total amount of all fatty acids produced in a cell of a transformant:

(A) a protein consisting of the amino acid sequence set forth in SEQ ID NO: 1; and (B) a protein consisting of an amino acid sequence having 64% or more identity with the amino acid sequence of the protein (A), and having glycerol-3-phosphate dehydrogenase activity.

10 Claims, No Drawings

Specification includes a Sequence Listing.

US 10,724,046 B2

METHOD OF PRODUCING LIPID

TECHNICAL FIELD

The present invention relates to a method of producing lipids. Further, the present invention also relates to a glycerol-3-phosphate dehydrogenase, a gene encoding the same, and a transformant wherein the expression of the gene is enhanced, for use in this method.

BACKGROUND ART

Fatty acids are one of the principal components of lipids. In vivo, fatty acids are bonded to glycerin via an ester bond to form lipids (fats and oils) such as triacylglycerol. Further, many animals and plants also store and utilize fatty acids as an energy source. These fatty acids and lipids stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts, alkyl benzene sulfonic acid salts and the like are utilized as anionic surfactants. Further, polyoxyalkylene alkyl ethers, alkyl polyglycosides and the like are utilized as nonionic surfactants. These surfactants are used for detergents, disinfectants, or the like. Cationic surfactants such as alkylamine salts and mono- or dialkyl-quaternary amine salts, as other higher alcohol derivatives, are commonly used for fiber treatment agents, hair conditioning agents, disinfectants, or the like. Further, benzalkonium type quaternary ammonium salts are commonly used for disinfectants, antiseptics, or the like. Furthermore, lipids derived from plants are also used as raw materials of biodiesel fuels.

Fatty acids and lipids are widely used for various applications shown above, and therefore, it has been attempted to enhance the productivity of fatty acids or lipids in vivo by using plants and the like. Furthermore, the applications and usefulness of fatty acids depend on the number of carbon atoms. Therefore, controlling of the number of carbon atoms of the fatty acids, namely, a chain length thereof has also been attempted.

A fatty acid synthetic pathway of plants is localized in the chloroplast. In the chloroplast, an elongation reaction of the carbon chain is repeated starting from an acetyl-ACP (acyl-carrier-protein), and finally an acyl-ACP (a composite consisting of an acyl group being a fatty acid residue and an ACP) having 16 or 18 carbon atoms is synthesized. The synthesized acyl-ACP is formed into a free fatty acid by an acyl-ACP thioesterase (hereinafter, also simply referred to as "TE"). To the free fatty acid, CoA is bonded by an acyl-CoA synthetase. Then, the fatty acid acyl-CoA is incorporated into a glycerol skeleton by various acyltransferases, and is accumulated as triacylglycerol.

It is known that a glycerol-3-phosphate dehydrogenase (hereinafter, also simply referred to as "G3PDH") plays a role of catalyzing a reaction of reducing dihydroxyacetone phosphate (DHAP) into glycerol-3-phosphate in a lipid synthesis to provide the glycerol skeleton. Thus, in order to cause accumulation of glycerolipids in plants or yeast, enhancement of expression of the G3PDH or modification of the G3PDH per se is proposed (see Patent Literatures 1 to 3 and Non-Patent Literature 1). Moreover, it is reported that an amount of lipids is increased by enhancing the expression of the G3PDH also in algae (see Non-Patent Literature 2).

Recently, algae attract attention due to its usefulness in biofuel production. The algae can produce lipids that can be used as the biodiesel fuels through photosynthesis, and do not compete with foods. Therefore, the algae attract attention as next-generation biomass resources. Moreover, it is also reported that the algae have higher lipid productivity and accumulation ability in comparison with plants. Research has started on a lipid synthesis and accumulation mechanism of the algae and lipid production technologies utilizing the mechanism, but unclear parts remain in many respects.

CITATION LIST

Patent Literatures

Patent Literature 1: US 2006/0168684
Patent Literature 2: WO 01/21820
Patent Literature 3: US 2013/0149754

Non-Patent Literatures

Non-Patent Literature 1: Vigeolas H. et al., Plant Biotechnology Journal, 2007, vol. 5, p. 431-441
Non-Patent Literature 2: Yao Y. et al., Biotechnology for Biofuels, 2014, vol. 7 (110)

SUMMARY OF INVENTION

The present invention relates to a method of producing lipids, containing the steps of:
culturing a transformant wherein the expression of a gene encoding the following protein (A) or (B) is enhanced, and producing fatty acids or lipids containing these fatty acids as components:
(A) a protein consisting of the amino acid sequence set forth in SEQ ID NO: 1; and
(B) a protein consisting of an amino acid sequence having 64% or more identity with the amino acid sequence of the protein (A), and having glycerol-3-phosphate dehydrogenase activity.

Further, the present invention is a method of improving lipid productivity, containing the steps of:
enhancing the expression of a gene encoding the protein (A) or (B) in a transformant, and
improving the productivity of medium-chain fatty acids or lipids containing these fatty acids as components produced in a cell of the transformant.

Further, the present invention is a method of improving lipid productivity, containing the steps of:
enhancing the expression of a gene encoding the protein (A) or (B) in a transformant, and
improving the total amount of the fatty acids, produced in a cell of the transformant.

Further, the present invention is a method of modifying the composition of lipids, containing the steps of:
enhancing the expression of a gene encoding the protein (A) or (B) in a transformant, and
improving the productivity of medium-chain fatty acids or lipids containing these fatty acids as components produced in a cell of the transformant, to modify the composition of fatty acids or lipids in all fatty acids or all lipids to be produced.

The present invention relates to the protein (A) or (B).
Further, the present invention relates to a gene encoding the protein (A) or (B).
Furthermore, the present invention relates to a transformant, wherein the expression of a gene encoding the protein (A) or (B) is enhanced.

MODE FOR CARRYING OUT THE INVENTION

The present invention relates to a method of producing lipids, which improves productivity of medium-chain fatty acids or the lipids containing these fatty acids as components, and total amount of the lipids to be produced.

Further, the present invention relates to a transformant in which the productivity of medium-chain fatty acids or the lipids containing these fatty acids as components and total amount of the lipids to be produced are improved.

The present inventors newly identified, as an enzyme involved in a fatty acid synthesis, a G3PDH of algae of the genus *Nannochloropsis*, being one kind of algae. Then, the present inventor enhanced expression of the G3PDH in microorganisms, and as the result, found that the productivity of medium-chain fatty acids or the lipids containing these fatty acids as components to be produced and total amount of the lipids to be produced are significantly improved.

The present invention was completed based on these findings.

According to the method of producing the lipids of the present invention, the productivity of medium-chain fatty acids or the lipids containing these fatty acids as components and total amount of the lipids to be produced can be improved.

Moreover, the transformant of the present invention is excellent in the productivities of medium-chain fatty acids or the lipids containing these fatty acids as components and total amount of the lipids to be produced.

Other and further features and advantages of the invention will appear more fully from the following description.

The term "lipid(s)" in the present specification, covers a simple lipid such as a neutral lipid (triacylglycerol, or the like), wax, and a ceramide; a complex lipid such as a phospholipid, a glycolipid, and a sulfolipid; and a derived lipid obtained from the lipid such as a fatty acid, alcohols, and hydrocarbons.

In the present specification, the description of "Cx:y" for the fatty acid or the acyl group constituting the fatty acid means that the number of carbon atoms is "x" and the number of double bonds is "y". The description of "Cx" means a fatty acid or an acyl group having "x" as the number of carbon atoms.

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in this description, the "stringent conditions" includes, for example, the method described in Molecular Cloning—A LABORATORY MANUAL THIRD EDITION [Joseph Sambrook and David W. Russell, Cold Spring Harbor Laboratory Press], and examples thereof include conditions where hybridization is performed by incubating a solution containing 6×SSC (composition of 1×SSC: 0.15 M sodium chloride, 0.015 M sodium citrate, pH 7.0), 0.5% SDS, 5×Denhardt's solution and 100 mg/mL herring sperm DNA together with a probe at 65° C. for 8 to 16 hours.

Furthermore, in the present specification, the term "upstream" of a gene means a region subsequent to a 5' side of a targeted gene or region, and not a position from a translational initiation site. On the other hand, the term "downstream" of the gene means a region subsequent to a 3' side of the targeted gene or region.

The above-described protein (A) or (B) (hereinafter, also referred to as "NoG3PDH") is one of the oxidation-reduction enzyme, and the protein which catalyzes the reductive reaction from dihydroxyacetone phosphate to glycerol-3-phosphate. The protein consisting of the amino acid sequence set forth in SEQ ID NO: 1 is one of the G3PDH derived from *Nannochloropsis oculata* NIES-2145 being algae belonged to the genus *Nannochloropsis*.

Both proteins (A) and (B) described above have the glycerol-3-phosphate dehydrogenase activity (hereinafter, also referred to as "G3PDH activity"). In the present specification, the term "G3PDH activity" means the activity to catalyze the reductive reaction from dihydroxyacetone phosphate to glycerol-3-phosphate.

The G3PDH activity of the protein can be confirmed by, for example, introducing a DNA produced by linking a gene encoding the protein to the downstream of a promoter which functions in a host cell, into a host cell, culturing the thus-obtained cell under the conditions suitable for the expression of the introduced gene, and analyzing any change of the content of glycerol-3-phosphate (hereinafter, also referred to as "G3P") caused thereby in the host cell by an ordinary technique. Alternatively, the G3PDH activity can be confirmed by introducing a DNA produced by linking a gene encoding the protein to the downstream of a promoter which functions in a host cell, into a host cell, culturing the thus-obtained cell under the conditions suitable for the expression of the introduced gene, and subjecting a disruption liquid of the cell to a G3P synthesis reaction using dihydroxyacetone phosphate and NADH.

By the results of Blast analysis using the amino acid sequence and nucleotide sequence, the proteins (A) and (B) were determined to be the G3PDH. In addition, in *Nannochloropsis oculata* NIES-2145 strain into which the gene encoding the protein (A) or (B) was introduced, it was also confirmed that the content of G3P was significantly improved in comparison with the wild type strain.

As shown in Examples mentioned later, the productivity of medium-chain fatty acids having 12, 14 or the like carbon atoms and total amount of all fatty acids to be produced are improved in the transformant, wherein the expression of the gene encoding the protein (A) is enhanced.

In addition, in the present specification, the term "medium-chain" means that the number of carbon atoms of the acyl group is 6 or more and 14 or less, preferably 8 or more and 14 or less, more preferably 10 or more and 14 or less, more preferably 12 or more and 14 or less, and furthermore preferably 12 or 14.

In the protein (B), the identity with the amino acid sequence of the protein (A) is preferably 65% or more, preferably 70% or more, more preferably 75% or more, further preferably 80% or more, further preferably 83% or more, further preferably 85% or more, further preferably 87% or more, further preferably 90% or more, further preferably 93% or more, further preferably 95% or more, further preferably 97% or more, further preferably 98% or more, and furthermore preferably 99% or more, in view of G3PDH activity. Further, specific examples of the protein (B) include a protein in which 1 or several, for example 1 or more and 167 or less, preferably 1 or more and 162 or less, more preferably 1 or more and 139 or less, further preferably 1 or more and 116 or less, furthermore preferably 1 or more and 93 or less, furthermore preferably 1 or more and 69 or less, furthermore preferably 1 or more and 60 or less, furthermore preferably 1 or more and 46 or less, furthermore preferably 1 or more and 32 or less, furthermore preferably 1 or more and 23 or less, furthermore preferably 1 or more and 13 or less, furthermore preferably 1 or more and 9 or less, and furthermore preferably 1 or more and 4 or less, amino acids are deleted, substituted, inserted or added to the amino acid sequence of the protein (A).

A method of introducing the mutation into an amino acid sequence includes a method of, for example, introducing a mutation into a nucleotide sequence encoding the amino acid sequence. A method of introducing the mutation includes a method of introducing a site-specific mutation. Specific examples of the method of introducing the site-specific mutation include a method of utilizing the SOE-PCR, the ODA method, and the Kunkel method. Further, commercially available kits such as Site-Directed Mutagenesis System Mutan-Super Express Km kit (Takara Bio), Transformer TM Site-Directed Mutagenesis kit (Clontech Laboratories), and KOD-Plus-Mutagenesis Kit (TOYOBO) can also be utilized. Furthermore, a gene containing a desired mutation can also be obtained by introducing a genetic mutation at random, and then performing an evaluation of the enzyme activities and a gene analysis thereof by an appropriate method.

The proteins (A) and (B) can be obtained by chemical techniques, genetic engineering techniques or the like that are ordinarily carried out. For example, a natural product-derived protein can be obtained through isolation, purification and the like from *Nannochloropsis oculata*. In addition, the proteins (A) and (B) can be obtained by artificial chemical synthesis based on the amino acid sequence set forth in SEQ ID NO: 1. Alternatively, as recombinant proteins, proteins (A) and (B) may also be produced by gene recombination technologies. In the case of producing a recombinant protein, the G3PDH gene described below can be used.

Note that the algae such as *Nannochloropsis oculata* can be obtained from culture collection such as private or public research institutes or the like. For example, *Nannochloropsis oculata* NIES-2145 can be obtained from National Institute for Environmental Studies (NIES).

An example of the gene encoding the protein (A) or (B) (hereinafter, also referred to as "G3PDH gene") includes a gene consisting of the following DNA (a) or (b) (hereinafter, also referred to as "NoG3PDH gene").
(a) a DNA consisting of the nucleotide sequence set forth in SEQ ID NO: 2; and
(b) a DNA consisting of a nucleotide sequence having 59% or more identity with the nucleotide sequence of the DNA (a), and encoding a protein having G3PDH activity.

The nucleotide sequence set forth in SEQ ID NO: 2 is a nucleotide sequence of a gene encoding a protein (G3PDH derived from *Nannochloropsis oculata* NIES-2145) consisting of the amino acid sequence set forth in SEQ ID NO: 1.

In the DNA (b), the identity with the nucleotide sequence of the DNA (a) is preferably 60% or more, preferably 65% or more, preferably 70% or more, more preferably 75% or more, further preferably 80% or more, further preferably 83% or more, further preferably 87% or more, further preferably 90% or more, further preferably 93% or more, further preferably 95% or more, further preferably 97% or more, further preferably 98% or more, and furthermore preferably 99% or more, in view of G3PDH activity. Further, the DNA (b) is also preferably a DNA in which 1 or several, for example 1 or more and 573 or less, preferably 1 or more and 559 or less, more preferably 1 or more and 489 or less, further preferably 1 or more and 419 or less, furthermore preferably 1 or more and 349 or less, furthermore preferably 1 or more and 279 or less, furthermore preferably 1 or more and 209 or less, furthermore preferably 1 or more and 181 or less, furthermore preferably 1 or more and 139 or less, furthermore preferably 1 or more and 97 or less, furthermore preferably 1 or more and 69 or less, furthermore preferably 1 or more and 41 or less, furthermore preferably 1 or more and 27 or less, and furthermore preferably 1 or more and 13 or less nucleotides are deleted, substituted, inserted or added to the nucleotide sequence set forth in SEQ ID NO: 2, and encoding a protein having G3PDH activity.

Furthermore, the DNA (b) is also preferably a DNA capable of hybridizing with a DNA consisting of a nucleotide sequence complementary with the DNA (a) under a stringent condition, and encoding the protein having G3PDH activity.

A method of enhancing the expression of the G3PDH gene can be appropriately selected from an ordinarily method. For example, a method of introducing the G3PDH gene into a host, or a method of modifying expression regulation regions of the gene (promoter, terminator, or the like) in a host having the G3PDH gene on a genome, can be selected.

Note that, in the present specification, a cell in which expression of a gene encoding a target protein herein is enhanced is also referred to as the "transformant", and a cell in which the expression of the gene encoding the target protein is not enhanced is also referred to as the "host" or "wild type strain".

In the transformant used in the present invention, the productivity of medium-chain fatty acids and lipids containing these medium-chain fatty acids as components (a production amount of medium-chain fatty acids or lipids containing these medium-chain fatty acids as components, or a ratio of medium-chain fatty acids or lipids containing these medium-chain fatty acids as components in the total fatty acids or total lipids to be produced) is significantly improved, in comparison with a host or wild type strain. Moreover, as a result, in the transformant, the fatty acid composition in the lipid is modified. Therefore, the present invention using the transformant can be preferably applied to production of lipids having specific number of carbon atoms, particularly medium-chain fatty acids or lipids containing these medium-chain fatty acids as components, preferably fatty acids having 6 to 14 carbon atoms or lipids containing these fatty acids as components, more preferably fatty acids having 8 to 14 carbon atoms or lipids containing these fatty acids as components, further preferably fatty acids having 10 to 14 carbon atoms or lipids containing these fatty acids as components, further preferably fatty acids having 12 to 14 carbon atoms or lipids containing these fatty acids as components, further preferably fatty acids having 12 or 14 carbon atoms or lipids containing these fatty acids as components, and furthermore preferably saturated fatty acids having 12 or 14 carbon atoms (lauric acid or myristic acid) or lipids containing these fatty acids as components.

Moreover, in the transformant used in the present invention, the productivity of medium-chain fatty acids or lipids containing these fatty acids as components as well as a total amount of all fatty acids to be produced are significantly improved, in comparison with a host. Therefore, the present invention using the transformant can be preferably applied to production of lipids.

The productivity of fatty acids and lipids of the host and the transformant can be measured by the method used in Examples described below.

The method of introducing the G3PDH gene into a host and enhancing the expression of the gene is described.

The G3PDH gene can be obtained by genetic engineering techniques that are ordinarily carried out. For example, the G3PDH gene can be artificially synthesized based on the amino acid sequence set forth in SEQ ID NO: 1 or the nucleotide sequence set forth in SEQ ID NO: 2. The synthesis of the G3PDH gene can be achieved by utilizing, for example, the services of Invitrogen. Further, the gene can also be obtained by cloning from *Nannochloropsis oculata*. The cloning can be carried out by, for example, the methods described in Molecular Cloning: A LABORATORY MANUAL THIRD EDITION [Joseph Sambrook, David W. Russell, Cold Spring Harbor Laboratory Press (2001)]. Furthermore, *Nannochloropsis oculata* NIES-2145 used in Examples can be obtained from National Institute for Environmental Studies (NIES).

The transformant that can be preferably used in the present invention is obtained by introducing the G3PDH gene into a host according to an ordinarily method. Specifically, the transformant can be produced by preparing a recombinant vector or a gene expression cassette which is capable of expressing the G3PDH gene in a host cell, introducing this vector or cassette into host cell, and thereby transforming the host cell.

The host for the transformant can be appropriately selected from ordinarily used hosts. For example, microorganisms (including algae and microalgae), plants or animals can be used as the host in the present invention. Among these, microorganisms or plants are preferable, microorganisms are more preferable, and microalgae are further preferable as a host, from the viewpoints of production efficiency and the usability of lipids to be obtained.

As the microorganisms, prokaryotes and eukaryotes can be used. Examples of the prokaryotes include microorganisms belonging to the genus *Escherichia*, microorganisms belonging to the genus *Bacillus*, microorganisms belonging to the genus *Synechocystis*, microorganisms belonging to the genus *Synechococcus*, and the like. Examples of the eukaryotes include eukaryotic microorganisms belonging to yeast, filamentous fungi and the like. Among these, from a viewpoint of the lipid productivity, *Escherichia coli*, *Bacillus subtilis*, *Rhodosporidium toruloides*, or *Mortierella* sp., is preferable, and *Escherichia coli* is more preferable.

As the algae or microalgae, from a viewpoint of establishment of a gene recombination technique, algae belonging to the genus *Chlamydomonas*, algae belonging to the genus *Chlorella*, algae belonging to the genus *Phaeodactylum*, or algae belonging to the genus *Nannochloropsis* are preferable, and algae belonging to the genus *Nannochloropsis* are more preferable. Specific examples of the algae belonging to the genus *Nannochloropsis* include *Nannochloropsis oculata*, *Nannochloropsis gaditana*, *Nannochloropsis salina*, *Nannochloropsis oceanica*, *Nannochloropsis atomus*, *Nannochloropsis maculata*, *Nannochloropsis granulata*, and *Nannochloropsis* sp. Among these, from a viewpoint of the lipid productivity, *Nannochloropsis oculata* or *Nannochloropsis gaditana* is preferable, and *Nannochloropsis oculata* is more preferable.

As the plants, from a viewpoint of a high lipid content of seeds, *Arabidopsis thaliana*, *Brassica napus*, *Brassica raga*, *Cocos nucifera*, *Elaeis quineensis*, *cuphea*, *Glycine max*, *Zea mays*, *Oryza sativa*, *Helianthus annuus*, *Cinnamomum camphora*, or *Jatropha curcas* is preferable, and *Arabidopsis thaliana* is more preferable.

A vector for use as the plasmid vector for gene expression or a vector containing the gene expression cassette (plasmid) may be any vector capable of introducing the gene encoding the target protein into a host, and expressing the gene in the host cell. For example, a vector which has expression regulation regions such as a promoter and a terminator in accordance with the type of the host to be introduced, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the vector that can be used preferably in the present invention include, in the case of using a microorganism as the host, pBluescript (pBS) II SK(−) (manufactured by Stratagene), a pSTV-based vector (manufactured by Takara Bio), a pUC-based vector (manufactured by Takara Shuzo), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (McKenzie, T. et al., 1986, Plasmid 15(2), p. 93-103), pBR322 (manufactured by Takara Bio), pRS403 (manufactured by Stratagene), and pMW218/219 (manufactured by Nippon Gene). In particular, in the case of using *Escherichia coli* as the host, pBluescript II SK(−) or pMW218/219 is preferably used.

When the algae or the microalgae are used as the host, specific examples of the vector include pUC19 (manufactured by Takara Bio), P66 (*Chlamydomonas* Center), P-322 (*Chlamydomonas* Center), pPha-T1 (see Yangmin Gong, et al., Journal of Basic Microbiology, 2011, vol. 51, p. 666-672) and pJET1 (manufactured by COSMO 610). In particular, in the case of using the algae belonging to the genus *Nannochloropsis* as the host, pUC19, pPha-T1 or pJET1 is preferably used. Moreover, when the host is the algae belonging to the genus *Nannochloropsis*, the host can be transformed, with referring to the method described in Oliver Kilian, et al., Proceedings of the National Academy of Sciences of the United States of America, 2011, vol. 108(52), by using the DNA fragment consisting of the target gene of the present invention, a promoter and a terminator (gene expression cassette). Specific examples of this DNA fragment include a PCR-amplified DNA fragment and a restriction enzyme-cut DNA fragment.

In the case of using a plant cell as the host, examples of the vector include a pRI-based vector (manufactured by Takara Bio), a pBI-based vector (manufactured by Clontech), and an 1N3-based vector (manufactured by Inplanta Innovations). In particular, in the case of using *Arabidopsis thaliana* as the host, a pRI-based vector or a pBI-based vector is preferably used.

Moreover, a kind of promoter regulating the expression of the gene encoding a target protein, which is introduced into the expression vector, can also be appropriately selected according to a kind of the host to be used. Specific examples of the promoter that can be preferably used in the present invention include lac promoter, trp promoter, tac promoter, trc promoter, T7 promoter, SpoVG promoter, a promoter that relates to a substance that can be induced by addition of isopropyl β-D-1-thiogalactopyranoside (IPTG), Rubisco operon (rbc), PSI reaction center protein (psaAB), D1 protein of PSII (psbA), cauliflower mosaic virus 35S RNA promoter, promoters for housekeeping genes (e.g., tubulin promoter, actin promoter and ubiquitin promoter), *Brassica napus* or *Brassica rapa*-derived Napin gene promoter, plant-derived Rubisco promoter, a promoter of a violaxanthin/ (chlorophyll a)-binding protein gene derived from the genus *Nannochloropsis* (VCP1 promoter, VCP2 promoter) (Oliver Kilian, et al., Proceedings of the National Academy of Sciences of the United States of America, 2011, vol. 108 (52)), and a promoter of an oleosin-like protein LDSP (lipid droplet surface protein) gene derived from the genus *Nan-*

*nochloropsis* (Astrid Vieler, et al., PLOS Genetics, 2012, vol. 8(11): e1003064. DOI: 10.1371). In the case of using *Nannochloropsis* as the host in the present invention, the promoter of violaxanthin/(chlorophyll a)-binding protein gene, or the promoter of an oleosin-like protein LDSP gene derived from the genus *Nannochloropsis* can be preferably used.

Moreover, a kind of selection marker for confirming introduction of the gene encoding a target protein can also be appropriately selected according to a kind of the host to be used. Examples of the selection marker that can be preferably used in the present invention include drug resistance genes such as an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, and a hygromycin resistance gene. Further, it is also possible to use a deletion of an auxotrophy-related gene or the like as the selection marker gene.

Introduction of the gene encoding a target protein to the vector can be conducted by an ordinary technique such as restriction enzyme treatment and ligation.

Furthermore, the method for transformation can be appropriately selected from ordinary techniques according to a kind of the host to be used. Examples of the method for transformation include a transformation method of using calcium ion, a general competent cell transformation method, a protoplast transformation method, an electroporation method, an LP transformation method, a method of using *Agrobacterium*, a particle gun method, and the like. When the algae belonging to the genus *Nannochloropsis* are used as the host, transformation can also be performed by using the electroporation method described in Randor Radakovits, et al., Nature Communications, DOI: 10.1038/ncomms1688, 2012, or the like.

The selection of a transformant having a target gene fragment introduced therein can be carried out by utilizing the selection marker or the like. For example, the selection can be carried out by using an indicator whether a transformant acquires the drug resistance as a result of introducing a drug resistance gene into a host cell together with a target DNA fragment upon the transformation. Further, the introduction of a target DNA fragment can also be confirmed by PCR method using a genome as a template or the like.

In a host having the G3PDH gene on a genome, a method of modifying expression regulation regions of the gene and enhancing the expression of the gene is described.

The "expression regulation region" indicates the promoter or the terminator, in which these sequences are generally involved in regulation of the expression amount (transcription amount, translation amount) of the gene adjacent thereto. In a host having the above-described G3PDH gene on a genome, productivity of medium-chain fatty acids or lipids containing these medium-chain fatty acids as components can be improved by modifying expression regulation regions of the gene and enhancing the expression of the G3PDH gene.

Specific examples of the method of modifying the expression regulation regions include interchange of promoters. In the host having the above-mentioned G3PDH gene on the genome, the expression of the above-described G3PDH gene can be enhanced by interchanging the promoter of the gene (hereinafter, also referred to as "G3PDH promoter") with a promoter having higher transcriptional activity. For example, in *Nannochloropsis oculata* NIES-2145 strain being one of the hosts having the G3PDH genes on the genome, the NoG3PDH gene exists at the downstream of a DNA sequence consisting of the nucleotide sequence set forth in SEQ ID NO: 58, and a promoter region exists in the DNA sequence consisting of the nucleotide sequence set forth in SEQ ID NO: 58. The expression of the above-described G3PDH gene can be enhanced by partially or wholly interchanging the DNA sequences consisting of the nucleotide sequence set forth in SEQ ID NO: 58 with the promoter having higher transcriptional activity.

The promoter used for interchanging the G3PDH promoter is not particularly limited, and can be appropriately selected from the promoters that are higher in the transcriptional activity than the G3PDH promoter and suitable for production of the medium-chain fatty acids or the lipids containing these fatty acids as the components.

When the *Nannochloropsis* is used as a host, a tubulin promoter, a heat shock protein promoter, the above-described promoter of a violaxanthin/(chlorophyll a)-binding protein gene (VCP1 promoter (SEQ ID NO: 30), VCP2 promoter), or a promoter of an oleosin-like protein LDSP gene derived from the genus *Nannochloropsis* (SEQ ID NO: 18), can be preferably used. From a viewpoint of improvement in the productivity of medium-chain fatty acids or lipids containing these medium-chain fatty acids as components, the promoter of a violaxanthin/(chlorophyll a)-binding protein gene or the promoter of LDSP gene is more preferable.

The above-described modification of a promoter can employ according to an ordinarily method such as homologous recombination. Specifically, a linear DNA fragment containing upstream and downstream regions of a target promoter and containing other promoter instead of the target promoter is constructed, and the resultant DNA fragment is incorporated into a host cell to cause double crossover homologous recombination on the side upstream and downstream of the target promoter of the host genome. As a result, the target promoter on the genome is substituted with other promoter fragment, and the promoter can be modified.

The method of modifying a target promoter according to such homologous recombination can be conducted with, for example, reference to literature such as Besher et al., Methods in molecular biology, 1995, vol. 47, p. 291-302. In particular, in the case when the host is the algae belonging to the genus *Nannochloropsis*, specific region in a genome can be modified, with referring to literature such as Oliver Kilian, et al., Proceedings of the National Academy of Sciences of the United States of America, 2011, vol. 108 (52), by homologous recombination method.

The transformant of the present invention preferably has enhancing expression of a gene encoding a TE (hereinafter, also referred to as "TE gene"), in addition to the gene encoding the protein (A) or (B)

As described above, TE is an enzyme that hydrolyzes the thioester bond of the acyl-ACP synthesized by a fatty acid synthase such as the β-ketoacyl-ACP synthase (hereinafter, also referred to as "KAS") to produce a free fatty acid. The function of the TE terminates the fatty acid synthesis on the ACP, and then the thus-hydrolyzed fatty acid is supplied to the synthesis of polyunsaturated fatty acid or triacylglycerol (hereinafter, also referred to as "TAG") or the like. Then, the above-described G3PDH is involved in the TAG synthesis or the like.

Therefore, lipid productivity of the transformant to be used for the lipid production, particularly productivity of the fatty acids can be further improved by increasing the content of a substrate for TAG which is synthesized by G3PDH, due to the enhancing of the expression of the TE gene, in addition to the G3PDH gene. Furthermore, as shown in Examples mentioned later, total amount of the amounts of each of the fatty acids (total amount of the fatty acids) can be also improved by enhancing the expression of the TE gene, in addition to the G3PDH gene.

The TE that can be used in the present invention merely needs to be the protein having acyl-ACP thioesterase activity (hereinafter, also referred to as "TE activity"). Herein, the term "TE activity" means an activity of hydrolyzing the thioester bond of the acyl-ACP.

To date, several TEs having different reaction specificities depending on the number of carbon atoms and the number of unsaturated bonds of the acyl group (fatty acid residue) constituting the acyl-ACP substrate are identified. Therefore, TE is considered to be an important factor in determining the fatty acid composition of an organism. In particular, when a host originally having no gene encoding a TE is used in the transformation, it is preferable to enhance the expression of the gene encoding a TE. In addition, according to enhancing the expression of the TE gene having substrate specificity to the medium-chain acyl-ACP, the productivity of medium-chain fatty acids is improved. The productivity of medium-chain fatty acids is further improved by introducing such a gene.

The TE that can be used in the present invention can be appropriately selected from ordinary TEs and proteins functionally equivalent to the TEs, according to a kind of host or the like.

Specific examples thereof include TE derived from *Cuphea calophylla* subsp. *mesostemon* (GenBank ABB71581); TE derived from *Cinnamomum camphora* (GenBank AAC49151.1); TE derived from *Myristica fragrans* (GenBank AAB71729); TE derived from *Myristica fragrans* (GenBank AAB71730); TE derived from *Cuphea lanceolata* (GenBank CAA54060); TE derived from *Cuphea hookeriana* (GenBank Q39513); TE derived from *Ulumus americana* (GenBank AAB71731); TE derived from *Sorghum bicolor* (GenBank EER87824); TE derived from *Sorghum bicolor* (GenBank EER88593); TE derived from *Cocos nucifera* (CnFatB1: see Jing et al. BMC Biochemistry 2011, 12:44); TE derived from *Cocos nucifera* (CnFatB2: see Jing et al., BMC Biochemistry, 2011, 12:44); TE derived from *Cuphea viscosissima* (CvFatB1: see Jing et al., BMC Biochemistry, 2011, 12:44); TE derived from *Cuphea viscosissima* (CvFatB2: see Jing et al., BMC Biochemistry, 2011, 12:44); TE derived from *Cuphea viscosissima* (CvFatB3: see Jing et al., BMC Biochemistry, 2011, 12:44); TE derived from *Elaeis quineensis* (GenBank AAD42220); TE derived from *Desulfovibrio vulgaris* (GenBank ACL08376); TE derived from *Bacteroides fragilis* (GenBank CAH09236); TE derived from *Parabacteriodes distasonis* (GenBank ABR43801); TE derived from *Bacteroides thetaiotaomicron* (GenBank AA077182); TE derived from *Clostridium asparagiforme* (GenBank EEG55387); TE derived from *Bryanthella formatexigens* (GenBank EET61113); TE derived from *Geobacillus* sp. (GenBank EDV77528); TE derived from *Streptococcus dysgalactiae* (GenBank BAH81730); TE derived from *Lactobacillus brevis* (GenBank ABJ63754); TE derived from *Lactobacillus plantarum* (GenBank CAD63310); TE derived from *Anaerococcus tetradius* (GenBank EEI82564); TE derived from *Bdellovibrio bacteriovorus* (GenBank CAE80300); TE derived from *Clostridium thermocellum* (GenBank ABN54268); TE derived from *Umbellularia californica* (California bay) (hereinafter, also referred to as "BTE") (GenBank AAA34215.1, SEQ ID NO: 29, nucleotide sequence of a gene encoding thereof; SEQ ID NO: 26); TE derived from *Nannochloropsis oculata* (hereinafter, also referred to as "NoTE") (SEQ ID NO: 38, nucleotide sequence of a gene encoding thereof; SEQ ID NO: 39); TE derived from *Cocos nucifera* (SEQ ID NO: 59, nucleotide sequence of a gene encoding thereof; SEQ ID NO: 60); TE derived from *Nannochloropsis gaditana* (SEQ ID NO: 61, nucleotide sequence of a gene encoding thereof; SEQ ID NO: 62); TE derived from *Nannochloropsis granulata* (SEQ ID NO: 63, nucleotide sequence of a gene encoding thereof; SEQ ID NO: 64); and TE derived from *Symbiodinium microadriaticum* (SEQ ID NO: 65, nucleotide sequence of a gene encoding thereof; SEQ ID NO: 66).

Moreover, as the proteins functionally equivalent to them, a protein consisting of an amino acid sequence having 50% or more, preferably 60% or more, more preferably 65% or more, more preferably 70% or more, more preferably 75% or more, more preferably 80% or more, more preferably 85% or more, more preferably 90% or more, and further preferably 95% or more identity with the amino acid sequence of any one of the TEs described above, and having TE activity, can be also used. Alternatively, a protein consisting of an amino acid sequence in which 1 or several amino acids, (for example, preferably 1 or more and 149 or less amino acids, more preferably 1 or more and 119 or less amino acids, further preferably 1 or more and 104 or less amino acids, furthermore preferably 1 or more and 90 or less amino acids, furthermore preferably 1 or more and 75 or less amino acids, furthermore preferably 1 or more and 60 or less amino acids, furthermore preferably 1 or more and 45 or less amino acids, furthermore preferably 1 or more and 30 or less amino acids, and furthermore preferably 1 or 15 amino acids), are deleted, substituted, inserted or added to the amino acid sequence of any one of the TEs described above, and having TE activity, can be also used.

Among these TEs described above, from a viewpoint of the substrate specificity for medium-chain acyl-ACP, BTE (SEQ ID NO: 29, nucleotide sequence of a gene encoding thereof; SEQ ID NO: 26), NoTE (SEQ ID NO: 38, nucleotide sequence of a gene encoding thereof; SEQ ID NO: 39), TE derived from *Cocos nucifera* (SEQ ID NO: 59, nucleotide sequence of a gene encoding thereof; SEQ ID NO: 60), TE derived from *Nannochloropsis gaditana* (SEQ ID NO: 61, nucleotide sequence of a gene encoding thereof; SEQ ID NO: 62), TE derived from *Nannochloropsis granulata* (SEQ ID NO: 63, nucleotide sequence of a gene encoding thereof; SEQ ID NO: 64), TE derived from *Symbiodinium microadriaticum* (SEQ ID NO: 65, nucleotide sequence of a gene encoding thereof; SEQ ID NO: 66), a protein consisting of an amino acid sequence having 50% or more, preferably 60% or more, more preferably 65% or more, more preferably 70% or more, more preferably 75% or more, more preferably 80% or more, more preferably 85% or more, more preferably 90% or more, and further preferably 95% or more identity with the amino acid sequence of any one of the TEs, and having TE activity for medium-chain acyl-ACP (for example, a protein which is encoded by the DNA consisting of the nucleotide sequence set forth in SEQ ID NO: 44), or a protein consisting of an amino acid sequence in which 1 or several amino acids, (for example, preferably 1 or more and 149 or less amino acids, more preferably 1 or more and 119 or less amino acids, further preferably 1 or more and 104 or less amino acids, furthermore preferably 1 or more and 90 or less amino acids, furthermore preferably 1 or more and 75 or less amino acids, furthermore preferably 1 or more and 60 or less amino acids, furthermore preferably 1 or more and 45 or less amino acids, furthermore preferably 1 or more and 30 or less amino acids, and furthermore preferably 1 or 15 amino acids), are deleted, substituted, inserted or added to the amino acid sequence of any one of the TEs, and having TE activity for medium-chain acyl-ACP, is preferable.

The sequence information or the like of these TEs and the genes encoding thereof can be obtained from, for example, National Center for Biotechnology Information, NCBI, or the like.

The TE activity of the protein can be confirmed by, for example, introducing a DNA produced by linking the acyl-ACP thioesterase gene to the downstream of a promoter which functions in a host cell such as *Escherichia coli*, into a host cell which lacks a fatty acid degradation system, culturing the thus-obtained cell under the conditions suitable for the expression of the introduced TE gene, and analyzing any change caused thereby in the fatty acid composition of the host cell or the cultured liquid by using a gas chromatographic analysis or the like.

Alternatively, the TE activity can be measured by introducing a DNA produced by linking the TE gene to the downstream of a promoter which functions in a host cell such as *Escherichia coli*, into a host cell, culturing the thus-obtained cell under the conditions suitable for the expression of the introduced TE gene, and subjecting a disruption liquid of the cell to a reaction which uses acyl-ACPs, as substrates, prepared according to the method of Yuan et al. (Yuan L. et al., Proc. Natl. Acad. Sci. U.S.A., 1995, vol. 92 (23), p. 10639-10643).

The transformants in which expression of the gene TE is enhanced can be prepared by an ordinary method. For example, the transformants can be prepared by a method similar to the above-mentioned method for enhancing expression of the G3PDH gene, such as a method of introducing a TE gene into a host, and a method of modifying expression regulation regions of a gene in a host having the TE gene on a genome.

In the transformant of the present invention, the expression of a KAS gene, in addition to the above-described gene encoding the protein (A) or (B), is also preferably enhanced.

A KAS, which is an enzyme involved in fatty acid synthetic pathway, is an enzyme involved in control of chain length of the acyl group. In plants, four kinds of KASs having different function respectively, namely KAS I, KAS II, KAS III and KAS IV are known to exist. Among these, KAS III functions in a stage of starting a chain length elongation reaction to elongate the acetyl-ACP (or acetyl-CoA) having 2 carbon atoms to the β-ketoacyl-ACP having 4 carbon atoms. In the subsequent elongation reaction, KAS I, KAS II and KAS IV are involved. KAS I is mainly involved in the elongation reaction to the palmitoyl-ACP having 16 carbon atoms, and KAS II is mainly involved in the elongation reaction to the stearoyl-ACP having 18 carbon atoms. On the other hand, it is believed that KAS IV is involved in the elongation reaction to medium-chain acyl-ACP having 6 to 14 carbon atoms.

The KAS involves in a synthesis of a precursor (acyl-ACP) of the free fatty acid to be used as the substrate upon synthesizing the TAG. Therefore, an amount of the acyl-ACP increases by enhancing the expression of the KAS gene, and the content of the free fatty acid serving as the substrate for the TAG synthesis increases. Then, an amount of G3P being a skeleton of the TAG increases by further enhancing the expression of the G3PDH gene, and therefore a TAG synthesis amount increases as a whole, and the lipid productivity in the transformant to be used for the lipid production, particularly the productivity of the fatty acids can be further improved. Furthermore, as shown in Examples mentioned later, total amount of the amounts of each of the fatty acids (total amount of the fatty acids) can also be improved by enhancing the expression of the KAS gene, in addition to the G3PDH gene.

The KAS that can be used in the present invention merely needs to be the protein having β-ketoacyl-ACP synthase activity (hereinafter, also referred to as "KAS activity"). Herein, the term "KAS activity" means the activity to catalyze the condensation reaction of the acetyl-ACP (or acetyl-CoA) or the acyl-ACP with the malonyl-ACP.

As described above, KAS is categorized into KAS I, KAS II, KAS III and KAS IV according to their substrate specificity. Therefore, KAS is considered to be an important factor in determining the fatty acid composition of an organism. Therefore, lipid productivity can be further improved by enhancing the expression of the KAS gene.

The KAS that can be used in the present invention can be appropriately selected from ordinary KASs and proteins functionally equivalent to the KASs, according to a kind of host or the like.

Specific examples thereof include KAS derived from *Nannochloropsis oculata* (SEQ ID NO: 48, nucleotide sequence of a gene encoding thereof; SEQ ID NO: 49, SEQ ID NO:75, nucleotide sequence of a gene encoding thereof; SEQ ID NO: 76), KAS derived from *Nannochloropsis gaditana* (SEQ ID NO: 67, nucleotide sequence of a gene encoding thereof; SEQ ID NO: 68) KAS derived from *Umbellularia californica* (SEQ ID NO: 69, nucleotide sequence of a gene encoding thereof; SEQ ID NO: 70, SEQ ID NO: 71, nucleotide sequence of a gene encoding thereof; SEQ ID NO: 72), KAS derived from *Cinnamomum camphora* (SEQ ID NO: 73, nucleotide sequence of a gene encoding thereof; SEQ ID NO: 74), KAS derived from *Cocos nucifera* (SEQ ID NO: 77, nucleotide sequence of a gene encoding thereof; SEQ ID NO: 78), KAS derived from *Cuphea hookeriana* (SEQ ID NO: 79, nucleotide sequence of a gene encoding thereof; SEQ ID NO: 80), and KAS derived from *Cuphea lanceolata* (SEQ ID NO: 81, nucleotide sequence of a gene encoding thereof; SEQ ID NO: 82). Moreover, as the proteins functionally equivalent to them, a protein consisting of an amino acid sequence having 50% or more, preferably 60% or more, more preferably 65% or more, more preferably 70% or more, more preferably 75% or more, more preferably 80% or more, more preferably 85% or more, more preferably 90% or more, and further preferably 95% or more identity with the amino acid sequence of any one of the KASs described above, and having KAS activity, can be also used. Alternatively, a protein consisting of an amino acid sequence in which 1 or several amino acids, (for example, preferably 1 or more and 255 or less amino acids, more preferably 1 or more and 204 or less amino acids, further preferably 1 or more and 179 or less amino acids, furthermore preferably 1 or more and 153 or less amino acids, furthermore preferably 1 or more and 128 or less amino acids, furthermore preferably 1 or more and 102 or less amino acids, furthermore preferably 1 or more and 77 or less amino acids, furthermore preferably 1 or more and 51 or less amino acids, and furthermore preferably 1 or 26 amino acids), are deleted, substituted, inserted or added to the amino acid sequence of any one of the KASs described above, and having KAS activity, can be also used.

Among these KASs described above, from a viewpoint of the medium-chain β-ketoacyl-ACP synthesis activity, KAS derived from *Nannochloropsis oculata* (SEQ ID NO: 48, nucleotide sequence of a gene encoding thereof; SEQ ID NO: 49, SEQ ID NO: 75, nucleotide sequence of a gene encoding thereof; SEQ ID NO: 76), KAS derived from *Nannochloropsis gaditana* (SEQ ID NO: 67, nucleotide sequence of a gene encoding thereof; SEQ ID NO: 68), KAS derived from *Umbellularia californica* (SEQ ID NO: 69, nucleotide sequence of a gene encoding thereof; SEQ ID NO: 70, SEQ ID NO: 71, nucleotide sequence of a gene encoding thereof; SEQ ID NO: 72), KAS derived from *Cinnamomum camphora* (SEQ ID NO: 73, nucleotide sequence of a gene encoding thereof; SEQ ID NO: 74), KAS derived from *Cocos nucifera* (SEQ ID NO: 77, nucleotide sequence of a gene encoding thereof; SEQ ID NO: 78), KAS derived from *Cuphea hookeriana* (SEQ ID NO: 79, nucleotide sequence of a gene encoding thereof; SEQ ID NO: 80), KAS derived from *Cuphea lanceolata* (SEQ ID NO: 81, nucleotide sequence of a gene encoding thereof; SEQ ID NO: 82), or a protein consisting of an amino acid sequence having 50% or more, preferably 60% or more, more preferably 65% or more, more preferably 70% or more, more preferably 75% or more, more preferably 80% or more, more preferably 85% or more, more preferably 90% or more, and further preferably 95% or more identity with the amino acid sequence of any one of the KASs, and having medium-chain β-ketoacyl-ACP synthase activity, or a protein consisting of an amino acid sequence in which 1 or several amino acids, (for example, preferably 1 or more and 255 or less amino acids, more preferably 1 or more and 204 or less amino acids, further preferably 1 or more and 179 or less amino acids, furthermore preferably 1 or more and 153 or less amino acids, furthermore preferably 1 or more and 128 or less amino acids, furthermore preferably 1 or more and 102 or less amino acids, furthermore preferably 1 or more and 77 or less amino acids, furthermore preferably 1 or more and 51 or less amino acids, and furthermore preferably 1 or 26 amino acids), are deleted, substituted, inserted or added to the amino acid sequence of any one of the KASs, and having medium-chain β-ketoacyl-ACP synthase activity, is preferable.

The sequence information or the like of these KASs and the genes encoding thereof can be obtained from, for example, National Center for Biotechnology Information, NCBI, or the like.

The KAS activity of the protein can be confirmed by, for example, introducing a DNA produced by linking a gene encoding the protein to the downstream of a promoter which functions in a host cell, into a host cell which lacks a fatty acid degradation system, culturing the thus-obtained cell under the conditions suitable for the expression of the introduced gene, and analyzing any change caused thereby in the fatty acid composition of the host cell or the cultured liquid by an ordinary technique. Alternatively, the KAS activity can be confirmed by allowing, in the above-described system, coexpression of TE, and being compared with fatty acid composition in the case of allowing merely single expression of TE. Alternatively, the KAS activity can be confirmed by introducing a DNA produced by linking a gene encoding the protein to the downstream of a promoter which functions in a host cell, into a host cell, culturing the thus-obtained cell under the conditions suitable for the expression of the introduced gene, and subjecting a disruption liquid of the cell to a chain length elongation reaction.

The transformants in which expression of the gene KAS is enhanced can be prepared by an ordinary method. For example, the transformants can be prepared by a method similar to the above-mentioned method for enhancing expression of the G3PDH gene, such as a method of introducing a KAS gene into a host, and a method of modifying expression regulation regions of a gene in a host having the KAS gene on a genome.

Furthermore, in the transformant of the present invention, expression of a gene encoding an acyltransferase or the like, in addition to the above-described gene encoding the protein (A) or (B), is also preferably enhanced.

As mentioned above, the acyltransferase is an enzyme catalyzing the acylation which is necessary for the TAG synthesis. Therefore, productivity of medium-chain fatty acids can be further improved by enhancing the expression of the gene encoding the acyltransferase having specificity for the medium-chain fatty acid, such as diacylglycerol acyltransferase having specificity for the medium-chain fatty acid, in addition to the G3PDH gene.

The acyltransferase, which can be used in the present invention, can be appropriately selected from the normal acyltransferase, or proteins functionally equivalent to the acyltransferase, according to a kind of host or the like.

Further, the transformants in which the expression of the gene is enhanced can be prepared by an ordinary method. For example, the transformants can be prepared by a method similar to the above-described method for enhancing the expression of the G3PDH gene, such as a method for introducing a gene encoding the acyltransferase into a host, a method for modifying expression regulation regions of a gene in the host having the gene encoding the acyltransferase on a genome, or the like.

In the transformant of the present invention, productivity of the medium-chain fatty acids or the lipids containing these fatty acids as components is improved in comparison with the host in which the expression of the gene encoding the protein (A) or (B) is not enhanced. Accordingly, if the transformant of the present invention is cultured under suitable conditions and then the medium-chain fatty acids or the lipids containing these fatty acids as components are collected from an obtained cultured product or an obtained growth product, the medium-chain fatty acids or the lipids containing these fatty acids as components can be efficiently produced.

Further, in the transformant, total amount of all fatty acids to be produced is also significantly improved in comparison with a host. Therefore, if the transformant of the present invention is cultured under suitable conditions and then the fatty acids or the lipids containing these fatty acids as components are collected from an obtained cultured product or an obtained growth product, the fatty acids or the lipids containing these fatty acids as components can be efficiently produced.

Herein, the term "cultured product" means liquid medium and a transformant subjected to cultivation, and the term "growth product" means a transformant subjected to growth.

The culture condition of the transformant of the present invention can be appropriately selected in accordance with the type of the host, and any ordinary used culture condition for the host can be employed. Further, from a viewpoint of the production efficiency of fatty acids, for example, precursor substances involved in the fatty acid biosynthesis system, such as glycerol, acetic acid or glucose, may be added to the medium.

For example, in the case of using *Escherichia coli* as the host, culturing of *Escherichia coli* may be carried out in LB medium or Overnight Express Instant TB Medium (Novagen) at 30° C. to 37° C. for half a day to 1 day.

In the case of using *Arabidopsis thaliana* as the host, for example, growth of *Arabidopsis thaliana* may be carried out at soil under the temperature conditions of 20° C. to 25° C., by continuously irradiating white light or under light illumination conditions of a light period of 16 hours and a dark period of 8 hours, for one to two months.

In the case of using algae as the host, medium based on natural seawater or artificial seawater may be used. Alternatively, commercially available culture medium may also be used. Specific examples of the culture medium include f/2 medium, ESM medium, Daigo's IMK medium, L1 medium and MNK medium. Above all, from viewpoints of an improvement in the lipid productivity and a nutritional ingredient concentration, f/2 medium, ESM medium or Daigo's IMK medium is preferred, f/2 medium or Daigo's IMK medium is more preferred, and f/2 medium is further preferred. For growth promotion of the algae and an improvement in productivity of fatty acids, a nitrogen source, a phosphorus source, metal salts, vitamins, trace metals or the like can be appropriately added to the culture medium.

An amount of the transformant to be seeded to the culture medium is appropriately selected. In view of viability, the amount is preferably 1 to 50% (vol/vol), and more preferably 1 to 10% (vol/vol), per culture medium. Culture temperature is not particularly limited within the range in which the temperature does not adversely affect growth of the algae, and is ordinarily in the range of 5 to 40° C. From viewpoints of the growth promotion of the algae, the improvement in productivity of fatty acids, and reduction of production cost, the temperature is preferably 10 to 35° C., and more preferably 15 to 30° C.

Moreover, the algae are preferably cultured under irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of fatty acids, irradiance during the light irradiation is preferably in the range of 100 to 50,000 lx, more preferably in the range of 300 to 10,000 lx, and further preferably 1,000 to 6,000 lx. Moreover, an interval of the light irradiation is not particularly limited. From the viewpoints in a manner similar to the viewpoints described above, the irradiation is preferably performed under a light and dark cycle. In 24 hours, a light period is preferably from 8 to 24 hours, more preferably from 10 to 18 hours, and further preferably 12 hours.

Moreover, the algae are preferably cultured in the presence of a carbon dioxide-containing gas or in a culture medium containing carbonate such as sodium hydrogen carbonate so that the photosynthesis can be made. A concentration of carbon dioxide in the gas is not particularly limited. From viewpoints of the growth promotion and the improvement in the productivity of fatty acids, the concentration is preferably from 0.03 (which is the same degree as the concentration under atmospheric conditions) to 10%, more preferably from 0.05 to 5%, further preferably from 0.1 to 3%, and furthermore preferably from 0.3 to 1%. A concentration of the carbonate is not particularly limited. When the sodium hydrogen carbonate is used, for example, from viewpoints of the growth promotion and the improvement in the productivity of fatty acids, the concentration is preferably from 0.01 to 5% by mass, more preferably from 0.05 to 2% by mass, and further preferably from 0.1 to 1% by mass.

A culture time is not particularly limited, and the culture may be performed for a long time (for example, about 150 days) so that an alga body in which the lipids are accumulated at a high concentration can grow at a high concentration. From viewpoints of the growth promotion of the algae, the improvement in the productivity of fatty acids, and the reduction of production cost, the culture time is preferably from 3 to 90 days, more preferably from 3 to 30 days, and further preferably from 7 to 30 days. The culture may be performed in any of aerated and agitated culture, shaking culture or static culture. From a viewpoint of improving air-permeability, aerated and agitated culture, or shaking culture is preferred, and aerated and agitated culture is more preferred.

A method of collecting the lipids from the cultured product or growth product is appropriately selected from an ordinary method. For example, lipid components can be isolated and collected from the above-described cultured product or growth product by means of filtration, centrifugation, cell disruption, gel filtration chromatography, ion exchange chromatography, chloroform/methanol extraction, hexane extraction, ethanol extraction, or the like. In the case of carrying out the larger scales culturing, lipids can be obtained by collecting oil components from the cultured product or growth product through pressing or extraction, and then performing general purification processes such as degumming, deacidification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

The lipids produced in the production method of the present invention preferably contain fatty acids or fatty acid compounds, and more preferably contain fatty acids or fatty acid ester compounds thereof, in view of usability thereof.

In view of usability for a surfactant or the like, the fatty acid or the ester compound thereof contained in the lipid is preferably a medium-chain fatty acid or an ester compound thereof, more preferably a fatty acid having 6 or more and 14 or less carbon atoms or an ester compound thereof, more preferably a fatty acid having 8 or more and 14 or less carbon atoms or an ester compound thereof, more preferably a fatty acid having 10 or more and 14 or less carbon atoms or an ester compound thereof, more preferably a fatty acid having 12 or more and 14 or less carbon atoms or an ester compound thereof, more preferably a fatty acid having 12 or 14 carbon atoms or an ester compound thereof, more preferably a saturated fatty acid having 12 or 14 carbon atoms (lauric acid or myristic acid) or an ester compound thereof.

From a viewpoint of the productivity, the fatty acid ester compound is preferably a simple lipid or a complex lipid, more preferably a simple lipid, and further preferably a triacylglycerol.

The lipid obtained by the production method of the present invention can be utilized for food, as well as a plasticizer, an emulsifier incorporated into cosmetic products or the like, a cleansing agent such as a soap or a detergent, a fiber treatment agent, a hair conditioning agent, a disinfectant or an antiseptic.

With regard to the embodiments described above, the present invention also discloses methods of producing lipids, methods of improving lipid productivity, methods of modifying composition of fatty acids to be produced, proteins, genes, recombinant vectors, organisms, transformants, and methods of producing a transformant, described below.
<1> A method of producing lipids, containing the steps of:
culturing a transformant in which the expression of a gene encoding the following protein (A) or (B) is enhanced, and producing fatty acids or lipids containing these fatty acids as components:
(A) a protein consisting of the amino acid sequence set forth in SEQ ID NO: 1; and
(B) a protein consisting of an amino acid sequence having 64% or more, preferably 65% or more, more preferably 70% or more, further preferably 75% or more, furthermore preferably 80% or more, furthermore preferably 83% or more, furthermore preferably 85% or more, furthermore preferably 87% or more, furthermore preferably 90% or more, furthermore preferably 93% or more, furthermore preferably 95% or more, furthermore preferably 97% or more, furthermore preferably 98% or more, and furthermore preferably 99% or more identity with the amino acid sequence of the protein (A), and having G3PDH activity.

<2> A method of improving lipid productivity, containing the steps of:
enhancing the expression of a gene encoding the protein (A) or (B) in a transformant, and
improving the productivity of medium-chain fatty acids or lipids containing these fatty acids as components, produced in a cell of the transformant.

<3> A method of improving lipid productivity, containing the steps of:
enhancing the expression of a gene encoding the protein (A) or (B) in a transformant, and
improving the total amount of all fatty acids produced in a cell of the transformant.

<4> A method of modifying the composition of lipids, containing the steps of:
enhancing the expression of a gene encoding the protein (A) or (B) in a transformant, and
improving the productivity of medium-chain fatty acids or lipids containing these fatty acids as components produced in a cell of the transformant, to modify the composition of fatty acids or lipids in all fatty acids or all lipids to be produced.

<5> The method described in any one of the above items <1> to <4>, wherein the gene encoding the protein (A) or (B) is introduced into a host, to enhance the expression of the gene.

<6> A method of producing lipids, containing the steps of:
culturing a transformant into which a gene encoding the protein (A) or (B) is introduced, and
producing fatty acids or lipids containing these fatty acids as components.

<7> A method of improving lipid productivity, containing the steps of:
introducing a gene encoding the protein (A) or (B) into a host, and thereby producing a transformant, and
improving productivity of medium-chain fatty acids or lipids containing these fatty acids as components produced in a cell of the transformant.

<8> A method of improving lipid productivity, containing the steps of:
introducing a gene encoding the protein (A) or (B) into a host, and thereby producing a transformant, and
improving the total amount of all fatty acids produced in a cell of the transformant.

<9> A method of modifying the composition of lipids, containing the steps of:
introducing a gene encoding the protein (A) or (B) into a host, and thereby producing a transformant, and
enhancing productivity of medium-chain fatty acids or lipids containing these fatty acids as components produced in a cell of the transformant, to modify the composition of fatty acids or lipids in all fatty acids or all lipids to be produced.

<10> The method described in any one of the above items <1> to <9>, wherein the protein (B) consists of an amino acid sequence in which 1 or several, preferably 1 or more and 167 or less, preferably 1 or more and 162 or less, more preferably 1 or more and 139 or less, further preferably 1 or more and 116 or less, furthermore preferably 1 or more and 93 or less, furthermore preferably 1 or more and 69 or less, furthermore preferably 1 or more and 60 or less, furthermore preferably 1 or more and 46 or less, furthermore preferably 1 or more and 32 or less, furthermore preferably 1 or more and 23 or less, furthermore preferably 1 or more and 13 or less, furthermore preferably 1 or more and 9 or less, and furthermore preferably 1 or more and 4 or less amino acids, are deleted, substituted, inserted or added to the amino acid sequence of the protein (A).

<11> The method described in any one of the above items <1> to <10>, wherein the gene encoding the protein (A) or (B) is a gene consisting of the following DNA (a) or (b):
(a) a DNA consisting of the nucleotide sequence set forth in SEQ ID NO: 2; and
(b) a DNA consisting of a nucleotide sequence having 59% or more, preferably 60% or more, more preferably 65% or more, further preferably 70% or more, furthermore preferably 75% or more, furthermore preferably 80% or more, furthermore preferably 83% or more, furthermore preferably 85% or more, furthermore preferably 87% or more, furthermore preferably 90% or more, furthermore preferably 93% or more, furthermore preferably 95% or more, furthermore preferably 97% or more, furthermore preferably 98% or more, and furthermore preferably 99% or more, identity with the nucleotide sequence of the DNA (a), and encoding the protein having G3PDH activity.

<12> The method described in the above item <11>, wherein the DNA (b) is a DNA consisting of a nucleotide sequence in which 1 or several, preferably 1 or more and 573 or less, more preferably 1 or more and 559 or less, further preferably 1 or more and 489 or less, furthermore preferably 1 or more and 419 or less, furthermore preferably 1 or more and 349 or less, furthermore preferably 1 or more and 279 or less, furthermore preferably 1 or more and 209 or less, furthermore preferably 1 or more and 181 or less, furthermore preferably 1 or more and 139 or less, furthermore preferably 1 or more and 97 or less, furthermore preferably 1 or more and 69 or less, furthermore preferably 1 or more and 41 or less, furthermore preferably 1 or more and 27 or less, and furthermore preferably 1 or more and 13 or less nucleotides, are deleted, substituted, inserted or added to the nucleotide sequence of the DNA (a), and encoding the protein having G3PDH activity, or a DNA capable of hybridizing with a DNA consisting of the nucleotide sequence complementary with the DNA (a) under a stringent condition, and encoding the protein having G3PDH activity.

<13> The method described in any one of the above items <1> to <12>, wherein expression of a gene encoding a TE is enhanced in the transformant.

<14> The method described in the above item <13>, wherein the TE is a TE having substrate specificity to a medium-chain acyl-ACP.

<15> The method described in the above item <13> or <14>, wherein the TE is a protein consisting of the amino acid sequence set forth in SEQ ID NO: 29, SEQ ID NO: 38, SEQ ID NO: 59, SEQ ID NO: 61, SEQ ID NO: 63, or SEQ ID NO: 65; a protein consisting of an amino acid sequence having 50% or more, preferably 60% or more, more preferably 65% or more, more preferably 70% or more, more preferably 75% or more, more preferably 80% or more, more preferably 85% or more, more preferably 90% or more, and further preferably 95% or more identity with the amino acid sequence of the protein, and having TE activity for medium-chain acyl-ACP; or a protein consisting of an amino acid sequence in which 1 or several amino acids, preferably 1 or more and 149 or less amino acids, more preferably 1 or more and 119 or less amino acids, further preferably 1 or more and 104 or less amino acids, furthermore preferably 1 or more and 90 or less amino acids, furthermore preferably 1 or more and 75 or less amino acids, furthermore preferably 1 or more and 60 or less amino acids, furthermore preferably 1 or more and 45 or less amino acids, furthermore preferably 1 or more and 30 or less amino acids, or furthermore preferably 1 or 15 amino acids, are deleted, substituted, inserted or added to the amino acid sequence of the protein, and having TE activity for medium-chain acyl-ACP.

<16> The method described in any one of the above items <1> to <15>, wherein expression of a gene encoding a KAS is enhanced in the transformant.

<17> The method described in the above item <16>, wherein the KAS is a KAS having medium-chain β-ketoacyl-ACP synthase activity.

<18> The method described in the above item <16> or <17>, wherein the KAS is a protein consisting of the amino acid sequence set forth in SEQ ID NO: 48, SEQ ID NO: 75, SEQ ID NO: 67, SEQ ID NO: 69, SEQ ID NO: 71, SEQ ID NO: 73, SEQ ID NO: 77, SEQ ID NO: 79, or SEQ ID NO: 81; a protein consisting of an amino acid sequence having 50% or more, preferably 60% or more, more preferably 65% or more, more preferably 70% or more, more preferably 75% or more, more preferably 80% or more, more preferably 85% or more, more preferably 90% or more, and further preferably 95% or more identity with the amino acid sequence of the protein, and having medium-chain β-ketoacyl-ACP synthase activity; or a protein consisting of an amino acid sequence in which 1 or several amino acids, preferably 1 or more and 255 or less amino acids, more preferably 1 or more and 204 or less amino acids, further preferably 1 or more and 179 or less amino acids, furthermore preferably 1 or more and 153 or less amino acids, furthermore preferably 1 or more and 128 or less amino acids, furthermore preferably 1 or more and 102 or less amino acids, furthermore preferably 1 or more and 77 or less amino acids, furthermore preferably 1 or more and 51 or less amino acids, or furthermore preferably 1 or 26 amino acids, are deleted, substituted, inserted or added to the amino acid sequence of the protein, and having medium-chain β-ketoacyl-ACP synthase activity.

<19> The method described in any one of the above items <1> to <18>, wherein the transformant is a microorganism or a plant.

<20> The method described in the above item <19>, wherein the microorganism is a microalga.

<21> The method described in the above item <20>, wherein the microalga is an alga belonging to the genus *Nannochloropsis*, preferably *Nannochloropsis oculata*.

<22> The method described in the above item <19>, wherein the microorganism is *Escherichia coli*.

<23> The method described in the above item <19>, wherein the plant is *Arabidopsis thaliana*.

<24> The method described in any one of the above items <1> to <23>, wherein the lipids contain a medium-chain fatty acid or an ester compound thereof, preferably a fatty acid having 6 or more and 14 or less carbon atoms or an ester compound thereof, more preferably a fatty acid having 8 or more and 14 or less carbon atoms or an ester compound thereof, more preferably a fatty acid having 10 or more and 14 or less carbon atoms or an ester compound thereof, more preferably a fatty acid having 12 or more and 14 or less carbon atoms or an ester compound thereof, more preferably a fatty acid having 12 or 14 carbon atoms or an ester compound thereof, more preferably a saturated fatty acid having 12 or 14 carbon atoms (lauric acid or myristic acid) or an ester compound thereof.

<25> The protein (A) or (B) specified in any one of the above items <1> to <24>.

<26> A gene encoding the protein described in the above item <25>.

<27> A gene consisting of the DNA (a) or (b) specified in any one of the above items <1> to <24>.

<28> A recombinant vector, containing the gene described in the above item <26> or <27>.

<29> A transformant, wherein the expression of the gene described in the above item <26> or <27> is enhanced, and at least either of the productivity of medium-chain fatty acids or lipids containing these fatty acids as components, and the total amount of all fatty acids produced in a cell of the transformant is improved.

<30> A transformant, which is obtained by introducing the gene described in the above item <26> or <27> or the recombinant vector described in the above item <28> into a host.

<31> A method of producing a transformant, containing introducing the gene described in the above item <26> or <27> or the recombinant vector described in the above item <28> into a host.

<32> The transformant or the method of producing the same described in any one of the above items <29> to <31>, wherein expression of a gene encoding a TE is enhanced.

<33> The transformant or the method of producing the same described in the above item <32>, wherein the TE is a TE having substrate specificity to a medium-chain acyl-ACP.

<34> The transformant or the method of producing the same described in the above item <32> or <33>, wherein the TE is a protein consisting of the amino acid sequence set forth in SEQ ID NO: 29, SEQ ID NO: 38, SEQ ID NO: 59, SEQ ID NO: 61, SEQ ID NO: 63, or SEQ ID NO: 65; a protein consisting of an amino acid sequence having 50% or more, preferably 60% or more, more preferably 65% or more, more preferably 70% or more, more preferably 75% or more, more preferably 80% or more, more preferably 85% or more, more preferably 90% or more, and further preferably 95% or more identity with the amino acid sequence of the protein, and having TE activity for medium-chain acyl-ACP; or a protein consisting of an amino acid sequence in which 1 or several amino acids, preferably 1 or more and 149 or less amino acids, more preferably 1 or more and 119 or less amino acids, further preferably 1 or more and 104 or less amino acids, furthermore preferably 1 or more and 90 or less amino acids, furthermore preferably 1 or more and 75 or less amino acids, furthermore preferably 1 or more and 60 or less amino acids, furthermore preferably 1 or more and 45 or less amino acids, furthermore preferably 1 or more and 30 or less amino acids, or furthermore preferably 1 or 15 amino acids, are deleted, substituted, inserted or added to the amino acid sequence of the protein, and having TE activity for medium-chain acyl-ACP.

<35> The transformant or the method of producing the same described in any one of the above items <29> to <34>, wherein expression of a gene encoding a KAS is enhanced.

<36> The transformant or the method of producing the same described in the above item <35>, wherein the KAS is a KAS having medium-chain β-ketoacyl-ACP synthase activity.

<37> The transformant or the method of producing the same described in the above item <35> or <36>, wherein the KAS is a protein consisting of the amino acid sequence set forth in SEQ ID NO: 48, SEQ ID NO: 75, SEQ ID NO: 67, SEQ ID NO: 69, SEQ ID NO: 71, SEQ ID NO: 73, SEQ ID NO: 77, SEQ ID NO: 79, or SEQ ID NO: 81; a protein consisting of an amino acid sequence having 50% or more, preferably 60% or more, preferably 65% or more, more preferably 70% or more, more preferably 75% or more, more preferably 80% or more, more preferably 85% or more, more preferably 90% or more, and further preferably 95% or more identity with the amino acid sequence of the protein, and having medium-chain β-ketoacyl-ACP synthase activity; or a protein consisting of an amino acid sequence in which 1 or several amino acids, preferably 1 or more and 255 or less amino acids, more preferably 1 or more and 204 or less amino acids, further preferably 1 or more and 179 or less amino acids, furthermore preferably 1 or more and 153 or less amino acids, furthermore preferably 1 or more and 128 or less amino acids, furthermore preferably 1 or more and 102 or less amino acids, furthermore preferably 1 or more and 77 or less amino acids, furthermore preferably 1 or more and 51 or less amino acids, or furthermore preferably 1 or 26 amino acids, are deleted, substituted, inserted or added to the amino acid sequence of the protein, and having medium-chain β-ketoacyl-ACP synthase activity.

<38> The transformant or the method of producing the same described in any one of the above items <29> to <37>, wherein the transformant or the host is a microorganism or a plant.

<39> The transformant or the method of producing the same described in the above item <38>, wherein the microorganism is a microalga.

<40> The transformant or the method of producing the same described in the above item <39>, wherein the microalga is an alga belonging to the genus *Nannochloropsis*, more preferably *Nannochloropsis oculata*.

<41> The transformant or the method of producing the same described in the above item <38>, wherein the microorganism is *Escherichia coli*.

<42> The transformant or the method of producing the same described in the above item <38>, wherein the plant is *Arabidopsis thaliana*.

<43> Use of the protein, the gene, the recombinant vector, the transformant or a transformant obtained by the method of producing a transformant described in any one of the above items <25> to <42>, for producing lipids.

<44> The use described in the above item <43>, wherein the lipids contain a medium-chain fatty acid or an ester compound thereof, preferably a fatty acid having 6 or more and 14 or less carbon atoms or an ester compound thereof, more preferably a fatty acid having 8 or more and 14 or less carbon atoms or an ester compound thereof, more preferably a fatty acid having 10 or more and 14 or less carbon atoms or an ester compound thereof, more preferably a fatty acid having 12 or more and 14 or less carbon atoms or an ester compound thereof, more preferably a fatty acid having 12 or 14 carbon atoms or an ester compound thereof, more preferably a saturated fatty acid having 12 or 14 carbon atoms (lauric acid or myristic acid) or an ester compound thereof.

EXAMPLES

Hereinafter, the present invention will be described more in detail with reference to Examples, but the present invention is not limited thereto. Herein, the nucleotide sequences of the primers used in Examples are shown in Table 1.

TABLE 1

| Primer No. | Nucleotide sequence (5' → 3') | SEQ ID NO: |
|---|---|---|
| 5 | tcttttttgtgaagcatgattgaacaaga tggatt | SEQ ID NO: 5 |
| 6 | tttccccatcccgatcagaagaactcgt caagaa | SEQ ID NO: 6 |
| 7 | cgagctcggtacccgactgcgcatggatt gaccga | SEQ ID NO: 7 |
| 8 | atatcaagaagctgtctttt | SEQ ID NO: 8 |
| 9 | tcgggatgggggaaaaaaacctctg | SEQ ID NO: 9 |
| 10 | actctagaggatcccctttcgtaaataaa tcagctc | SEQ ID NO: 10 |
| 12 | gggatcctctagagtcgacctgcaggcat gcaagc | SEQ ID NO: 12 |
| 13 | cgggtaccgagctcgaattc | SEQ ID NO: 13 |
| 14 | cagcccgcatcaacaatgacccaaccacc cagcac | SEQ ID NO: 14 |
| 15 | ctcttccacagaagctcacaggtcattta ccaaag | SEQ ID NO: 15 |
| 16 | cgagctcggtacccgttcttccgcttgtt gctgcc | SEQ ID NO: 16 |
| 17 | tgttgatgcgggctgagattggtgg | SEQ ID NO: 17 |
| 20 | gcttctgtggaagagccagtg | SEQ ID NO: 20 |
| 21 | caatccatgcgcagtctgatcttgtccat ctcgtg | SEQ ID NO: 21 |
| 22 | actgcgcatggattgaccga | SEQ ID NO: 22 |
| 24 | tcttttttgtgaagctatggccaagctga ccagcgc | SEQ ID NO: 24 |
| 25 | tttccccatcccgattagtcctgctcct cggccac | SEQ ID NO: 25 |
| 27 | cgcggtgttgcgcgctggaagccgaagcc gaagct | SEQ ID NO: 27 |
| 28 | ctcttccacagaagcttacaccctcggtt ctgcgg | SEQ ID NO: 28 |
| 32 | cgagctcggtacccgggcggtctttgtc cttcctc | SEQ ID NO: 32 |
| 33 | aatctgctcggaggggaggatc | SEQ ID NO: 33 |
| 34 | ccctccgagcagattatgaagaccgccgc tctcctc | SEQ ID NO: 34 |
| 35 | gcgcgcaacaccgcgggtgcgggagaac | SEQ ID NO: 35 |
| 36 | gcggccgctctagagtgcgagacggccca cgccgggac | SEQ ID NO: 36 |
| 37 | acaaaatattaacgcctagctaatatcaa ttttctttgg | SEQ ID NO: 37 |
| 40 | ctctagagcggccgccaccg | SEQ ID NO: 40 |
| 41 | gcgttaatattttgttaaaattcg | SEQ ID NO: 41 |
| 42 | ctggacaataccatgggatgggccttttt cgccgccaag | SEQ ID NO: 42 |

TABLE 1-continued

| Primer No. | Nucleotide sequence (5' → 3') | SEQ ID NO: |
|---|---|---|
| 43 | catggtattgtccagcaaag | SEQ ID NO: 43 |
| 46 | tcttttttgtgaagcatggtcgagattcgaagcat | SEQ ID NO: 46 |
| 47 | tttcccccatcccgatcagaagaactcgtccaaca | SEQ ID NO: 47 |
| 50 | aaatcatacagcaggatgcgggtctccagtagcgc | SEQ ID NO: 50 |
| 51 | ctcttccacagaagcttacttgaacggtttgaag | SEQ ID NO: 51 |
| 53 | cgagctcggtacccggctgctgccccgaccgtatc | SEQ ID NO: 53 |
| 54 | cctgctgtatgattttggcac | SEQ ID NO: 54 |
| 56 | cagcccgcatcaacaatgtctgctgctgctgatag | SEQ ID NO: 56 |
| 57 | ctcttccacagaagcctaatcttcatgtagatcta | SEQ ID NO: 57 |

Example 1 Production of a Transformant in which a NoG3PDH Gene is Introduced into *Nannochloropsis oculata*, and Production of Fatty Acids Using the Transformant (1) Construction of Plasmid for Neomycin Resistance Gene Expression A neomycin resistance gene (SEQ ID NO: 3), and a tubulin promoter sequence (SEQ ID NO: 4) derived from *Nannochloropsis gaditana* strain CCMP 526 described in a literature (Randor Radakovits, et al., Nature Communications, DOI:10.1038/ncomms1688, 2012) were artificially synthesized.

Using the thus-synthesized DNA fragments as a template, and a pair of the primer Nos. 5 and 6, and a pair of the primer Nos. 7 and 8 shown in Table 1, PCRs were carried out, to amplify the neomycin resistance gene and the tubulin promoter sequence, respectively.

Further, using a genome of *Nannochloropsis oculata* strain NIES-2145 as a template, and a pair of the primer Nos. 9 and 10 shown in Table 1, PCR was carried out to amplify the heat shock protein terminator sequence (SEQ ID NO: 11).

Furthermore, using a plasmid vector pUC19 (manufactured by Takara Bio) as a template, and a pair of the primer Nos. 12 and 13 shown in Table 1, PCR was carried out to amplify the plasmid vector pUC19.

These four amplified fragments were treated by restriction enzyme DpnI (manufactured by TOYOBO) respectively, and were purified using a High Pure PCR Product Purification Kit (manufactured by Roche Applied Science). Then, obtained four fragments were fused using an In-Fusion HD Cloning Kit (manufactured by Clontech) to construct a plasmid for neomycin resistance gene expression.

Herein, the expression plasmid consisted of the pUC19 vector sequence and an insert sequence in which the tubulin promoter sequence, the neomycin resistance gene and the heat shock protein terminator sequence were linked in this order.

(2) Construction of Plasmid for NoG3PDH Gene Expression

*Nannochloropsis oculata* strain NIES-2145 was obtained from National Institute for Environmental Studies (NIES) so as to be used. *Nannochloropsis oculata* strain NIES-2145 was fully cultured in f/2 liquid medium (75 mg of $NaNO_3$, 6 mg of $NaH_2PO_4.2H_2O$, 0.5 μg of vitamin B12, 0.5 μg of biotin, 100 μg of thiamine, 10 mg of $Na_2SiO_3.9H_2O$, 4.4 mg of $Na_2EDTA.2H_2O$, 3.16 mg of $FeCl_3.6H_2O$, 12 μg of $FeCl_3.6H_2O$, 21 μg of $ZnSO_4.7H_2O$, 180 μg of $MnCl_2.4H_2O$, 7 μg of $CuSO_4.5H_2O$, 7 μg of $Na_2MoO_4.2H_2O$/ artificial sea water 1 L), and then, the resultant was inoculated in 50 mL of f/2 medium so as to be 10% of the resultant in the f/2 medium, and cultured for six days at 25° C. under an atmosphere of 0.3% $CO_2$. After culturing, collected samples were crushed by using Multi-beads shocker, and then RNA purification was conducted using RNeasy Plant Mini Kit (manufactured by Qiagen). The cDNA library was prepared by thus-obtained total RNA, using SuperScript III First-Strand Synthesis System for RT-PCR (manufactured by invitrogen). PCR using a pair of the primer Nos. 14 and 15 shown in Table 1 and the above cDNA as a template, was carried out to prepare a NoG3PDH gene fragment.

Further, using a genome of *Nannochloropsis oculata* strain NIES-2145 as a template, and a pair of the primer Nos. 16 and 17 shown in Table 1, PCR was carried out to amplify the LDSP promoter sequence (SEQ ID NO: 18).

Furthermore, a VCP1 terminator sequence (SEQ ID NO: 19) was artificially synthesized based on the complete cds sequence (Accession number: JF957601.1) of the VCP1 (violaxanthin/(chlorophyll a)-binding protein) gene of *Nannochloropsis* sp. strain W2J3B registered in GenBank. Using the thus-synthesized DNA fragments as a template, and a pair of the primer Nos. 20 and 21 shown in Table 1, PCR was carried out to prepare the VCP1 terminator sequence.

Furthermore, using the above-described plasmid for neomycin resistance gene expression as a template, and a pair of the primer Nos. 22 and 13 shown in Table 1, PCR was carried out to amplify a fragment containing the cassette for neomycin resistance gene expression (the tubulin promoter sequence, the neomycin resistance gene, and the heat shock protein terminator sequence) and the pUC19 vector sequence.

These four fragments were fused by a method in a manner similar to described above, to construct plasmids for NoG3PDH gene expression.

Herein, the expression plasmid consisted of the pUC19 vector sequence and an insert sequence in which the LDSP promoter sequence, the NoG3PDH gene, the VCP1 terminator sequence, the tubulin promoter sequence, the neomycin resistance gene and the heat shock protein terminator sequence were linked in this order.

(3) Introduction of a Fragment for NoG3PDH Gene Expression into *Nannochloropsis*

Using the above-described plasmid for the NoG3PDH gene expression as a template, and a pair of the primer Nos. 16 and 10 shown in Table 1, PCR was carried out to amplify the fragment for NoG3PDH gene expression (a DNA fragment containing the LDSP promoter sequence, the NoG3PDH gene, the VCP1 terminator sequence, the tubulin promoter sequence, the neomycin resistance gene, and the heat shock protein terminator sequence).

The amplified DNA fragment was purified using High Pure PCR Product Purification Kit (manufactured by Roche Applied Science). Herein, sterilized water was used for elution upon purification without using an elution buffer included in the kit.

About $1\times10^9$ cells of *Nannochloropsis oculata* strain NIES-2145 (obtained from National Institute for Environmental Studies (NIES)) were washed with 384 mM sorbitol solution to completely remove a salt, and the resultant was used as a host cell for transformation. The fragment for NoG3PDH gene expression as amplified above was mixed by about 500 ng with the host cell, and electroporation was carried out under the conditions of 50 µF, 500Ω and 2,200 v/2 mm.

After one day recovery cultivation in f/2 liquid medium (75 mg of $NaNO_3$, 6 mg of $NaH_2PO_4.2H_2O$, 0.5 µg of vitamin B12, 0.5 µg of biotin, 100 µg of thiamine, 10 mg of $Na_2SiO_3.9H_2O$, 4.4 mg of $Na_2EDTA.2H_2O$, 3.16 mg of $FeCl_3.6H_2O$, 12 µg of $FeCl_3.6H_2O$, 21 µg of $ZnSO_4.7H_2O$, 180 µg of $MnCl_2.4H_2O$, 7 µg of $CuSO_4.5H_2O$, 7 µg of $Na_2MoO_4.2H_2O$/artificial sea water 1 L), the resultant was inoculated in f/2 agar medium containing 500 µg/mL of neomycin, and cultured for two to three weeks under 12 h/12 h light-dark conditions at 25° C. under an atmosphere of 0.3% $CO_2$. Obtained colonies were selected as the transgenic strain (G3PDH).

(4) Production of Fatty Acids Using the Transformant

The selected strain was inoculated to 50 mL of medium in which a nitrogen concentration in the f/2 medium was reinforced 15 times, and a phosphorus concentration therein was reinforced 5 times (hereinafter, referred to as "N15P5 medium"), and subjected to shaking culture for four weeks under the 12 h/12 h light-dark conditions at 25° C. under the atmosphere of 0.3% $CO_2$, to prepare preculture fluid. Then, 10 mL of the preculture fluid was inoculated to 40 mL of the N15P5 medium, and subjected to shaking culture under the 12 h/12 h light-dark conditions at 25° C. under the atmosphere of 0.3% $CO_2$. After three weeks cultivation, lipid components contained in the culture fluid were analyzed by the method described below.

In addition, as a negative control, an experiment was also conducted on the transformant (WT), in which only neomycin resistance gene was introduced into the host cell.

(5) Extraction of Lipids and Analysis of Fatty Acids Contained Therein

To 1 mL of the culture fluid, 50 µL of 1 mg/mL 7-pentadecanone as an internal standard was added, and then 0.5 mL of chloroform, 1 mL of methanol and 10 µL of 2N hydrochloric acid were further added. The mixture was vigorously stirred and then was left for 30 minutes. Further, 0.5 mL of chloroform and 0.5 mL of 1.5% KCl were added thereto. The mixture was stirred and centrifuged for 15 minutes at 3,000 rpm, and then the chloroform layer (lower layer) was collected with Pasteur pipette.

A nitrogen gas was blown onto the resultant chloroform layer to be dried into solid. Then, 0.7 mL of 0.5 N potassium hydroxide/methanol solution was added to the sample, and the mixture was kept warm at 80° C. for 30 minutes. Next, 1 mL of 14% boron trifluoride-methanol solution (manufactured by Sigma-Aldrich) was added to the sample, and the mixture was kept warm at 80° C. for 10 minutes. Thereafter, 1 mL of hexane and 1 mL of saturated saline were added thereto, and the mixture was vigorously stirred and then was left for 30 minutes at room temperature. Then, the hexane layer was collected to obtain fatty acid methyl esters.

Under the measuring conditions as follows, the obtained fatty acid methyl esters were provided for gas chromatographic analysis.

<Gas Chromatography Conditions>

Capillary column: DB-1 MS (30 m×200 µm×0.25 µm, manufactured by J & W Scientific)
Mobile phase: high purity helium
Flow rate in column: 1.0 mL/minute
Elevated temperature program: 100° C. (1 minute)→10° C./minute→300° C. (5 minutes)
Equilibrating time: 1 minute
Injection port: split injection (split ratio: 100:1), pressure: 14.49 psi, 104 mL/minute
Amount of injection: 1 µL
Cleaning vial: methanol/chloroform
Detector temperature: 300° C.

Moreover, the fatty acid methyl esters were identified by providing the identical sample under identical conditions described above.

Amounts of the fatty acid methyl esters of each of the fatty acids were quantitatively determined based on the peak areas of waveform data obtained by the above gas chromatographic analysis. The peak area corresponding to each of the fatty acid methyl esters was compared with that of 7-pentadecanone as the internal standard, and carried out corrections between the samples, and then the amount of each of the fatty acids per liter of the culture fluid was calculated. Further, the total amount of the fatty acids (FA) was calculated by summing the amounts of each of the fatty acids thus obtained, and ratio of each of the fatty acids in the total amount of the fatty acids was calculated.

Table 2 shows the results. Herein, in Table below, "Fatty Acid Composition (% TFA)" presents a ratio of a weight of each fatty acid relative to a weight of the total fatty acid (weight percent). Herein, "n" designates an integer of 0 to 5. For example, when "C18:n" is described, the description means a total of each fatty acid having compositions of C18:0, C18:1, C18:2, C18:3, C18:4 and C18:5.

TABLE 2

| | Fatty acid composition (% TFA) | | | | | | (n = 3) FA |
|---|---|---|---|---|---|---|---|
| | C12:0 | C14:0 | C16:1 | C16:0 | C18:n | C20:n | (mg/L) |
| WT | 0.2 ± 0.1 | 5.9 ± 0.5 | 31.8 ± 0.3 | 33.5 ± 0.1 | 19.9 ± 0.3 | 8.7 ± 0.3 | 3655.8 ± 233.9 |
| G3PDH | 0.4 ± 0.0 | 10.7 ± 0.3 | 28.7 ± 0.4 | 29.2 ± 0.9 | 21.3 ± 0.3 | 9.7 ± 0.5 | 3818.5 ± 242.9 |

As shown in Table 2, it was confirmed that the ratios of lauric acid (C12:0) and myristic acid (C14:0) were significantly increased and the total amount of all fatty acids tended to be increased, by introducing the NoG3PDH gene.

Example 2 Production of a Transformant in which a BTE Gene and a NoG3PDH Gene are Introduced into *Nannochloropsis oculata*, and Production of Fatty Acids Using the Transformant (1) Construction of Plasmid for Zeocin Resistance Gene Expression Zeocin resistance gene fragment was amplified by carrying out PCR by using the DNA fragment of the zeocin resistance gene (SEQ ID NO: 23) artificially synthesized as a template, and a pair of the primer Nos. 24 and 25 shown in Table 1.

Using the plasmid for neomycin resistance gene expression constructed in Example 1 as a template, and a pair of the primer Nos. 9 and 8 shown in Table 1, PCR was carried out to amplify the DNA fragment containing the heat shock protein terminator sequence, pUC19 vector sequence, and the tubulin promoter sequence.

Obtained DNA fragments were fused by a method in a manner similar to that described in Example 1, to construct a plasmid for zeocin resistance gene expression.

Herein, the expression plasmid consisted of the pUC19 vector sequence and an insert sequence in which the tubulin promoter sequence, the zeocin resistance gene, and the heat shock protein terminator sequence were linked in this order.

(2) Construction of Plasmid for BTE Gene Expression

The nucleotide sequence (SEQ ID NO: 26) encoding the BTE which is described in WO 92/20236 was artificially synthesized. Using the thus-synthesized DNA fragment as a template, and a pair of the primer Nos. 27 and 28 shown in Table 1, PCR was carried out, to prepare the BTE gene fragment. Note that, in the DNA fragment, the segment corresponding to the chloroplast transit signal (85 amino acids of the N-terminal) of BTE (SEQ ID NO: 29) was deleted.

Further, a VCP1 promoter sequence (SEQ ID NO: 30), a VCP1 chloroplast transit signal sequence (SEQ ID NO: 31) and a VCP1 terminator sequence (SEQ ID NO: 19) were artificially synthesized based on the complete cds sequence (Accession number: JF957601.1) of the VCP1 (violaxanthin/(chlorophyll a)-binding protein) gene of *Nannochioropsis* sp. strain W2J3B registered in GenBank. Using the thus-synthesized DNA fragments as a template, and a pair of the primer Nos. 32 and 33, a pair of the primer Nos. 34 and 35, and a pair of the primer Nos. 20 and 21 shown in Table 1, PCRs were carried out, to prepare the VCP1 promoter sequence, VCP1 chloroplast transit signal sequence, and VCP1 terminator sequence, respectively.

Furthermore, using the above-described plasmid for zeocin resistance gene expression as a template, and a pair of the primer Nos. 22 and 13 shown in Table 1, PCR was carried out to amplify a DNA fragment containing the tubulin promoter sequence, the zeocin resistance gene, the heat shock protein terminator sequence, and the pUC19 vector sequence.

DNA fragments obtained by the method described above, were fused by a method in a manner similar to that described in Example 1, to construct a plasmid for BTE gene expression.

Herein, the expression plasmid consisted of the pUC19 vector sequence and an insert sequence in which the VCP1 promoter sequence, the VCP1 chloroplast transit signal sequence, the BTE gene fragment, the VCP1 terminator sequence, the tubulin promoter sequence, the zeocin resistance gene, and the heat shock protein terminator sequence were linked in this order.

(3) Introduction of a BTE Gene and a NoG3PDH Gene into *Nannochloropsis oculata*

Using the above-described plasmid for the BTE gene expression as a template, and a pair of the primer Nos. 32 and 10 shown in Table 1, PCR was carried out to amplify the fragment for BTE gene expression (a DNA fragment containing the VCP1 promoter sequence, the VCP1 chloroplast transit signal sequence, the BTE gene, the VCP1 terminator sequence, the tubulin promoter sequence, the zeocin resistance gene, and the heat shock protein terminator sequence).

The amplified DNA fragment was purified using High Pure PCR Product Purification Kit (manufactured by Roche Applied Science). Herein, sterilized water was used for elution upon purification without using an elution buffer included in the kit.

The BTE gene was introduced into *Nannochloropsis oculata* strain NIES-2145 according to the same method as in Example 1. Then the resultant was cultured in zeocin-containing f/2 medium. Obtained colonies were selected as the BTE gene transgenic strain (BTE).

Further, using the BTE gene transgenic strain as a host, the NoG3PDH gene was introduced according to the same method as in Example 1 Obtained colonies were selected as the BTE and NoG3PDH genes transgenic strain (BTE+NoG3PDH).

(4) Production of Fatty Acids Using the Transformant

The selected strains were inoculated to 50 mL of the N15P5 medium, and subjected to shaking culture for four weeks under the 12 h/12 h light-dark conditions at 25° C. under the atmosphere of 0.3% $CO_2$, to prepare preculture fluid. Then, 10 mL of the preculture fluid was inoculated to 40 mL of N15P5 medium, and subjected to shaking culture under the 12 h/12 h light-dark conditions at 25° C. under the atmosphere of 0.3% $CO_2$.

After three weeks cultivation, lipid components contained in the culture fluid were analyzed by the method described in Example 1. Table 3 shows the results.

TABLE 3

| | Fatty acid composition (% TFA) | | | | | | (n = 3) FA |
|---|---|---|---|---|---|---|---|
| | C12:0 | C14:0 | C16:1 | C16:0 | C18:n | C20:n | (mg/L) |
| BTE | 5.5 ± 0.0 | 6.1 ± 0.0 | 25.9 ± 0.6 | 26.3 ± 0.4 | 14.5 ± 0.7 | 21.7 ± 1.5 | 2298.6 ± 177.9 |
| BTE + NoG3PDH | 13.4 ± 0.7 | 8.2 ± 0.2 | 21.9 ± 0.4 | 22.2 ± 0.3 | 14.3 ± 0.2 | 20.0 ± 0.1 | 2381.6 ± 198.4 |

As shown in Table 3, it was confirmed that the ratios of lauric acid (C12:0) and myristic acid (C14:0) were significantly increased and the total amount of all fatty acids tended to be increased, by introducing the NoG3PDH gene into the strain into which the BTE gene has been introduced.

Example 3 Production of a Transformant in which a Modified NoTE Gene and a NoG3PDH Gene are Introduced into *Nannochloropsis oculata*, and Production of Fatty Acids Using the Transformant (1) Obtaining of a NoTE Gene and Construction of Plasmid for NoTE Gene Expression Using the cDNA of *Nannochloropsis oculata* strain NIES-2145 prepared in Example 1 as a template, and a pair of the primer Nos. 36 and 37 shown in Table 1, PCR was carried out to prepare the gene fragments consisting of the nucleotide sequence of the 262nd to 864th positions set forth in SEQ ID NO: 39.

Further, using the plasmid vector of pBluescriptII SK(-) (manufactured by Stratagene) as a template, and a pair of the primer Nos. 40 and 41 shown in Table 1, PCR was carried out to amplify the pBluescriptII SK(-), then the template was digested by restriction enzyme DpnI (manufactured by TOYOBO).

These two fragments were purified using a High Pure PCR Product Purification Kit (manufactured by Roche Applied Science). Then, the obtained two fragments were fused using an In-Fusion HD Cloning Kit (manufactured by Clontech) to construct a plasmid NoTE_262 for NoTE gene expression. This plasmid NoTE_262 was constructed for expression of a protein in the form of removing amino acid residues of the 1st to 87th positions on an N-terminal side of the amino acid sequence set forth in SEQ ID NO: 38, and fusing, to the upstream of the removed terminus, amino acid residues of the 1st to 29th positions on an N-terminal side of a LacZ protein derived from the plasmid vector pBluescriptII SK(-).

In the following plasmid notation, "NoTE_262" means that a plasmid had the nucleotide sequence of the 262nd to 864th positions set forth in SEQ ID NO: 39 as a nucleotide sequence encoding a polypeptide consisting of the amino acid sequence of the 88th to 287th positions set forth in SEQ ID NO: 38.

PCR was carried out by using the plasmid NoTE_262 as a template, and a pair of the primer Nos. 42 and 43 shown in Table 1, to obtain gene fragments (SEQ ID NO: 44) in which a part of nucleotides of the 262nd to 864th positions of the nucleotide sequence set forth in SEQ ID NO: 39 was subjected to mutation. The plasmids for modified NoTE expression NoTE_262 (V204W), was constructed by using the gene fragment according to a technique in a manner similar to the above-described manner. Herein, the nucleotide sequence set forth in SEQ ID NO: 44 is the nucleotide sequence wherein a codon encoding the valine of the 204th position of the amino acid sequence set forth in SEQ ID NO: 38 was substituted with a codon encoding tryptophan (TGG).

Using the plasmid NoTE_262 (V204W) as a template, and a pair of the primer Nos. 41 and 42 shown in Table 1, PCR was carried out to prepare a modified NoTE gene fragment consisting of the nucleotide sequence set forth in SEQ ID NO: 44.

According to the same method as in Example 2, the VCP1 promoter sequence, the VCP1 chloroplast transit sequence, and the VCP1 terminator sequence were prepared, respectively.

Further, according to the same method as in Example 1, the plasmid vector pUC19 was amplified.

The modified NoTE gene fragment, the VCP1 promoter sequence, the VCP1 chloroplast transit signal sequence, and the VCP1 terminator sequence were fused with plasmid vector pUC19 by a method in a manner similar to that described in Example 1, to construct a plasmid NoTE_262 (V204W)_Nanno for modified NoTE gene expression. Herein, the expression plasmid consisted of the pUC19 vector sequence and a sequence for NoTE gene expression in which the VCP1 promoter sequence, the VCP1 chloroplast transit signal sequence, the modified NoTE gene fragment, and the VCP1 terminator sequence were linked in this order.

Using the plasmid NoTE_262 (V204W)_Nanno as a template, and a pair of the primer Nos. 32 and 21 shown in Table 1, PCR was carried out to prepare a gene fragment consisted of the VCP1 promoter sequence, the VCP1 chloroplast transit signal sequence, the modified NoTE gene, and the VCP1 terminator sequence.

Further, the plasmid for zeocin resistance gene expression constructed in Example 2 as a template, and a pair of the primer Nos. 22 and 13 shown in Table 1, PCR was carried out to amplify a gene fragment consisted of the tubulin promoter sequence, the zeocin resistance gene, the heat shock protein terminator sequence, and the pUC19 vector sequence.

The obtained gene fragments were fused by a method in a manner similar to that described in Example 1, to construct a plasmid for modified NoTE gene expression.

Herein, the expression plasmid consisted of the pUC19 vector sequence and an insert sequence in which the VCP1 promoter sequence, the VCP1 chloroplast transit signal sequence, the modified NoTE gene fragment, the VCP1 terminator sequence, the tubulin promoter sequence, the zeocin resistance gene, and the heat shock protein terminator sequence were linked in this order.

(3) Introduction of a Modified NoTE Gene and a NoG3PDH Gene into *Nannochloropsis oculata*

Using the above-described plasmid for the modified NoTE gene expression as a template, and a pair of the primer Nos. 32 and 10 shown in Table 1, PCR was carried out to amplify the fragment for modified NoTE gene expression (a DNA fragment consisted of the VCP1 promoter sequence, the VCP1 chloroplast transit signal sequence, the modified NoTE gene, the VCP1 terminator sequence, the tubulin promoter sequence, the zeocin resistance gene, and the heat shock protein terminator sequence).

The amplified gene fragment was purified using High Pure PCR Product Purification Kit (manufactured by Roche Applied Science). Herein, sterilized water was used for elution upon purification without using an elution buffer included in the kit.

The modified NoTE gene was introduced into *Nannochloropsis oculata* strain NIES-2145 according to the same method as in Example 1. Then the resultant was cultured in zeocin-containing f/2 medium. Obtained colonies were selected as the modified NoTE gene transgenic strain (NoTE).

Further, using the modified NoTE gene transgenic strain as a host, the NoG3PDH gene was introduced according to the same method as in Example 1. Obtained colonies were selected as the modified NoTE and NoG3PDH genes transgenic strain (NoTE+NoG3PDH).

(4) Production of Fatty Acids Using the Transformant

The selected strains were inoculated to 50 mL of the N15P5 medium, and subjected to shaking culture for four weeks under the 12 h/12 h light-dark conditions at 25° C. under the atmosphere of 0.3% $CO_2$, to prepare preculture fluid. Then, 10 mL of the preculture fluid was inoculated to 40 mL of N15P5 medium, and subjected to shaking culture under the 12 h/12 h light-dark conditions at 25° C. under the atmosphere of 0.3% $CO_2$.

After three weeks cultivation, lipid components contained in the culture fluid were analyzed by the method described in Example 1. Table 4 shows the results.

TABLE 4

| | Fatty acid composition (% TFA) | | | | | | (n = 3) FA |
|---|---|---|---|---|---|---|---|
| | C12:0 | C14:0 | C16:1 | C16:0 | C18:n | C20:n | (mg/L) |
| NoTE | 6.8 ± 0.1 | 13.1 ± 0.2 | 28.9 ± 0.7 | 22.0 ± 1.0 | 14.5 ± 0.2 | 14.8 ± 1.0 | 3658.1 ± 208.2 |
| NoTE + G3PDH | 10.3 ± 0.5 | 17.8 ± 0.6 | 24.6 ± 0.7 | 15.7 ± 2.0 | 14.9 ± 0.9 | 16.7 ± 3.0 | 3849.0 ± 131.6 |

As shown in Table 4, it was confirmed that the ratios of lauric acid (C12:0) and myristic acid (C14:0) were significantly increased and the total amount of all fatty acids tended to be increased, by introducing the NoG3PDH gene into the strain into which the modified NoTE gene was introduced.

Example 4 Production of a Transformant in which a BTE Gene, a NoKAS IV Gene, and NoG3PDH are Introduced into *Nannochloropsis oculata*, and Production of Fatty Acids Using the Transformant (1) Construction of Plasmid for Paromomycin Resistance Gene Expression Using the DNA fragment of the paromomycin resistance gene (SEQ ID NO: 45) artificially synthesized as a template, and a pair of the primer Nos. 46 and 47 shown in Table 1, PCR was carried out to amplify the paromomycin resistance gene.

Further, using the plasmid of neomycin resistance gene constructed in Example 1 as a template, and a pair of the primer Nos. 9 and 8 shown in Table 1, PCR was carried out to amplify a DNA fragment containing the heat shock protein terminator sequence, the pUC19 vector sequence, and the tubulin promoter sequence.

The obtained DNA fragments were fused by a method in a manner similar to that described in Example 1, to construct a plasmid for paromomycin resistance gene expression.

Herein, the expression plasmid consisted of the pUC19 vector sequence and an insert sequence in which the tubulin promoter sequence, the paromomycin resistance gene, and the heat shock protein terminator sequence were linked in this order.

(2) Obtaining of a NoKAS IV, Gene and Construction of Plasmid for NoKAS IV Gene Expression Using the cDNA of *Nannochloropsis oculata* strain NIES-2145 prepared in Example 1 as a template, and a pair of the primer Nos. 50 and 51 shown in Table 1, PCR was carried out to prepare the NoKAS IV gene fragment set forth in SEQ ID NO: 49.

Next, ubiquitin promoter sequence (SEQ ID NO: 52) derived from *Nannochloropsis gaditana* strain CCMP 526 described in Randor Radakovits, et al., Nature Communications, DOI:10.1038/ncomms1688, 2012 was artificially synthesized.

Further, using the DNA fragment of the VCP1 terminator sequence artificially synthesized by a method in a manner similar to that described above as a template, and a pair of the primer Nos. 20 and 21 shown in Table 1, PCR was carried out, to prepare the VCP1 terminator sequence.

Furthermore, using the above-described plasmid for paromomycin resistance gene expression as a template, and a pair of the primer Nos. 22 and 13 shown in Table 1, PCR was carried out to amplify a DNA fragment containing the tubulin promoter sequence, the paromomycin resistance gene, the heat shock protein terminator sequence, and the pUC19 vector sequence.

The obtained four prepared fragments were fused by a method in a manner similar to that described in Example 1, to construct a plasmid for NoKAS IV gene expression.

Herein, the expression plasmid consisted of the pUC19 vector sequence and an insert sequence in which the ubiquitin promoter sequence, the NoKAS IV gene fragment, the tubulin promoter sequence, the paromomycin resistance gene and the heat shock protein terminator sequence were linked in this order.

(3) Introduction of a BTE Gene, a NoKAS IV Gene, and a NoG3PDH Gene into *Nannochloropsis oculata*

Using the above-described plasmid for the NoKAS IV gene expression as a template, and a pair of the primer Nos. 53 and 10 shown in Table 1, PCR was carried out to amplify the fragment for NoKAS IV gene expression (a DNA fragment containing the ubiquitin promoter sequence, the NoKAS IV gene, the VCP1 terminator sequence, the tubulin promoter sequence, the paromomycin resistance gene, and the heat shock protein terminator sequence).

The amplified DNA fragment was purified using High Pure PCR Product Purification Kit (manufactured by Roche Applied Science). Herein, sterilized water was used for elution upon purification without using an elution buffer included in the kit.

Using the BTE gene transgenic strain (BTE) prepared in Example 2 as a host, the NoKAS IV gene was introduced according to the same method as in Example 1. Then the resultant was cultured in paromomycin-containing f/2 medium. Obtained colonies were selected as the BTE and NoKAS IV genes transgenic strain (BTE+NoKAS IV).

Further, using the BTE and NoKAS IV genes transgenic strain (BTE+NoKAS IV) as a host, the NoG3PDH gene was introduced according to the same method as in Example 1 Then the resultant was cultured in neomycin-containing f/2 medium. Obtained colonies were selected as the BTE, NoKAS IV, and NoG3PDH genes transgenic strain (NoTE+ NoG3PDH+NoG3PDH).

(4) Production of Fatty Acids Using the Transformant

The selected strains were inoculated to 50 mL of the N15P5 medium, and subjected to shaking culture for four weeks under the 12 h/12 h light-dark conditions at 25° C. under the atmosphere of 0.3% $CO_2$, to prepare preculture fluid. Then, 10 mL of the preculture fluid was inoculated to 40 mL of N15P5 medium, and subjected to shaking culture under the 12 h/12 h light-dark conditions at 25° C. under the atmosphere of 0.3% $CO_2$.

After three weeks cultivation, lipid components contained in the culture fluid were analyzed by the method described in Example 1. Table 5 shows the results.

TABLE 5

| | Fatty acid composition (% TFA) | | | | | | FA (n = 3) |
|---|---|---|---|---|---|---|---|
| | C12:0 | C14:0 | C16:1 | C16:0 | C18:n | C20:n | (mg/L) |
| BTE + KAS IV | 8.5 ± 0.4 | 7.6 ± 1.2 | 27.2 ± 1.9 | 24.1 ± 1.8 | 14.2 ± 0.8 | 18.4 ± 2.0 | 2750.3 ± 177.3 |
| BTE + KAS IV + G3PDH | 17.5 ± 1.0 | 13.1 ± 0.7 | 22.2 ± 1.2 | 15.4 ± 1.2 | 13.7 ± 1.4 | 18.1 ± 0.3 | 4127.3 ± 240.8 |

As shown in Table 5, it was confirmed that the ratios of lauric acid (C12:0) and myristic acid (C14:0) and the total amount of all fatty acids were significantly increased, by introducing the NoG3PDH gene into the strain into which the BTE gene and the NoKAS IV gene have been introduced.

(5) Fractionation of TAG and Analysis of Fatty Acids Contained in TAG

To 1 mL of the culture fluid, 50 μL of 1 mg/mL triheptadecan (manufactured by Sigma-Aldrich) was added as an internal standard, and then 0.5 mL of chloroform and 1 mL of methanol were added. The mixture was vigorously stirred and then was left for 10 minutes or more. Further, 0.5 mL of chloroform and 0.5 mL of 1.5% KCl were added thereto. The mixture was stirred and centrifuged for 5 minutes at 3,000 rpm, and then the chloroform layer (lower layer) was collected with Pasteur pipette. A nitrogen gas was blown onto the resultant chloroform layer to be dried into solid, and the resultant material was dissolved into 20 μL of chloroform.

A total amount of the thus-obtained lipids extract, and 3 μL of three kinds of standard solutions {trimyristin (manufactured by Wako Pure Chemical Industries, Ltd.), glycerol dioleate (manufactured by Wako Pure Chemical Industries, Ltd.), oleic acid (manufactured by Wako Pure Chemical Industries, Ltd.), and 10 mg/mL chloroform solution} each were spotted onto TLC silica gel 60F$_{254}$ (manufactured by Merck), and the resultant material was developed for about 15 minutes by using TLC developing tank DT-150 (manufactured by Mitsubishi Chemical Medience Corporation) with a developing solvent (hexane:diethyl ether:formic acid=42:28:0.3 (volume ratio)). After development, the plate was dried, 0.1% primulin (manufactured by Wako Pure Chemical Industries, Ltd.) dissolved in methanol was sprayed thereon and dried, and then a TAG fraction was detected by handy type UV lamp UVL-21 (manufactured by SOGO LABORATORY GLASS WORKS CO., LTD.).

The TAG fraction was scratched and collected by using a toothpick and 1 mL of 14% boron trifluoride-methanol solution (manufactured by Sigma-Aldrich) was added thereto, and a temperature of the resultant material was kept constant at 80° C. for 10 minutes. Then, 0.5 mL of hexane and 1 mL of saturated saline were added thereto, and the resultant mixture was vigorously stirred and left to stand for 10 minutes at room temperature, and then, the hexane layer being an upper layer was collected to obtain fatty acid methyl esters.

The obtained fatty acid methyl esters were provided for gas chromatographic analysis by a method in a manner similar to that described above. Table 6 shows the results.

TABLE 6

| | Fatty acid composition (% TFA) | | | | | | TAG (n = 3) |
|---|---|---|---|---|---|---|---|
| | C12:0 | C14:0 | C16:1 | C16:0 | C18:n | C20:n | (mg/L) |
| BTE + KAS IV | 12.9 ± 0.4 | 20.0 ± 0.2 | 20.4 ± 0.1 | 26.5 ± 0.4 | 14.1 ± 0.1 | 6.1 ± 0.0 | 1854.0 ± 81.0 |
| BTE + KAS IV + G3PDH | 22.8 ± 0.7 | 23.7 ± 1.1 | 16.1 ± 0.6 | 18.8 ± 0.4 | 11.6 ± 0.1 | 7.0 ± 0.2 | 2478.7 ± 248.6 |

As shown in Table 6, it was confirmed that the ratios of medium-chain fatty acids (lauric acid (C12:0) and myristic acid (C14:0)) in the TAG, and the total amount of the TAG were significantly increased, by introducing the NoG3PDH gene into the strain into which the BTE gene and NoKAS IV gene have been introduced.

As described above, the transformant in which productivities of the medium-chain fatty acids and the total fatty acids to be produced are improved can be prepared by enhancing the expression of the G3PDH gene as specified in the present invention. Further, productivity of the medium-chain fatty acids and the total amount of all fatty acids to be produced can be improved by culturing this transformant.

Comparative Example 1 Production of a Transformant in which a G3PDH Gene Derived from Yeast is Introduced into *Nannochloropsis oculata*, and Production of Fatty Acids Using the Transformant (1) Construction of Plasmid for Yeast-Derived G3PDH Gene Expression The G3PDH gene derived from yeast (*Saccharomyces cerevisiae*) described in US 2006/0168684 (hereinafter, also referred to as to "YG3PDH gene") (SEQ ID NO: 55) was artificially synthesized. Using the thus-synthesized DNA fragment as a template, and a pair of the primer Nos. 56 and 57 shown in Table 1, PCR was carried out to amplify the yeast G3PDH gene.

Further, using the plasmid for NoG3PDH gene expression constructed in Example 1 as a template, and a pair of the primer Nos. 20 and 17 shown in Table 1, PCR was carried out to amplify the DNA fragment containing the LDSP promoter sequence, the VCP1 terminator sequence, the tubulin promoter sequence, the neomycin resistance gene, the heat shock protein terminator sequence, and pUC19 vector sequence.

DNA fragments, obtained by the method described above, were fused by a method in a manner similar to that described in Example 1, to construct a plasmid for YG3PDH expression.

Herein, the expression plasmid consisted of the pUC19 vector sequence and an insert sequence in which the LDSP promoter sequence, YG3PDH gene, the VCP1 terminator sequence, the tubulin promoter sequence, the neomycin resistance gene and the heat shock protein terminator sequence were linked in this order.

(2) Introduction of a BTE Gene and a Yeast G3PDH Gene into *Nannochioropsis* oculata Using the above-described plasmid for the YG3PDH gene expression as a template, and a pair of the primer Nos. 16 and 10 shown in Table 1, PCR was carried out to amplify the fragment for YG3PDH gene expression (a DNA fragment containing the LDSP promoter sequence, the YG3PDH gene, the VCP1 terminator sequence, the tubulin promoter sequence, the neomycin resistance gene, and the heat shock protein terminator sequence).

The amplified DNA fragment was purified using High Pure PCR Product Purification Kit (manufactured by Roche Applied Science). Herein, sterilized water was used for elution upon purification without using an elution buffer included in the kit.

Using the BTE gene transgenic strain (BTE) constructed in Example 2 as a host, the YG3PDH gene was introduced according to the same method as in Example 1. Then, the resultant was cultured in neomycin-containing f/2 medium. Obtained colonies were selected as the BTE and yeast G3PDH genes transgenic strain (BTE+YG3PDH).

(3) Production of Fatty Acids Using the Transformant

The selected strain was inoculated to 50 mL of the N15P5 medium, and subjected to shaking culture for four weeks under the 12 h/12 h light-dark conditions at 25° C. under the atmosphere of 0.3% $CO_2$, to prepare preculture fluid. Then, 10 mL of the preculture fluid was inoculated to 40 mL of N15P5 medium, and subjected to shaking culture under the 12 h/12 h light-dark conditions at 25° C. under the atmosphere of 0.3% $CO_2$.

After three weeks cultivation, lipid components contained in the culture fluid were analyzed by the method described in Example 1. Table 7 shows the results.

TABLE 7

| | Fatty acid composition (% TFA) | | | | | | (n = 3) FA |
|---|---|---|---|---|---|---|---|
| | C12:0 | C14:0 | C16:1 | C16:0 | C18:n | C20:n | (mg/L) |
| BTE | 5.3 ± 1.1 | 5.2 ± 0.5 | 29.2 ± 1.4 | 33.8 ± 1.4 | 13.8 ± 0.9 | 12.8 ± 2.4 | 1539.9 ± 319.0 |
| BTE + YG3PDH | 1.8 ± 0.6 | 4.9 ± 0.3 | 30.4 ± 0.3 | 36.9 ± 0.6 | 13.5 ± 0.5 | 12.5 ± 0.8 | 1545.0 ± 279.1 |

As shown in Table 7, in the case of introducing the YG3PDH gene, the content of medium-chain fatty acids was decreased and no increase of fats and oils was confirmed, and it was distinct from the present invention.

Note that, the identity of the amino acid sequence of the YG3PDH with the amino acid sequence of NoG3PDH was calculated through use of a homology analysis (homology search) program of genetic information processing software Genetyx-Win. As a result, the identity was 27%.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2015-179166 filed in Japan on Sep. 11, 2015, which is entirely herein incorporated by reference.

What is claimed is:

1. A method of increasing a cells productivity of medium-chain fatty acids, or lipids containing said medium-chain fatty acids, comprising the steps of:
culturing a transformant under conditions suitable for expression of a gene encoding protein (A) or (B), wherein said conditions are also suitable for production of lipids to produce a cultured product or a growth product, and
collecting the medium-chain fatty acids or lipids containing the medium-chain fatty acids from the cultured product or growth product,
wherein the transformant is a migroalga into which a gene encoding protein (A) or (B) has been introduced,
wherein the productivity of medium-chain fatty acids or lipids containing the medium-chain fatty acids is increased in the transformant, as compared to the productivity before introducing the gene encoding protein (A) or (B),
wherein protein (A) and (B) are:
(A) a protein consisting of the amino acid sequence of SEQ ID NO: 1;
(B) a protein consisting of an amino acid sequence having 90% or more identity with the amino acid sequence of SEQ ID NO:1, and having glycerol-3-phosphate dehydrogenase activity.

2. A method of increasing the total amount of fatty acids that are produced by a transformant, comprising the steps of:
culturing a transformant under conditions suitable for expression of a gene encoding protein (A) or (B), wherein said conditions are also suitable for production of fatty acids to produce a cultured product or a growth product, and
collecting the fatty acids from the cultured product or growth product,
wherein the transformant is a migroalga into which a gene encoding protein (A) or (B) has been introduced,
wherein the total amount of fatty acids produced by the transformant is increased as compared to the total amount of fatty acids produced before introducing the gene encoding protein (A) or (B),
wherein protein (A) and (B) are:
(A) a protein consisting of the amino acid sequence of SEQ ID NO: 1;
(B) a protein consisting of an amino acid sequence having 90% or more identity with the amino acid sequence of SEQ ID NO:1, and having glycerol-3-phosphate dehydrogenase activity.

3. The method according to claim 1, wherein expression of a gene encoding an acyl-ACP thioesterase having substrate specificity to a medium-chain acyl-ACP is enhanced in the transformant.

4. The method according to claim 1, wherein expression of a gene encoding a β-ketoacyl-ACP synthase having medium-chain ρ-ketoacyl-ACP synthase activity is enhanced in the transformant.

5. The method according to claim 1, wherein the microalga is an alga belonging to the genus *Nannochloropsis*.

6. The method according to claim 1, wherein the lipids contain a fatty acid having 6-14 carbon atoms or an ester compound thereof.

7. The method according to claim 2, wherein expression of a gene encoding an acyl-ACP thioesterase having substrate specificity to a medium-chain acyl-ACP is enhanced in the transformant.

8. The method according to claim 2, wherein expression of a gene encoding a β-ketoacyl-ACP synthase having medium-chain β-ketoacyl-ACP synthase activity is enhanced in the transformant.

9. The method according to claim 2, wherein the microalga is an alga belonging to the genus *Nannochloropsis*.

10. The method according to claim 2, wherein the lipids contain a fatty acid having 6-14 carbon atoms or an ester compound thereof.

* * * * *

SEQUENCE LISTING

```
<160> NUMBER OF SEQ ID NOS: 82

<210> SEQ ID NO 1
<211> LENGTH: 465
<212> TYPE: PRT
<213> ORGANISM: Nannochloropsis oculata

<400> SEQUENCE: 1

Met Thr Pro Ser Thr Thr Arg Arg Val Asn Ala Ile Thr Leu Pro Gln
1               5                   10                  15
```

-continued

Tyr Ala Thr Phe Thr Leu Gly Phe Leu Ser Leu Val Ala Leu Leu Ser
        20                  25                  30

Trp Met Cys Pro Gln Phe Ile Ser Gln Ala His Ala Ala Thr Ala Phe
        35                  40                  45

Val Gly Gly Ala Gly Ser Gly Ser Phe Gly Ser Arg Ile Ser Arg Gly
50                  55                  60

Thr Arg Arg Thr Gln Gly Gln Thr Thr Met Leu Ala Ser Ala Arg Arg
65                  70                  75                  80

Ser Arg Ser Thr Arg Pro Leu Pro Tyr Pro Val Arg Phe Ala Val Leu
                85                  90                  95

Gly Gly Gly Ser Phe Gly Leu Ala Leu Ala Ser Val Leu Gly Lys Lys
            100                 105                 110

Ser Ile Pro Val Thr Ile Leu Val Arg Lys Glu Asp Val Ala Glu His
            115                 120                 125

Ile Asn Leu His His Arg His Pro Thr Tyr Leu Ser Asp Ile Ser Leu
130                 135                 140

Ala Pro Thr Ile Arg Ala Thr Thr Ile Pro Glu Glu Ala Leu Asn Asp
145                 150                 155                 160

Ala Ser Phe Ile Ile His Ala Val Pro Val Gln Tyr Ser Arg Lys Phe
                165                 170                 175

Leu Glu Asp Ile Ala Pro His Val Pro Lys Asn Thr Pro Ile Ile Ser
            180                 185                 190

Thr Ser Lys Val Ser Tyr Leu Cys Trp Phe Ser Ser Leu Cys Tyr Ser
            195                 200                 205

Phe Leu Phe Val Gly Arg Leu Asn Leu Ile Leu Pro Pro Ser Leu Pro
    210                 215                 220

Ser Cys Pro Pro Pro Leu Gln Gly Ile Glu Thr Gly Thr Leu Cys Met
225                 230                 235                 240

Met Gln Asp Ile Leu Leu Glu Thr Leu Gly Pro Asn Arg Glu Thr Ala
                245                 250                 255

Tyr Leu Ser Gly Pro Ser Phe Ala Arg Glu Ile Ala Leu Gly Leu Val
            260                 265                 270

Thr Ala Val Val Ala Ala Ser Glu Ser Glu Ala Leu Ala Asn Glu Ile
            275                 280                 285

Cys Asp Ile Met Gly Cys Asn Tyr Phe Arg Val Phe Thr Ser Thr Asp
290                 295                 300

Val Val Gly Val Glu Val Gly Ala Val Lys Asn Val Ile Ala Ile
305                 310                 315                 320

Ala Ala Gly Met Cys Glu Gly Leu Gly Leu Gly Thr Asn Ala Met Ala
                325                 330                 335

Ala Leu Val Thr Arg Gly Cys Asn Glu Met Gln Arg Leu Ala Leu Ser
            340                 345                 350

Leu Gly Ala Arg Pro Thr Thr Leu Thr Gly Leu Ser Gly Val Gly Asp
        355                 360                 365

Thr Phe Gly Thr Cys Phe Gly Pro Leu Ser Arg Asn Arg Asn Leu Gly
    370                 375                 380

Val Arg Leu Gly Lys Gly Glu Lys Leu Glu Asp Ile Leu Gly Ser Ser
385                 390                 395                 400

Thr Glu Val Ala Glu Gly His Ala Thr Ala Phe Ser Leu Val Gln Leu
                405                 410                 415

Ile Glu Lys Thr Asn Arg Ala Tyr Arg Arg Glu Leu Glu Phe Pro Ile
            420                 425                 430

Ile Tyr Gly Val Lys Glu Ile Leu Glu Gly Lys Arg Thr Pro Ala Glu
            435                 440                 445

Gly Leu Arg Asp Leu Met Ala Met Pro Val Arg Val Glu Met Trp Asn
        450                 455                 460

Leu
465

<210> SEQ ID NO 2
<211> LENGTH: 1398
<212> TYPE: DNA
<213> ORGANISM: Nannochloropsis oculata

<400> SEQUENCE: 2

| | | |
|---|---|---|
| atgacaccct caaccaccag aagagtcaat gcaataacct tgccgcaata tgccacattc | 60 |
| acgttgggtt tcctctcact ggttgccttg ttgagctgga tgtgtccgca attcatctcc | 120 |
| caggctcatg ccgcgacggc gtttgttggg ggggctggaa gtgggagctt tgggagcagg | 180 |
| atttcgaggg gcacccgacg tacacaggga cagactacca tgctagcttc tgcgcgaaga | 240 |
| agtcgttcta cccgtccctt gccctacccc gtccgctttg ccgtgctcgg cggtgggtct | 300 |
| ttcggcctgg cccttgcctc tgtcttgggg aagaaaagca ttccagtcac tatcctggtg | 360 |
| cggaaagaag acgtggccga gcacatcaat ttgcatcatc gtcaccctac ctatctttcg | 420 |
| gatatctcat ggctcccac gattcgcgcg actaccattc cagaggaggc cttaaatgat | 480 |
| gcgtccttca ttattcatgc ggtaccggtg cagtattcta gaaagttttt ggaggacatt | 540 |
| gcgccgcatg tcccaaagaa cacgccgatt atctcgacga gcaaggtgag ctatctttgt | 600 |
| tggttttcct ctctctgtta ttcgttcctt tttgtgggcc gtctaaacct catcctccct | 660 |
| ccctccctcc cctcttgtcc tcctcccttta cagggcatag aaaccggcac cctctgcatg | 720 |
| atgcaagaca tccttctaga gactcttggc ccaaaccgcg agactgccta cctgtctggg | 780 |
| ccctcctttg cgcgtgaaat cgccttgggg ctggtcactg ctgtcgtggc cgccagtgag | 840 |
| agcgaggcgc tcgccaacga gatatgcgac atcatgggct gcaactactt ccgtgttttc | 900 |
| acctccaccg acgtggtggg tgtcgaggta ggggagctg tcaagaacgt gattgccatt | 960 |
| gccgctggga tgtgtgaggg cctggggctg gcaccaatg caatggctgc tttggtgacc | 1020 |
| agaggatgca acgagatgca gcgcctggcc ttgagcctag gcgcacggcc caccaccttg | 1080 |
| acgggactct ccggggtagg ggatacgttc gggacgtgct ttggcccctt gagcagaaat | 1140 |
| cggaatttag gagtaaggct ggggaaagga gagaagttgg aggatatatt agggtcgtca | 1200 |
| acagaggtgg cggagggaca cgccacggcc ttttctctgg tacaattgat tgagaagacc | 1260 |
| aatcgggctt acaggaggga gcttgagttt ccgattatat atgggtaaa ggagattttg | 1320 |
| gagggaaaga ggacgcccgc agagggtttg agagacttaa tggccatgcc tgtgagggtg | 1380 |
| gagatgtgga atttgtag | 1398 |

<210> SEQ ID NO 3
<211> LENGTH: 795
<212> TYPE: DNA
<213> ORGANISM: Artificial Sequence
<220> FEATURE:
<223> OTHER INFORMATION: Neomycin resistance gene

<400> SEQUENCE: 3

| | |
|---|---|
| atgattgaac aagatggatt gcacgcaggt tctccggccg cttgggtgga gaggctattc | 60 |
| ggctatgact gggcacaaca gacaatcggc tgctctgatg ccgccgtgtt ccggctgtca | 120 |

```
gcgcaggggc gcccggttct ttttgtcaag accgacctgt ccggtgccct gaatgaactg      180
caggacgagg cagcgcggct atcgtggctg gccacgacgg cgttccttg cgcagctgtg       240 ctcgacgttg cactgaagc gggaagggac tggctgctat tgggcgaagt gccggggcag      300
gatctcctgt catctcacct tgctcctgcc gagaaagtat ccatcatggc tgatgcaatg     360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac ccatggcgat gcctgcttgc cgaatatcat ggtgaaaat    600 ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                     795
```

```
<210> SEQ ID NO 4
<211> LENGTH: 490
<212> TYPE: DNA
<213> ORGANISM: Artificial Sequence
<220> FEATURE:
<223> OTHER INFORMATION: Tubulin promoter

<400> SEQUENCE: 4
actgcgcatg gattgaccga cggccggttg ccaacttttg gggtcggccc ccctttttcta    60 gcccttgccc gtccagcaat taaaaattat caacggcata ccggcactgg aagcttcggg   120
tttacaattt tggcttgcct tcctaatact gtaccgcgga gaacgtatga tattacagaa   180
aaatgccttg cacagttagc gcaaagggaa aacgtttctc cgccattgta cttttggaa   240 gagggaaagc gattgtaaaa tatggctctc cgctacgaga gtttgggctg ttgatacatg   300
tgaaaataag tgtggacgac tttgaatgac ttgatcaggc tgtttgcaca tataaccagc   360
gcgcatgcac ttctgacatg tcaatgacga aatttcacac ttcaccaata aattgtatcc   420
ttacgttttg tctttctcac acgcacatat atgatcatag ataaaagcca atatcaagaa   480
gctgtctttt                                                           490
```

```
<210> SEQ ID NO 5
<211> LENGTH: 35
<212> TYPE: DNA
<213> ORGANISM: Artificial Sequence
<220> FEATURE:
<223> OTHER INFORMATION: PCR primer No. 5

<400> SEQUENCE: 5
tcttttttgt gaagcatgat tgaacaagat ggatt                               35
```

```
<210> SEQ ID NO 6
<211> LENGTH: 35
<212> TYPE: DNA
<213> ORGANISM: Artificial Sequence
<220> FEATURE:
<223> OTHER INFORMATION: PCR primer No. 6

<400> SEQUENCE: 6
tttcccccat cccgatcaga agaactcgtc aagaa                               35
```

```
<210> SEQ ID NO 7
<211> LENGTH: 35
```

<212> TYPE: DNA
<213> ORGANISM: Artificial Sequence
<220> FEATURE:
<223> OTHER INFORMATION: PCR primer No. 7

<400> SEQUENCE: 7
cgagctcggt acccgactgc gcatggattg accga                                35

<210> SEQ ID NO 8
<211> LENGTH: 20
<212> TYPE: DNA
<213> ORGANISM: Artificial Sequence
<220> FEATURE:
<223> OTHER INFORMATION: PCR primer No. 8

<400> SEQUENCE: 8
atatcaagaa gctgtctttt                                                 20

<210> SEQ ID NO 9
<211> LENGTH: 25
<212> TYPE: DNA
<213> ORGANISM: Artificial Sequence
<220> FEATURE:
<223> OTHER INFORMATION: PCR primer No. 9

<400> SEQUENCE: 9
tcgggatggg ggaaaaaaac ctctg                                           25

<210> SEQ ID NO 10
<211> LENGTH: 36
<212> TYPE: DNA
<213> ORGANISM: Artificial Sequence
<220> FEATURE:
<223> OTHER INFORMATION: PCR primer No. 10

<400> SEQUENCE: 10
actctagagg atcccctttc gtaaataaat cagctc                               36

<210> SEQ ID NO 11
<211> LENGTH: 1000
<212> TYPE: DNA
<213> ORGANISM: Nannochloropsis oculata

<400> SEQUENCE: 11
tcgggatggg ggaaaaaaac ctctgtgtgg gctgtcagtt gatactatta gaggtctttt     60
gttttgtttg tggctgcgtg tgtgtgtttg catgagaaat agacttgaga atatcggaag    120
gaactttgac atggtaaacg aggaaaagaa aatcttcaaa aaggaataat gggtaaaaac    180
aaggagcacc gggtctcttt agaaatgctt ctcggcggaa aaccagaaaa aaaggtagaa    240
tatgtcgact ttttcgctta tcattataga atgaaagatc gaatggccaa gggatttata    300 aattcttttct ttatgttgtc gtagaactta cttttccatcc cgagggaggt gtatgcaggc    360
caaaccctct gacatgggcg caatatctct atgaaaggtt gttggaatac attgtccgac    420
ctccttcgag gcggagccgc atagttgaag tataggtgct tgcttcatcc atctcatgac    480
gctttgccag tgactcactc atgcatgtga cacatttagt tctgctcgct caagcctggc    540
ccctcctgac atgcacacat tgcacttgta ggtgggccac gtttagtata gacgccaccc    600
ctgtcgcacc atcggtccca gagcaggagc acgcttccct actcctgtac gctcccccctg    660 cttcccccccc tgctcgtcaa cgatggcgac gccagcggct gcgaattaca gtgacggcgc    720
ggccgctcag gatgacagct cctctccttc aacatctccc aatcttccac cccgcccat    780

-continued

| | |
|---|---|
| gtcgtcgttc gtacggccta tgctgaccga tatgtaccaa attacaatgg tcttcgcgta | 840 |
| ctggaagcaa aagcggcacc aggacagggc catctttgag ctcttttttcc ggaagacacc | 900 |
| ctttaaggga gagtttgcca ttatggccgg cattgacgaa gtactcaagt acttggccca | 960 |
| ctttcgcttc tccgaggagg agctgattta tttacgaaag | 1000 |

<210> SEQ ID NO 12
<211> LENGTH: 35
<212> TYPE: DNA
<213> ORGANISM: Artificial Sequence
<220> FEATURE:
<223> OTHER INFORMATION: PCR primer No. 12

<400> SEQUENCE: 12
gggatcctct agagtcgacc tgcaggcatg caagc                35

<210> SEQ ID NO 13
<211> LENGTH: 20
<212> TYPE: DNA
<213> ORGANISM: Artificial Sequence
<220> FEATURE:
<223> OTHER INFORMATION: PCR primer No. 13

<400> SEQUENCE: 13
cgggtaccga gctcgaattc                                 20

<210> SEQ ID NO 14
<211> LENGTH: 35
<212> TYPE: DNA
<213> ORGANISM: Artificial Sequence
<220> FEATURE:
<223> OTHER INFORMATION: PCR primer No. 14

<400> SEQUENCE: 14
cagcccgcat caacaatgac ccaaccaccc agcac                35

<210> SEQ ID NO 15
<211> LENGTH: 35
<212> TYPE: DNA
<213> ORGANISM: Artificial Sequence
<220> FEATURE:
<223> OTHER INFORMATION: PCR primer No. 15

<400> SEQUENCE: 15
ctcttccaca gaagctcaca ggtcatttac caaag                35

<210> SEQ ID NO 16
<211> LENGTH: 35
<212> TYPE: DNA
<213> ORGANISM: Artificial Sequence
<220> FEATURE:
<223> OTHER INFORMATION: PCR primer No. 16

<400> SEQUENCE: 16
cgagctcggt acccgttctt ccgcttgttg ctgcc                35

<210> SEQ ID NO 17
<211> LENGTH: 25
<212> TYPE: DNA
<213> ORGANISM: Artificial Sequence
<220> FEATURE:
<223> OTHER INFORMATION: PCR primer No. 17

<400> SEQUENCE: 17
tgttgatgcg ggctgagatt ggtgg                           25

<210> SEQ ID NO 18
<211> LENGTH: 800
<212> TYPE: DNA
<213> ORGANISM: Nannochloropsis oculata

<400> SEQUENCE: 18

```
ttcttccgct tgttgctgcc gatggcggcc atggtctcta agatggagtg gatggaggag      60
gaggcgagcg tagcagcaag cgtgagttat acagccaggc acatgtcgca atccttcggt     120
ctcgggctta aaatccacgc actaatcacg ctgggccatg caaagagcaa tgccgaggcc     180
caccacacaa aacgctgtgt cgcgcgttgc ggcctgaagc ttcatacttc ttagtcgccg     240
ccaaaagggc tcgagagacg agacccgttg gcatgaccga tgttgttcga cgcggtttgc     300
ttcgtcacag tcgacgtgat tcaggaatct ggagcctgca gatcattttt ttcagcctga     360
tatcgttctt ttccactgag aaccatcaga ccaccttttc ttccattgtg tgaaggagta     420
ggagttgccg tgctgctttg tgggagacat ctgcgatggt gaccagcctc ccgtcgtctg     480
gtcgacgtga cgagcctctt cactgttctt cgacggagag acgcaagcga acggctcta     540
gaccttttgg acacgcattc tgtgtgtgaa ctagtggaca gtgataccac gtctgaaagc     600
tcaccactgc ccatggtgca gctacttgtc acaaagtttt gactccgtcg gtatcaccat     660
tcgcgctcgt gtgcctggtt gttccgccac gccggcctgc cccggggcgg ggcaatattc     720
taaaatctca cgcaaaacac cgcacttacc cctcacacat attcgtgata gaccaccacc     780
aatctcagcc cgcatcaaca                                                 800
```

<210> SEQ ID NO 19
<211> LENGTH: 643
<212> TYPE: DNA
<213> ORGANISM: Artificial Sequence
<220> FEATURE:
<223> OTHER INFORMATION: VCP1 terminator

<400> SEQUENCE: 19

```
gcttctgtgg aagagccagt ggtagtagca gtagcagcag cagtagcagc cgcagcactc      60
agtgttggcg cgagagattg tccatccctt cttaacctac cggaagagaa ataaggcctt     120
tctcccgtag ctgtcttcgt ttgtttgtgc tgattgcttg atatgagagt gttgaattcc     180
tgcatcatgt ttttctctgt agtccttttcc taccccgtc attttctttt ctccctggtt     240
cttcttttgt caccttatt ttacataaaa ttttctttgt ttatagtgag aggaaggtag     300
agagggaaa acaagaacaa cgaacgcaag cgtgtgaaag gagggcgagt agaagagaaa     360
cagatctgtt gagcattgag agtggagccg ggggaaaggc ttgtgtgttg tctttgaaaa     420
agttgtttaa atcacgaatc cgttagttct catgtgtacc tctttcacta catgtgatgg     480
agaaaacaaa agtgtgagga ttaattgaag aaaagaaga gttcgacacg tcaaaccgcc     540
caaaagacgt cacaaagaga acttgattct ctttgccgtg ttgatcctgt cttttccccc     600
agcttttctt gccacccgtg gcacacgaga tggacaagat cag                       643
```

<210> SEQ ID NO 20
<211> LENGTH: 21
<212> TYPE: DNA
<213> ORGANISM: Artificial Sequence
<220> FEATURE:
<223> OTHER INFORMATION: PCR primer No. 20

<400> SEQUENCE: 20

```
gcttctgtgg aagagccagt g                                              21
```

<210> SEQ ID NO 21
<211> LENGTH: 35
<212> TYPE: DNA
<213> ORGANISM: Artificial Sequence
<220> FEATURE:
<223> OTHER INFORMATION: PCR primer No. 21

<400> SEQUENCE: 21

```
caatccatgc gcagtctgat cttgtccatc tcgtg                               35
```

<210> SEQ ID NO 22
<211> LENGTH: 20
<212> TYPE: DNA
<213> ORGANISM: Artificial Sequence
<220> FEATURE:
<223> OTHER INFORMATION: PCR primer No. 22

<400> SEQUENCE: 22

```
actgcgcatg gattgaccga                                                20
```

<210> SEQ ID NO 23
<211> LENGTH: 375
<212> TYPE: DNA
<213> ORGANISM: Artificial Sequence
<220> FEATURE:
<223> OTHER INFORMATION: Zeocin resistance gene

<400> SEQUENCE: 23

```
atggccaagc tgaccagcgc cgttccggtg ctcaccgcgc gcgacgtcgc cggagcggtc    60
gagttctgga ccgaccggct cgggttctcc cgggacttcg tggaggacga cttcgccggt   120
gtggtccggg acgacgtgac cctgttcatc agcgcggtcc aggaccaggt ggtgccggac   180
aacaccctgg cctgggtgtg ggtgcgcggc ctggacgagc tgtacgccga gtggtcggag   240
gtcgtgtcca cgaacttccg ggacgcctcc gggccggcca tgaccgagat cggcgagcag   300
ccgtgggggc gggagttcgc cctgcgcgac ccggccggca actgcgtgca cttcgtggcc   360
gaggagcagg actaa                                                    375
```

<210> SEQ ID NO 24
<211> LENGTH: 36
<212> TYPE: DNA
<213> ORGANISM: Artificial Sequence
<220> FEATURE:
<223> OTHER INFORMATION: PCR primer No. 24

<400> SEQUENCE: 24

```
tcttttttgt gaagctatgg ccaagctgac cagcgc                              36
```

<210> SEQ ID NO 25
<211> LENGTH: 36
<212> TYPE: DNA
<213> ORGANISM: Artificial Sequence
<220> FEATURE:
<223> OTHER INFORMATION: PCR primer No. 25

<400> SEQUENCE: 25

```
tttcccccat cccgattagt cctgctcctc ggccac                              36
```

<210> SEQ ID NO 26
<211> LENGTH: 1149
<212> TYPE: DNA
<213> ORGANISM: Umbellularia californica

<400> SEQUENCE: 26

```
atggccacca cctctttagc ttccgctttc tgctcgatga aagctgtaat gttggctcgt      60
gatggccggg gcatgaaacc caggagcagt gatttgcagc tgagggcggg aaatgcgcca     120
acctctttga agatgatcaa tgggaccaag ttcagttaca cggagagctt gaaaaggttg     180
cctgactgga gcatgctctt tgcagtgatc acaaccatct tttcggctgc tgagaagcag     240
tggaccaatc tagagtggaa gccgaagccg aagctacccc agttgcttga tgaccatttt     300
ggactgcatg ggttagtttt caggcgcacc tttgccatca gatcttatga ggtgggacct     360
gaccgctcca catctatact ggctgttatg aatcacatgc aggaggctac acttaatcat     420
gcgaagagtg tgggaattct aggagatgga ttcgggacga cgctagagat gagtaagaga     480
gatctgatgt gggttgtgag acgcacgcat gttgctgtgg aacggtaccc tacttggggt     540
gatactgtag aagtagagtg ctggattggt gcatctggaa ataatggcat gcgacgtgat     600
ttccttgtcc gggactgcaa aacaggcgaa attcttacaa gatgtaccag cctttcggtg     660
ctgatgaata caaggacaag gaggttgtcc acaatccctg acgaagttag aggggagata     720
gggcctgcat tcattgataa tgtggctgtc aaggacgatg aaattaagaa actacagaag     780
ctcaatgaca gcactgcaga ttacatccaa ggaggtttga ctcctcgatg gaatgatttg     840
gatgtcaatc agcatgtgaa caacctcaaa tacgttgcct gggttttga gaccgtccca     900
gactccatct ttgagagtca tcatatttcc agcttcactc ttgaatacag gagagagtgc     960
acgagggata gcgtgctgcg gtccctgacc actgtctctg gtggctcgtc ggaggctggg    1020
ttagtgtgcg atcacttgct ccagcttgaa ggtgggtctg aggtattgag ggcaagaaca    1080
gagtggaggc ctaagcttac cgatagtttc agagggatta gtgtgatacc cgcagaaccg    1140
agggtgtaa                                                            1149
```

<210> SEQ ID NO 27
<211> LENGTH: 35
<212> TYPE: DNA
<213> ORGANISM: Artificial Sequence
<220> FEATURE:
<223> OTHER INFORMATION: PCR primer No. 27

<400> SEQUENCE: 27

```
cgcggtgttg cgcgctggaa gccgaagccg aagct                                 35
```

<210> SEQ ID NO 28
<211> LENGTH: 35
<212> TYPE: DNA
<213> ORGANISM: Artificial Sequence
<220> FEATURE:
<223> OTHER INFORMATION: PCR primer No. 28

<400> SEQUENCE: 28

```
ctcttccaca gaagcttaca ccctcggttc tgcgg                                 35
```

<210> SEQ ID NO 29
<211> LENGTH: 382
<212> TYPE: PRT
<213> ORGANISM: Umbellularia californica

<400> SEQUENCE: 29

```
Met Ala Thr Thr Ser Leu Ala Ser Ala Phe Cys Ser Met Lys Ala Val
1               5                   10                  15
Met Leu Ala Arg Asp Gly Arg Gly Met Lys Pro Arg Ser Ser Asp Leu
```

```
             20                  25                  30
Gln Leu Arg Ala Gly Asn Ala Pro Thr Ser Leu Lys Met Ile Asn Gly
         35                  40                  45

Thr Lys Phe Ser Tyr Thr Glu Ser Leu Lys Arg Leu Pro Asp Trp Ser
 50                  55                  60

Met Leu Phe Ala Val Ile Thr Thr Ile Phe Ser Ala Ala Glu Lys Gln
 65                  70                  75                  80

Trp Thr Asn Leu Glu Trp Lys Pro Lys Pro Lys Leu Pro Gln Leu Leu
                 85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
            115                 120                 125

Val Met Asn His Met Gln Glu Ala Thr Leu Asn His Ala Lys Ser Val
            130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
                180                 185                 190

Gly Asn Asn Gly Met Arg Arg Asp Phe Leu Val Arg Asp Cys Lys Thr
            195                 200                 205

Gly Glu Ile Leu Thr Arg Cys Thr Ser Leu Ser Val Leu Met Asn Thr
210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
            275                 280                 285

Leu Lys Tyr Val Ala Trp Val Phe Glu Thr Val Pro Asp Ser Ile Phe
        290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
            355                 360                 365

Ser Phe Arg Gly Ile Ser Val Ile Pro Ala Glu Pro Arg Val
            370                 375                 380

<210> SEQ ID NO 30
<211> LENGTH: 802
<212> TYPE: DNA
<213> ORGANISM: Artificial Sequence
<220> FEATURE:
<223> OTHER INFORMATION: VCP1 promoter

<400> SEQUENCE: 30
ggcggtcttt tgtcctttcc tctatagccc gcccgtctag agggcacacg cgatgatctt      60
```

-continued

```
tatatctctt catgtgtctt tgttttaact aggatactgc cgggtgaatg cccatcggac    120
aagaggccaa actctatcta caccctttg acttctgttg tggtcgtagt gtgtgcttgc     180
atgccctgaa agtccaggca tcccacttgt gctctaaccc cattcaaaac agcagaagtg    240
cttaattaag atatagattc atgatctcct gtccctcct tcttacctt tcacaaacct     300 cacacagaag tctccactct tcgcctctaa aacctctttt taaattatgg taagttcgtg    360
cggcagtggg ttttcggatc tatatttgtc aagatccagt tcaaggtcag ggatgtagat    420
taagtacaga aggagaagca caagcgcgcc agttcgcccc tcacggcctg gagcagggca    480
tttaatccct ctatcttacc agaaccatac tatacaacca atcctgttgg catcgctctg    540
tctatttgtc gtgcgtgcat gtgtccatgg tgtggtgggg ggcaggggtt ttcggggttg    600
cggttgaagg caccttatca gaaagatgcc ctcagagata gaggtagccc cctccccccg    660
atcttcgacc agtcctgtca ggcgaacact ttcacccgtc gttcacctcg ttacacacaa    720
ggagtagacc tctgaagttc taattgtcat aaatgcccct ccccctccc tctttccctt    780 gatcctcccc tccgagcaga tt                                             802
```

```
<210> SEQ ID NO 31
<211> LENGTH: 99
<212> TYPE: DNA
<213> ORGANISM: Artificial Sequence
<220> FEATURE:
<223> OTHER INFORMATION: VCP1 chloroplast transit signal

<400> SEQUENCE: 31
atgaagaccg ccgctctcct cactgtctcc accctcatgg gcgcccaggc ctttatggcc    60
cccgccccca agttctcccg cacccgcggt gttgcgcgc                           99
```

```
<210> SEQ ID NO 32
<211> LENGTH: 37
<212> TYPE: DNA
<213> ORGANISM: Artificial Sequence
<220> FEATURE:
<223> OTHER INFORMATION: PCR primer No. 32

<400> SEQUENCE: 32
cgagctcggt acccgggcgg tcttttgtcc tttcctc                             37
```

```
<210> SEQ ID NO 33
<211> LENGTH: 22
<212> TYPE: DNA
<213> ORGANISM: Artificial Sequence
<220> FEATURE:
<223> OTHER INFORMATION: PCR primer No. 33

<400> SEQUENCE: 33
aatctgctcg gagggagga tc                                              22
```

```
<210> SEQ ID NO 34
<211> LENGTH: 36
<212> TYPE: DNA
<213> ORGANISM: Artificial Sequence
<220> FEATURE:
<223> OTHER INFORMATION: PCR primer No. 34

<400> SEQUENCE: 34
ccctccgagc agattatgaa gaccgccgct ctcctc                              36
```

```
<210> SEQ ID NO 35
```

```
<211> LENGTH: 28
<212> TYPE: DNA
<213> ORGANISM: Artificial Sequence
<220> FEATURE:
<223> OTHER INFORMATION: PCR primer No. 35

<400> SEQUENCE: 35
gcgcgcaaca ccgcgggtgc gggagaac                                              28

<210> SEQ ID NO 36
<211> LENGTH: 38
<212> TYPE: DNA
<213> ORGANISM: Artificial Sequence
<220> FEATURE:
<223> OTHER INFORMATION: PCR primer No. 36

<400> SEQUENCE: 36
gcggccgctc tagagtgcga cacggcccac gccgggac                                   38

<210> SEQ ID NO 37
<211> LENGTH: 39
<212> TYPE: DNA
<213> ORGANISM: Artificial Sequence
<220> FEATURE:
<223> OTHER INFORMATION: PCR primer No. 37

<400> SEQUENCE: 37
acaaaatatt aacgcctagc taatatcaat tttctttgg                                  39

<210> SEQ ID NO 38
<211> LENGTH: 287
<212> TYPE: PRT
<213> ORGANISM: Nannochloropsis oculata

<400> SEQUENCE: 38

Met Thr Pro Leu Ala Phe Thr Val Leu Gly Lys Leu Gly Gly Thr Leu
 1               5                   10                  15

Thr Phe Ala Cys Val Arg Arg Leu Tyr His Leu Leu Arg Arg Ala
                20                  25                  30

Thr Leu Ser Ser His Tyr Gln Val Thr Arg Pro Tyr Gly His Ser Asn
            35                  40                  45

Ser Gly Cys Ser His Ser Thr Thr Leu Arg Thr Ser Phe Pro Val
        50                  55                  60

Leu Phe Ala Gln Leu Ala Ala Thr Ala Ala Val Val Ala Ala Ile
65                  70                  75                  80

Ser Leu Pro Ser Pro Ser Leu Cys Glu Thr Ala His Ala Gly Thr Glu
                85                  90                  95

Glu Arg Arg Gly Glu Arg Lys Ala Met Arg Glu Asp Gly Gly Lys Gly
            100                 105                 110

Glu Ala Thr Ser Ser Ala Thr Cys Asn Pro Ser Leu Phe Glu His His
        115                 120                 125

Asp Arg Val Asp Thr Lys Leu His Arg Ala Tyr Pro Glu Phe Leu Lys
    130                 135                 140

Phe His Leu Ile His Glu Thr Leu Arg Gly Lys Glu Lys Ile Asp Gly
145                 150                 155                 160

Tyr Glu Val Tyr Lys Asp Arg Arg Asp Ser Ile Val Ala Tyr Ala
                165                 170                 175

Arg Leu Gly Lys Leu Leu Ser Gly His Pro Asp Ile Ile His Gly Gly
            180                 185                 190

Ser Ile Ala Ala Leu Leu Asp Asn Thr Met Gly Val Ala Phe Phe Ala
```

```
            195                 200                 205
    Ala Lys Arg Gly Asn Gly Phe Thr Ala Asn Leu Thr Ile Asn Tyr Lys
        210                 215                 220

Arg Pro Ile Thr Cys Gly Thr Glu Val Lys Val Leu Ala Arg Val Glu
    225                 230                 235                 240

Lys Val Glu Gly Arg Lys Val Phe Leu Arg Ala Glu Ile Arg Asp Ala
                    245                 250                 255

Lys Asp Glu Ala Ile Leu Tyr Thr Glu Ala Lys Ser Leu Phe Ile Thr
            260                 265                 270

Ser Gln Ser Pro Leu Leu Lys Gly Pro Lys Lys Ile Asp Ile Ser
            275                 280                 285
```

<210> SEQ ID NO 39
<211> LENGTH: 864
<212> TYPE: DNA
<213> ORGANISM: Nannochloropsis oculata

<400> SEQUENCE: 39

```
atgacgcctt tggccttcac ggtgctcggc aagcttggtg gcacgttgac ttttgcttgt      60
gtacgacgga ggctttatca cttgttacgg cgggcaactt tgtcctccca ttatcaggtc     120
actcggcctt acggtcacag caattccggc tgttcacata gcactaccac acttagaacc     180
agcttcccag tcctctttgc gcaattggca gcagccactg ctgccgtcgt cgctgccatt     240
tccctgccgt cgcctagtct atgcgagacg gcccacgccg ggactgagga gagacgaggt     300
gagaggaagg caatgaggga ggatggtgga aaaggcgagg ccacctcgtc tgctacatgc     360
aatccatcct tattcgaaca tcatgatcgc gtcgacacca agctgcatcg ggcctatcct     420
gaattcctga gttccacct tatccacgag acgctccgag caaagagaa aattgatggc       480 tacgaagttt acaaagacag gcgggatgat tcaattgtgg cgtatgctcg ccttggcaaa     540
ctgctgagcg acacccccga cataatccac ggagggtcca ttgcggcttt gctggacaat     600
accatgggag ttgcctttt cgccgccaag cgtggcaatg gttttacagc aaatctcacc      660
atcaactaca agcgacccat cacgtgtggc accgaagtca agttttagc tcgagtagag       720 aaggtggaag ggcgcaaggt cttcttgcgg gccgagattc gagacgctaa ggatgaggct     780
atcctctaca ctgaagccaa atccctcttc atcacgtctc aaagtccttt attgaagggc     840
ccaaagaaaa ttgatattag ctag                                            864
```

<210> SEQ ID NO 40
<211> LENGTH: 20
<212> TYPE: DNA
<213> ORGANISM: Artificial Sequence
<220> FEATURE:
<223> OTHER INFORMATION: PCR primer No. 40

<400> SEQUENCE: 40

```
ctctagagcg gccgccaccg                                                  20
```

<210> SEQ ID NO 41
<211> LENGTH: 24
<212> TYPE: DNA
<213> ORGANISM: Artificial Sequence
<220> FEATURE:
<223> OTHER INFORMATION: PCR primer No. 41

<400> SEQUENCE: 41

```
gcgttaatat tttgttaaaa ttcg                                             24
```

```
<210> SEQ ID NO 42
<211> LENGTH: 39
<212> TYPE: DNA
<213> ORGANISM: Artificial Sequence
<220> FEATURE:
<223> OTHER INFORMATION: PCR primer No. 42

<400> SEQUENCE: 42
ctggacaata ccatgggatg ggcctttttc gccgccaag                                39

<210> SEQ ID NO 43
<211> LENGTH: 20
<212> TYPE: DNA
<213> ORGANISM: Artificial Sequence
<220> FEATURE:
<223> OTHER INFORMATION: PCR primer No. 43

<400> SEQUENCE: 43
catggtattg tccagcaaag                                                     20

<210> SEQ ID NO 44
<211> LENGTH: 603
<212> TYPE: DNA
<213> ORGANISM: Nannochloropsis oculata

<400> SEQUENCE: 44
tgcgagacgg cccacgccgg gactgaggag agacgaggtg agaggaaggc aatgagggag         60
gatggtggaa aaggcgaggc cacctcgtct gctacatgca atccatcctt attcgaacat        120
catgatcgcg tcgacaccaa gctgcatcgg gcctatcctg aattcctgaa gttccacctt        180
atccacgaga cgctccgagg caaagagaaa attgatggct acgaagttta caagacagg         240 cgggatgatt caattgtggc gtatgctcgc cttggcaaac tgctgagcgg acaccccgac        300
ataatccacg gagggtccat tgcggctttg ctggacaata ccatgggatg ggcctttttc        360
gccgccaagc gtggcaatgg ttttacagca aatctcacca tcaactacaa gcgacccatc        420
acgtgtggca ccgaagtcaa agttttagct cgagtagaga aggtggaagg gcgcaaggtc        480
ttcttgcggg ccgagattcg agacgctaag gatgaggcta tcctctacac tgaagccaaa        540
tccctcttca tcacgtctca aagtccttta ttgaagggcc caaagaaaat tgatattagc        600
tag                                                                     603

<210> SEQ ID NO 45
<211> LENGTH: 822
<212> TYPE: DNA
<213> ORGANISM: Artificial Sequence
<220> FEATURE:
<223> OTHER INFORMATION: Paromomycin resistance gene

<400> SEQUENCE: 45
atggtcgaga ttcgaagcat ggacgatgcg ttgcgtgcac tgcggggtcg gtatcccggt         60
tgtgagtggg ttgttgtgga ggatgggggcc tcggggctg tgtttatcg gcttcggggt        120 ggtgggcggg agttgtttgt caaggtggca gctctggggg ccggggtggg cttgttgggt        180
gaggctgaac ggctggtgtg gttggcgag gtgggattc ccgtacctcg tgttgtggag         240
ggtggtgggg acgagagggt cgcctggttg gtcaccgaag cggttccggg gcgtccggcc        300
agtgcgcggt ggccgcggga gcagcggctg acgtggcgg tggcgctcgc ggggctcgct        360
cgttcgctgc acgcgctgga ctgggagcgg tgtccgttcg atcgcagtct cgcggtgacg        420
gtgccgcagg cggcccgtgc tgtcgctgaa gggagcgtcg acttggagga tctggacgag        480
```

```
gagcggaagg ggtggtcggg ggagcggctt ctcgccgagc tggagcggac tcggcctgcg      540
gacgaggatc tggcggtttg ccacggtgac ctgtgcccgg acaacgtgct gctcgaccct      600
cgtacctgcg aggtgaccgg gctgatcgac gtggggcggg tcggccgtgc ggaccggcac      660
tccgatctcg cgctggtgct gcgcgagctg gcccacgagg aggacccgtg gttcgggccg      720
gagtgttccg cggcgttcct gcgggagtac gggcgcgggt gggatggggc ggtatcggag      780
gaaaagctgg cgttttaccg gctgttggac gagttcttct ga                         822
```

<210> SEQ ID NO 46
<211> LENGTH: 35
<212> TYPE: DNA
<213> ORGANISM: Artificial Sequence
<220> FEATURE:
<223> OTHER INFORMATION: PCR primer No. 46

<400> SEQUENCE: 46
tcttttttgt gaagcatggt cgagattcga agcat                                 35

<210> SEQ ID NO 47
<211> LENGTH: 35
<212> TYPE: DNA
<213> ORGANISM: Artificial Sequence
<220> FEATURE:
<223> OTHER INFORMATION: PCR primer No. 47

<400> SEQUENCE: 47
tttcccccat cccgatcaga agaactcgtc caaca                                 35

<210> SEQ ID NO 48
<211> LENGTH: 454
<212> TYPE: PRT
<213> ORGANISM: Nannochloropsis oculata

<400> SEQUENCE: 48

```
Met Arg Val Ser Ser Ala Val Leu Gly Cys Ala Leu Leu Phe Ile
1               5                   10                  15

Ala Pro Thr Leu Ala Tyr Leu Pro Thr Asn Val Arg Ala Ser Lys Gly
            20                  25                  30

Arg Ile Tyr Met Lys Glu Lys Thr Gln Arg Val Val Val Thr Gly Leu
        35                  40                  45

Gly Pro Ile Ser Ala Val Gly Ile Gly Lys Asp Asp Phe Trp Lys Ala
    50                  55                  60

Leu Leu Glu Gly Lys Cys Gly Ile Asp Lys Ile Ser Gly Phe Asp Pro
65                  70                  75                  80

Ser Gly Leu Thr Cys Gln Ile Gly Ala Glu Val Lys Gly Phe Asp Ala
                85                  90                  95

Lys Pro Tyr Phe Lys Asp Lys Lys Ser Ala Val Arg Asn Asp Arg Val
            100                 105                 110

Thr Leu Met Gly Val Ala Ala Ser Arg Ile Ala Val Asp Asp Ala Arg
        115                 120                 125

Leu Asp Leu Ala Thr Val Glu Gly Glu Arg Phe Gly Val Val Val Gly
    130                 135                 140

Ser Ala Phe Gly Gly Leu Gln Thr Leu Glu Thr Gln Ile Gln Ser Met
145                 150                 155                 160

Asn Glu Lys Gly Pro Gly Ala Val Ser Pro Phe Ala Val Pro Met Leu
                165                 170                 175

Leu Ser Asn Leu Ile Ser Gly Val Ile Ala Leu Glu Asn Gly Ala Lys
```

|  | 180 |  |  | 185 |  |  |  | 190 |  |

Gly Pro Asn Tyr Val Val Asn Ser Ala Cys Ala Ala Ser Thr His Ala
            195                 200                 205

Leu Gly Leu Ala Tyr Ala His Ile Ala His Gly Glu Ala Asp Val Cys
    210                 215                 220

Leu Ala Gly Gly Ala Glu Ala Ala Val Thr Pro Phe Gly Tyr Ala Gly
225                 230                 235                 240

Phe Cys Ser Met Lys Ala Met Ala Thr Lys Tyr Asn Asp Asn Pro Ser
                245                 250                 255

Gln Gly Ser Arg Pro Phe Asp Lys Asp Arg Cys Gly Phe Val Met Gly
            260                 265                 270

Glu Gly Ala Gly Met Leu Val Leu Glu Ser Leu Glu His Ala Gln Lys
        275                 280                 285

Arg Gly Ala His Ile Tyr Ala Glu Val Ala Gly Phe Gly Gln Ala Cys
    290                 295                 300

Asp Ala His His Ile Thr Thr Pro His Pro Glu Gly Ala Gly Leu Ala
305                 310                 315                 320

Lys Ala Ile Thr Leu Ala Leu Asp Asp Ala Gly Leu Asp Lys Gly Asp
                325                 330                 335

Leu Thr Tyr Ile Asn Ala His Gly Thr Ser Thr Ala Tyr Asn Asp Lys
            340                 345                 350

Phe Glu Thr Leu Ala Val Lys Lys Ala Leu Gly Glu Glu Asn Ala Lys
        355                 360                 365

Arg Met Tyr Leu Ser Ser Thr Lys Gly Ser Thr Gly His Thr Leu Gly
    370                 375                 380

Ala Ala Gly Gly Leu Glu Ala Ile Ala Thr Val Leu Ala Ile Glu Thr
385                 390                 395                 400

Leu Thr Leu Pro Pro Thr Ile Asn Tyr Glu Thr Pro Asp Pro Asp Cys
                405                 410                 415

Asp Leu Asn Val Val Pro Asn Lys Pro Ile Lys Val Ala Glu Ile Lys
            420                 425                 430

Ala Ala Ala Ser Gln Ser Ala Gly Phe Gly Gly His Asp Ser Val Val
        435                 440                 445

Ile Phe Lys Pro Phe Lys
    450

<210> SEQ ID NO 49
<211> LENGTH: 1365
<212> TYPE: DNA
<213> ORGANISM: Nannochloropsis oculata

<400> SEQUENCE: 49
atgcgggtct ccagtagcgc cgttttaggc tgcgccctcc tcttcatcgc ccctaccttg     60
gcatacctgc ctaccaacgt gcgcgcctca aagggccgaa tctacatgaa ggagaagacc    120
caacgcgtgg tcgtgacagg cctagggccc atatcggccg tagggatcgg caaggacgat    180
ttctggaagg cgttgctaga ggggaagtgc ggcattgaca agatcagtgg ctttgaccct    240
agtggattga cgtgccaaat tggtgcggaa gtgaagggtt ttgatgcgaa gccgtatttt    300
aaggacaaga aaagcgccgt ccgtaacgac cgtgtgacac tgatggggt ggccgcttca    360 agaatcgccg ttgatgatgc caggctggac ttggccacag tggaaggaga gcgcttcggc    420
gtggtggtgg gctccgcttt tgggggcctg caaacgctcg agacgcagat tcagagcatg    480
aatgagaagg gcccgggggc tgtgtcgccc tttgcggttc ccatgttgtt gtccaacttg    540

```
atctcgggcg tgattgcctt ggagaacggg gcaaaaggac cgaactacgt ggtgaatagc      600
gcgtgtgccg cctcgaccca tgccctcggt ctggcgtacg cccatatcgc gcacggggag      660
gcggatgtct gcttggccgg cggggcggag gctgccgtga caccgttcgg gtacgcgggg      720
ttttgctcca tgaaagccat ggcgaccaaa tacaacgaca accccctccca aggctcccgt      780 cccttcgaca aggatcggtg cggctttgtc atgggcgagg gtgccggtat gctcgtcctc      840
gaatctctcg aacacgccca aaaacgcggc gcgcacatct atgccgaagt cgccggcttt      900
ggtcaggcct gtgacgccca ccatatcacg acccctcacc ccgaggggc gggtctggcg      960 aaagccatca ccttggcatt ggatgacgcg ggcttggaca agggtgattt aacgtacatc     1020
aacgcccatg gcaccagcac ggcgtacaac gacaagttcg agacgttggc ggtcaagaag     1080
gccttggggg aggagaacgc caagaggatg tatttatcgt cgaccaaggg gtcgacggga     1140
cacacgctcg gggccgcggg agggttggag gcgattgcga cagtactagc gattgagacg     1200
ttgaccttgc cccccaccat caactatgag acaccagacc cggactgtga cctgaatgtg     1260
gttcccaaca aacccattaa agtggcgag atcaaagccg ctgcttctca gtcggcaggg      1320
tttggagggc atgactcggt tgtaatcttc aaaccgttca agtaa                     1365

<210> SEQ ID NO 50
<211> LENGTH: 35
<212> TYPE: DNA
<213> ORGANISM: Artificial Sequence
<220> FEATURE:
<223> OTHER INFORMATION: PCR primer No. 50

<400> SEQUENCE: 50
aaatcataca gcaggatgcg ggtctccagt agcgc                                 35

<210> SEQ ID NO 51
<211> LENGTH: 34
<212> TYPE: DNA
<213> ORGANISM: Artificial Sequence
<220> FEATURE:
<223> OTHER INFORMATION: PCR primer No. 51

<400> SEQUENCE: 51
ctcttccaca gaagcttact tgaacggttt gaag                                  34

<210> SEQ ID NO 52
<211> LENGTH: 689
<212> TYPE: DNA
<213> ORGANISM: Artificial Sequence
<220> FEATURE:
<223> OTHER INFORMATION: Ubiquitin promoter

<400> SEQUENCE: 52
gctgctgccc cgaccgtatc tccaagtcag acatgaaatc ttcagttgcg ttaaaaactc       60
tacgatgcta ccagcgttaa ataaccttgc ccacgccttt aaacgtaccc gatcattaac      120
atatcgactg gctgccttgg cttggcacca gccatcatca gacttaacga tgggtatgtt     180
gcttgccttt cctgcttgaa gggggtccga ctctctgctt tctcgatcgc gggtgtgacc      240
tctgaattgg aatgtaaaaa tgtaagaagc gacgtgtccg gtaaagaaat gcccaagctc      300
catcaaatct gcgttgtcgg cgaccaaacc atgctggctc gtcgacctgc cccggatgca      360
ggagcatggc actcggcggc atggcacttg agcctcgcgg gaggaatgtg tgtggttggg      420
cgcaggctgt ggacggcccc cctccagcga agccggtcgcc tcccttttccg acgctttgtg      480 cacgttgtct ggtgtcctct gtctcacgca cctcttcacc gacgtggtgt ccctcttgtt      540
```

```
gctggtgagg gacttggaat gtggtcctgg ttctatcctg ggcgcgtgtg ttccttttt     600 tctctaccgt tattctctcc atttctgatg tctcaccacc atctccctca ccctccaacc   660
gcgtcgttgt gccaaaatca tacagcagg                                      689
```

<210> SEQ ID NO 53
<211> LENGTH: 35
<212> TYPE: DNA
<213> ORGANISM: Artificial Sequence
<220> FEATURE:
<223> OTHER INFORMATION: PCR primer No. 53

<400> SEQUENCE: 53

```
cgagctcggt acccggctgc tgccccgacc gtatc                               35
```

<210> SEQ ID NO 54
<211> LENGTH: 21
<212> TYPE: DNA
<213> ORGANISM: Artificial Sequence
<220> FEATURE:
<223> OTHER INFORMATION: PCR primer No. 54

<400> SEQUENCE: 54

```
cctgctgtat gattttggca c                                              21
```

<210> SEQ ID NO 55
<211> LENGTH: 1176
<212> TYPE: DNA
<213> ORGANISM: Saccharomyces cerevisiae

<400> SEQUENCE: 55

```
atgtctgctg ctgctgatag attaaactta acttccggcc acttgaatgc tggtagaaag    60
agaagttcct cttctgtttc tttgaaggct gccgaaaagc ctttcaaggt tactgtgatt   120
ggatctggta actggggtac tactattgcc aaggtggttg ccgaaaattg taagggatac   180
ccagaagttt tcgctccaat agtacaaatg tgggtgttcg aagaagagat caatggtgaa   240
aaattgactg aaatcataaa tactagacat caaaacgtga atacttgcc tggcatcact    300 ctacccgaca atttggttgc taatccagac ttgattgatt cagtcaagga tgtcgacatc   360
atcgttttca acattccaca tcaattttg ccccgtatct gtagccaatt gaaaggtcat    420
gttgattcac acgtcagagc tatctcctgt ctaaagggtt ttgaagttgg tgctaaaggt   480
gtccaattgc tatcctctta catcactgag gaactaggta ttcaatgtgg tgctctatct   540
ggtgctaaca ttgccaccga agtcgctcaa gaacactggt ctgaaacaac agttgcttac   600
cacattccaa aggatttcag aggcgagggc aaggacgtcg accataaggt tctaaaggcc   660
ttgttccaca gaccttactt ccacgttagt gtcatcgaag atgttgctgg tatctccatc   720
tgtggtgctt tgaagaacgt tgttgcctta ggttgtggtt tcgtcgaagg tctaggctgg   780
ggtaacaacg cttctgctgc catccaaaga gtcggtttgg gtgagatcat cagattcggt   840
caaatgtttt tcccagaatc tagagaagaa acatactacc aagagtctgc tggtgttgct   900
gatttgatca ccacctgcgc tggtggtaga aacgtcaagg ttgctaggct aatggctact   960
tctggtaagg acgcctggga atgtgaaaag gagttgttga atggccaatc cgctcaaggt  1020
ttaattacct gcaaagaagt tcacgaatgg ttggaaacat gtggctctgt cgaagacttc  1080
ccattatttg aagccgtata ccaaatcgtt tacaacaact acccaatgaa gaacctgccg  1140
gacatgattg aagaattaga tctacatgaa gattag                            1176
```

<210> SEQ ID NO 56
<211> LENGTH: 35
<212> TYPE: DNA
<213> ORGANISM: Artificial Sequence
<220> FEATURE:
<223> OTHER INFORMATION: PCR primer No. 56

<400> SEQUENCE: 56
cagcccgcat caacaatgtc tgctgctgct gatag         35

<210> SEQ ID NO 57
<211> LENGTH: 35
<212> TYPE: DNA
<213> ORGANISM: Artificial Sequence
<220> FEATURE:
<223> OTHER INFORMATION: PCR primer No. 57

<400> SEQUENCE: 57
ctcttccaca gaagcctaat cttcatgtag atcta         35

<210> SEQ ID NO 58
<211> LENGTH: 1500
<212> TYPE: DNA
<213> ORGANISM: Nannochloropsis oculata

<400> SEQUENCE: 58

| | | |
|---|---|---|
| ctgtcatgcc gttgtcgcct ccgctgccga ggtggggagg catctttctc ctccttttcg | 60 |
| tctttacggc tcttggaaag ggtagaatga aaggagagg aggaagggct atcgtgtcgt | 120 |
| cttcgtcgac gtggaggagc tgcgtcctcg tcagcaccag catcaacagc aacacgaaaa | 180 |
| gaaggaagag gtggactatc gtggcgcttg cgacgccggg gaggcgaagc gtcctcaacg | 240 |
| acagcaccag cgaacccact ggcgcgggca tgcgcagcac gaggaggaga ggggaaagg | 300 |
| ctctgacggc gtgtccgccg gggaggagaa ttgtcagggc tggaactgtc ctgccgtggg | 360 |
| cgccgccggg gagggaaat gtcactagtg gctgctgctc ccggtgcggg gtcggctgct | 420 |
| gccttcttcg aagcggcttc cacggaggcg acttggtcgc ccttgtcgtc tacgaccagg | 480 |
| gggccgtcat caactgaggg gataggagca ggatacagag aagagggatg agcgatcgac | 540 |
| attttgaata tggtatggac ttctccgtgt tgctgcccat tgttatgagc gagtataaca | 600 |
| gtgctgatag ttcctcctct acactcatgt cacgtcgcat acaagtacat accttcgtta | 660 |
| tcgctgccgc cccgaccaaa cccgcccat tcgtcctggt ccaccaggtg catgccgccc | 720 |
| gttacgactg cgggcctctt tttgcgtttc ttctttgtct ttatgacctc tgtagtgtat | 780 |
| atgatgcatg tggtatatgg gcgggtaggg agggaataca tacttccttt ccttttcctc | 840 |
| aggccgtcga cttcccatcc cccacaatcg ccgcagtttc catttctttg ctgcaacctt | 900 |
| cacgcctcac ctaccattag attcgctcat cgaagatgag aggtaccgct tgaggatgtc | 960 |
| tgctttagac ttggcggagg ccatggttgg ggggttggct gacttgctgt gtaggagggc | 1020 |
| gacgcgtgct gatgctgatg ataagacgtt tgcctggtgg ctgcagcacc ctgtgttttt | 1080 |
| gtgtgtgtgg tggatcgagg tcaggaacca gggcctgttt atggataacc gtgcgggcat | 1140 |
| gtgggacgtc ttcttctgat attatagtgg actaggacag caaaaggcag caaaaccatg | 1200 |
| ccggcatcgc tcgctcgcac ccccaatcat catcactccg gcgagccagc aaggcaagtt | 1260 |
| gttgaccttt ccctagtgtc aagcccgtgg ggacgtgcga gggacgtagc gcaattgcat | 1320 |
| gcgtgctttg cctagtcagc ttcctttgcc tgttaaagcg gggtcgcatc atccctccat | 1380 |
| ctcttcgatt tcatgacaca gggactgcgg cctgggcagc gacaaacgct tgcgtactcc | 1440 | ttctctctcc ctggtggctg gcaggtctgc tgcaactccg cccgcccttg ctctacgacc    1500

<210> SEQ ID NO 59
<211> LENGTH: 303
<212> TYPE: PRT
<213> ORGANISM: Cocos nucifera

<400> SEQUENCE: 59

Leu Asp Ser Lys Lys Arg Gly Ala Asp Ala Val Ala Asp Ala Ser Gly
1               5                   10                  15

Val Gly Lys Met Val Lys Asn Gly Leu Val Tyr Arg Gln Asn Phe Ser
            20                  25                  30

Ile Arg Ser Tyr Glu Ile Gly Val Asp Lys Arg Ala Ser Val Glu Ala
        35                  40                  45

Leu Met Asn His Phe Gln Glu Thr Ser Leu Asn His Cys Lys Cys Ile
    50                  55                  60

Gly Leu Met His Gly Gly Phe Gly Cys Thr Pro Glu Met Thr Arg Arg
65                  70                  75                  80

Asn Leu Ile Trp Val Val Ala Lys Met Leu Val His Val Glu Arg Tyr
                85                  90                  95

Pro Trp Trp Gly Asp Val Val Gln Ile Asn Thr Trp Ile Ser Ser Ser
            100                 105                 110

Gly Lys Asn Gly Met Gly Arg Asp Trp His Val His Asp Cys Gln Thr
        115                 120                 125

Gly Leu Pro Ile Met Arg Gly Thr Ser Val Trp Val Met Met Asp Lys
    130                 135                 140

His Thr Arg Arg Leu Ser Lys Leu Pro Glu Glu Val Arg Ala Glu Ile
145                 150                 155                 160

Thr Pro Phe Phe Ser Glu Arg Asp Ala Val Leu Asp Asp Asn Gly Arg
                165                 170                 175

Lys Leu Pro Lys Phe Asp Asp Ser Ala Ala His Val Arg Arg Gly
            180                 185                 190

Leu Thr Pro Arg Trp His Asp Phe Asp Val Asn Gln His Val Asn Asn
    195                 200                 205

Val Lys Tyr Val Gly Trp Ile Leu Glu Ser Val Pro Val Trp Met Leu
210                 215                 220

Asp Gly Tyr Glu Val Ala Thr Met Ser Leu Glu Tyr Arg Arg Glu Cys
225                 230                 235                 240

Arg Met Asp Ser Val Val Gln Ser Leu Thr Ala Val Ser Ser Asp His
                245                 250                 255

Ala Asp Gly Ser Pro Ile Val Cys Gln His Leu Leu Arg Leu Glu Asp
            260                 265                 270

Gly Thr Glu Ile Val Arg Gly Gln Thr Glu Trp Arg Pro Lys Gln Gln
    275                 280                 285

Ala Cys Asp Leu Gly Asn Met Gly Leu His Pro Thr Glu Ser Lys
290                 295                 300

<210> SEQ ID NO 60
<211> LENGTH: 912
<212> TYPE: DNA
<213> ORGANISM: Cocos nucifera

<400> SEQUENCE: 60
ctcgattcca agaagagggg ggccgacgcg gtcgcagatg cctctggggt cgggaagatg    60
gtcaagaatg gacttgttta caggcagaat ttttctatcc ggtcctacga aatcggggtt    120

```
gataaacgtg cttcggtaga ggcattgatg aatcatttcc aggaaacgtc gcttaaccat      180
tgcaagtgta ttggccttat gcatggcggc tttggttgta caccagagat gactcgaaga      240
aatctgatat gggttgttgc caaaatgctg gttcatgtcg aacgttatcc ttggtgggga      300
gacgtggttc aaataaatac gtggattagt tcatctggaa agaatggtat gggacgtgat      360
tggcatgttc atgactgcca aactggccta cctattatga ggggtaccag tgtctgggtc      420
atgatggata acacacgag gagactgtct aaacttcctg aagaagttag agcagagata       480
acccctttct tttcagagcg tgatgctgtt ttggacgata acggcagaaa acttcccaag      540
ttcgatgatg attctgcagc tcatgttcga aggggcttga ctcctcgttg gcatgatttc      600
gatgtaaatc agcatgtgaa caatgtcaaa tacgtcggct ggattcttga gagcgttcct      660
gtgtggatgt tggatggcta cgaggttgca accatgagtc tggaataccg gagggagtgt      720
aggatggata gtgtggtgca gtctctcacc gccgtctctt ccgaccacgc cgacggctcc      780
cccatcgtgt gccagcatct tctgcggctc gaggatggga ctgagattgt gaggggtcaa      840
acagaatgga ggcctaagca gcaggcttgt gatcttggga acatgggtct gcacccaact      900
gagagtaaat ga                                                         912

<210> SEQ ID NO 61
<211> LENGTH: 274
<212> TYPE: PRT
<213> ORGANISM: Nannochloropsis gaditana

<400> SEQUENCE: 61

Met Leu Cys Cys Ala Cys Lys Ser Val His Ala Thr Ile Ser Val Ala
1               5                   10                  15

Phe Ile Gly Thr Arg Lys Pro His Arg Leu Pro Ala Leu Phe Pro Leu
            20                  25                  30

Phe Leu Ala Pro Ala Arg Ala Leu Ser His Gln Glu Pro Asn Pro Ala
        35                  40                  45

Thr Cys Gly Thr Gln Asn Ser Ser Phe Ser Ile Leu Leu Lys Thr Val
    50                  55                  60

Val Ala Gly Ser Phe Val Gly Ala Ala Phe Ile Ala Gly His Thr Ala
65                  70                  75                  80

Gly Ala Ser Cys Asp Glu Val Lys Ser Pro Gln Glu Val Asn Val
                85                  90                  95

Gly Gly Gly Ala Pro Val Thr Ala Pro Tyr Thr Val Thr Phe Ala Ser
            100                 105                 110

Asn Tyr His Asp Arg Val Asp Thr Lys Leu His Arg Ala Tyr Pro Glu
        115                 120                 125

Phe Leu Gln Tyr His Leu Ile His Glu Thr Leu Arg Gly Lys Glu Lys
    130                 135                 140

Ile Glu Gly Tyr Glu Val Tyr Lys Asp Arg Arg Asp Asp Ser Ile Val
145                 150                 155                 160

Ala Phe Ala Arg Leu Gly Lys Leu Leu Ser Gly His Pro Asp Ile Ile
                165                 170                 175

His Gly Gly Ser Ile Ala Ala Leu Leu Asp Asn Thr Met Gly Val Ala
            180                 185                 190

Phe Phe Ala Ala Asn Lys Gly Asn Gly Phe Thr Ala Asn Leu Thr Ile
        195                 200                 205

Asn Tyr Lys Arg Pro Ile Ile Cys Gly Thr Glu Ile Lys Val Leu Ala
    210                 215                 220
```

```
Arg Val Glu Arg Phe Glu Gly Arg Lys Val Phe Leu Arg Ala Glu Ile
225                 230                 235                 240

Arg Asp Ala Lys Asp Glu Ala Val Leu Tyr Thr Glu Ala Thr Ser Leu
                245                 250                 255

Phe Ile Thr Ser Gln Ser Pro Leu Leu Thr Gly Pro Lys Lys Val Asp
            260                 265                 270

Ile Ser

<210> SEQ ID NO 62
<211> LENGTH: 825
<212> TYPE: DNA
<213> ORGANISM: Nannochloropsis gaditana

<400> SEQUENCE: 62
atgctatgtt gcgcctgtaa atcagtgcat gcgactatta gtgtcgcctt tattggtact      60
cggaagccac atcgtttgcc tgcattgttt ccattgttcc ttgccccggc ccgagcactc     120
agccatcagg agccgaaccc tgcaacgtgc gggacgcaaa actcatcctt ctcgatcttg     180
ttgaaaacgg tagtagcagg atcattcgtc ggtgcggcat tcatcgctgg catacagca     240 ggggctagct gtgatgaagt aaagtctccg caggaggtga acaatgtagg aggcggcgcc     300
ccagtgactg cccctacac ggtcactttt gcgtccaatt atcatgatcg agtggacaca     360
aaacttcata gagcttatcc tgagttttta cagtaccatc ttattcatga aacgcttcga     420
ggcaaggaaa agatagaggg ctacgaggtg tacaaagata ggcgtgacga ttctatcgta     480
gcatttgctc gcctcgggaa gcttctcagc gggcatccgg atataatcca tggaggctct     540
atagccgcct actcgacaa cactatgggc gtggcattct tcgctgccaa taaaggtaat     600
ggcttcactg ccaacctcac aatcaattac aagaggccga tcatttgtgg caccgagatc     660
aaggtcttgg cccgagtgga gcggtttgaa ggacgcaagg ttttcctacg agcagagatt     720
cgagatgcta aggacgaggc agtgttgtac acggaagcca catccctctt cataacttca     780
caaagtcctc tgcttacggg accgaagaag gtggacatca gttag                    825

<210> SEQ ID NO 63
<211> LENGTH: 285
<212> TYPE: PRT
<213> ORGANISM: Nannochloropsis granulata

<400> SEQUENCE: 63

Met Thr Pro Leu Ala Phe Thr Ala Leu Gly Glu Val Gly Gly Met Leu
1               5                   10                  15

Ala Ala Ala Cys Val Arg Arg Lys Leu His His Leu Leu Arg Arg Ala
                20                  25                  30

Ala Ser Ser Ser Gln Val Thr Arg Pro Tyr Ser His Ser Thr Ala Asn
            35                  40                  45

Ser Thr His Ser Thr Thr Thr Leu Ser Asn Ser Phe Pro Val Leu Phe
        50                  55                  60

Ala Gln Leu Ala Ala Ala Ala Ala Val Met Ala Ala Thr Ser Leu
65                  70                  75                  80

Ser Ser Pro Ser Leu Cys Glu Thr Ala His Thr Asn Thr Glu Glu Arg
                85                  90                  95

Gly Gly Glu Gly Glu Ala Met Arg Glu Lys Gly Gly Glu Gly Glu Ala
            100                 105                 110

Thr Ser Ser Ala Thr Cys Ala Pro Ser Phe Phe Glu His His Asp Arg
        115                 120                 125
```

Val Asp Thr Lys Leu His Arg Ala Tyr Pro Glu Phe Leu Lys Phe His
130                 135                 140

Leu Ile His Glu Thr Leu Arg Gly Lys Glu Lys Ile Asp Gly Tyr Glu
145                 150                 155                 160

Val Tyr Lys Asn Arg Arg Asp Asp Ser Val Val Ala Tyr Ala Arg Leu
            165                 170                 175

Gly Lys Leu Leu Ser Gly His Pro Asp Ile Ile His Gly Gly Ser Ile
            180                 185                 190

Ala Ala Leu Leu Asp Asn Thr Met Gly Val Ala Phe Phe Ala Ala Lys
            195                 200                 205

Arg Gly Asn Gly Phe Thr Ala Asn Leu Thr Ile Asn Tyr Lys Arg Pro
210                 215                 220

Ile Thr Cys Gly Thr Glu Val Lys Val Leu Ala Arg Val Glu Lys Val
225                 230                 235                 240

Glu Gly Arg Lys Val Phe Leu Arg Ala Glu Ile Arg Asp Ala Lys Asp
            245                 250                 255

Glu Ala Ile Leu Tyr Thr Glu Ala Asn Ser Leu Phe Ile Thr Ser Gln
            260                 265                 270

Ser Pro Leu Leu Lys Gly Pro Lys Lys Ile Asp Ile Ser
            275                 280                 285

<210> SEQ ID NO 64
<211> LENGTH: 858
<212> TYPE: DNA
<213> ORGANISM: Nannochloropsis granulata

<400> SEQUENCE: 64
atgacgcctt tggccttcac ggcgctcggc gaggtcggtg gcatgttggc tgctgcctgt        60
gtacgacgga agcttcatca cttgttgcgg cgggcagctt cgtcctccca ggtcactcga       120
ccttacagtc acagcaccgc caacagcaca catagcacca ccacacttag caacagcttt       180
ccagtcctct tgcgcaact cgcagcagcc gctgctgccg tcatggctgc cacttccctg        240
tcgtcgccca gtctatgtga cggcccac accaatactg aggagagagg aggcgaaggg         300
gaggcaatga gggagaaggg tggggaaggc gaggccactt cgtctgctac atgcgctcca       360
tctttcttcg agcatcatga tcgcgtcgac acgaagctgc atcgggccta tcccgagttt      420
ctgaagttcc acctcatcca cgagacgctc gagggaaag agaaaattga tggctacgaa       480
gtatacaaaa acaggcggga cgattcagtt gtggcgtatg ctcgcctggg caaactgctg       540
agcggacacc ctgacataat tcacggaggg tccatcgctg ctttgctgga caacaccatg      600
ggagttgcct ttttcgccgc caagcgcggc aatggtttca gcaaatctc accatcaac        660 tacaagcgac ccatcacgtg tggcaccgag gtcaaagttc tggctcgagt agagaaggtg      720 gagggggcgca aggtcttttt gcgggctgag atcagggacg ccaaggatga ggctatcctt    780
tacactgaag ccaactccct cttcatcacg tcgcaaagcc ctctattgaa gggcccaaag    840
aaaattgaca ttagctag                                                   858

<210> SEQ ID NO 65
<211> LENGTH: 233
<212> TYPE: PRT
<213> ORGANISM: Symbiodinium microadriaticum

<400> SEQUENCE: 65

Met Ala Phe Arg Leu Cys Ser Leu Ser Arg Arg Phe Ala Ala His Ala
1               5                   10                  15

Gln Gln Val Leu Arg Lys Glu Ala Gly Phe Glu Phe Arg Ala Ser Cys
            20                  25                  30

Ile Ala Ile Thr Ala Gly Ile Ser Ala Gly Trp Cys Met Gln Gln Ala
        35                  40                  45

Ala Arg Ala Glu Gly Ile Trp Thr Pro His Leu Gly Glu Glu Ala Lys
    50                  55                  60

Leu Leu Asn Leu Gln Arg Glu Met Ala Leu Arg Asp Arg His Asp Lys
65                  70                  75                  80

Gln Phe Val Trp Gln Thr Cys Ser Gly Gln Gly Lys Ile Glu Asp Cys
                85                  90                  95

Arg Ile Tyr His Cys Lys Arg Glu Glu Val Asp Arg Glu Val Ser Leu
            100                 105                 110

Asp Ala Pro Glu Met Val Glu Gly Lys Thr Arg Ile Cys Ala Val Met
        115                 120                 125

Arg Val Gly Asp Glu Leu Asn Gly His Pro Gly Leu Leu His Gly Gly
    130                 135                 140

Phe Thr Ala Ala Val Leu Asp Asp Phe Thr Gly Leu Ala Thr Trp Met
145                 150                 155                 160

Glu Lys Gln Ala Gln Ala Leu Asp Lys Asp Ala Ala Ile Phe Thr Ala
                165                 170                 175

His Met Asp Leu Ser Tyr Arg Arg Pro Leu Lys Ala Lys Ser Glu Tyr
            180                 185                 190

Leu Val Glu Val Cys Val Asp Arg Val Glu Arg Gln Lys Lys Val Phe
        195                 200                 205

Leu Asn Ala Ala Ile Tyr Asp Lys Asp Ser His Ala Cys Val Lys Ala
    210                 215                 220

Lys Val Leu Tyr Ile Val Lys Lys Lys
225                 230

<210> SEQ ID NO 66
<211> LENGTH: 702
<212> TYPE: DNA
<213> ORGANISM: Symbiodinium microadriaticum

<400> SEQUENCE: 66
atggctttca ggctatgctc tctttcccgg cggtttgctg cgcacgcgca gcaggtgctg      60
cggaaggagg ctggctttga gttccgcgca agctgcatcg ccattaccgc tggcatctct     120
gctggatggt gcatgcagca ggcagcgcgg gcggagggca tctggactcc gcacctgggc     180
gaggaggcca agttgttgaa cctccagcgc gagatggcgc tgagagacag acacgacaag     240
caatttgtgt ggcagacctg cagtggccag ggcaaaattg aggactgccg catatatcac     300
tgcaagcgag aagaagttga tcgtgaggtt cgctggacg cgccggaaat ggtggagggc     360
aaaacacgga tttgtgcagt gatgcgcgtt ggcgacgagc tgaacggcca tcctgggctt     420
ttgcatggcg gcttcactgc cgccgtgctg acgatttca caggcctggc gacctggatg     480
gagaagcaag cgcaggcgct ggacaaggat gcggccattt tcaccgctca catggatctc     540
agctatcggc gaccctgaa ggcgaagtcg gagtacttgg ttgaggtttg cgttgaccgt     600
gttgagcggc aaaagaaggt ctttctgaat gctgccatct atgacaagga cagccatgcc     660
tgcgtgaaag caaggtgtt gtacatcgtc aaaaagaagt ga                        702

<210> SEQ ID NO 67
<211> LENGTH: 458
<212> TYPE: PRT
<213> ORGANISM: Nannochloropsis gaditana

<400> SEQUENCE: 67

Met Arg Leu Ser Thr Leu Ser Val Leu Gly Pro Ala Leu Gly Cys Ala
1               5                   10                  15

Phe Leu Leu Phe Asp Ser Ser Leu Ala Tyr Leu Pro Ser Tyr Met Arg
                20                  25                  30

Gly Ser Lys Gly Gln Ile Tyr Met Lys Glu Lys Ser Gln Arg Val Val
            35                  40                  45

Val Thr Gly Leu Gly Pro Ile Ser Ala Val Gly Ile Gly Lys Asp Ala
        50                  55                  60

Phe Trp Lys Ala Leu Leu Glu Gly Lys Ser Gly Ile Asp Arg Ile Ser
65                  70                  75                  80

Gly Phe Asp Pro Ser Gly Leu Thr Cys Gln Ile Gly Ala Glu Val Lys
                85                  90                  95

Asp Phe Asp Ala Lys Pro Tyr Phe Lys Asp Arg Lys Ser Ala Val Arg
                100                 105                 110

Asn Asp Arg Val Thr Leu Met Gly Val Ala Ala Ser Arg Ile Ala Val
            115                 120                 125

Asp Asp Ala Lys Leu Asp Leu Ser Ser Val Glu Gly Glu Arg Phe Gly
130                 135                 140

Val Val Val Gly Ser Ala Phe Gly Gly Leu Gln Thr Leu Glu Thr Gln
145                 150                 155                 160

Ile Gln Thr Met Asn Glu Lys Gly Pro Gly Ser Val Ser Pro Phe Ala
                165                 170                 175

Val Pro Ser Leu Leu Ser Asn Leu Ile Ser Gly Val Ile Ala Leu Glu
            180                 185                 190

Asn Gly Ala Lys Gly Pro Asn Tyr Val Val Asn Ser Ala Cys Ala Ala
            195                 200                 205

Ser Thr His Ala Leu Gly Leu Ala Tyr Ala His Ile Ala His Gly Glu
        210                 215                 220

Ala Asp Val Cys Leu Ala Gly Gly Ser Glu Ala Ala Val Thr Pro Phe
225                 230                 235                 240

Gly Phe Ala Gly Phe Cys Ser Met Lys Ala Met Ala Thr Lys Tyr Asn
                245                 250                 255

Asp Asn Pro Ser Gln Gly Ser Arg Pro Phe Asp Lys Asp Arg Cys Gly
            260                 265                 270

Phe Val Met Gly Glu Gly Ala Gly Met Val Val Leu Glu Ser Leu Glu
                275                 280                 285

His Ala Gln Lys Arg Gly Ala His Ile Tyr Ala Glu Val Ala Gly Phe
        290                 295                 300

Gly Gln Ala Cys Asp Ala His His Ile Thr Thr Pro His Pro Glu Gly
305                 310                 315                 320

Ala Gly Leu Ala Gln Ala Ile Thr Leu Ala Leu Glu Asp Ala Gly Met
                325                 330                 335

Ala Lys Glu Asp Leu Thr Tyr Ile Asn Ala His Gly Thr Ser Thr Ala
            340                 345                 350

Tyr Asn Asp Lys Phe Glu Thr Leu Ala Val Lys Lys Ala Leu Gly Glu
        355                 360                 365

Glu Val Ala Lys Lys Met Tyr Leu Ser Ser Thr Lys Gly Ser Thr Gly
        370                 375                 380

His Thr Leu Gly Ala Ala Gly Gly Leu Glu Ala Ile Ala Thr Val Leu
385                 390                 395                 400

Ala Ile Glu Thr Lys Thr Leu Pro Pro Thr Ile Asn Tyr Glu Thr Pro

```
                    405                 410                 415
Asp Pro Asp Cys Asp Leu Asn Val Val Pro Asn Lys Pro Ile Thr Leu
            420                 425                 430

Asn Glu Ile Thr Gly Ala Ala Ser Gln Ser Ala Gly Phe Gly Gly His
            435                 440                 445

Asp Ser Val Val Val Phe Lys Pro Phe Lys
            450                 455
```

<210> SEQ ID NO 68
<211> LENGTH: 1377
<212> TYPE: DNA
<213> ORGANISM: Nannochloropsis gaditana

<400> SEQUENCE: 68

| | | | | | |
|---|---|---|---|---|---|
| atgcggcttt | cgactctcag | cgtcttgggc | cctgcactag | gatgcgcctt | cctactattc | 60 |
| gattcaagcc | tggcatatct | accgagctat | atgcgtgggt | ctaagggaca | aatctatatg | 120 |
| aaggaaaaaa | gtcagcgtgt | cgtcgtaacg | ggtcttggac | ccatatccgc | tgtgggtatt | 180 |
| gggaaagatg | ccttctggaa | agcgctgttg | aagggaaaa | gtggtatcga | tcgcatcagc | 240 |
| ggctttgacc | cctccggcct | cacttgccag | attggcgccg | aagtaaaaga | tttcgatgcc | 300 |
| aagccttatt | tcaaggatag | gaagagcgca | gttcgtaacg | acagggtgac | cttgatggga | 360 |
| gtggccgcct | cgcgcattgc | tgtggacgat | gccaagctgg | atttgtcgtc | ggtgagggg | 420 |
| gaacgcttcg | gggttgtggt | agggtccgcg | ttcggagggc | ttcaaacgct | tgagacccag | 480 |
| attcagacca | tgaacgaaaa | gggtccgggc | tccgtgtctc | ccttcgccgt | gccaagtttg | 540 |
| ttgtccaact | tgatttcggg | ggtgattgcg | ttggaaaatg | gcgcgaaagg | ccccaactac | 600 |
| gtcgtgaaca | gcgcctgtgc | cgcgtccacc | cacgccctgg | ggctggccta | cgcacacatt | 660 |
| gcccacggag | aggcggacgt | gtgcctggcg | ggcgggtcgg | aagcggctgt | gacccccgttc | 720 |
| ggattcgcgg | gcttttgctc | gatgaaagcc | atggccacaa | agtacaatga | caaccccagc | 780 |
| caaggctccc | gacctttcga | taaggaccgt | tgcggttttg | tcatgggaga | ggggggccggg | 840 |
| atggtggtgc | tggaaagctt | ggagcatgcg | cagaaacggg | gcgcgcatat | ttacgccgag | 900 |
| gtggcgggct | ttgggcaggc | gtgcgacgcc | accatatca | ccactccgca | ccctgaggga | 960 |
| gcgggcttgg | cccaggcaat | cacgttggca | ttggaggacg | cgggtatggc | gaaagaggac | 1020 |
| ttgacctaca | ttaatgccca | tggcaccagc | accgcctaca | tgacaaaatt | cgagacgctg | 1080 |
| gcggtcaaga | aggccttggg | agaggaggtg | gccaaaaaga | tgtacttgtc | gtcgaccaag | 1140 |
| ggatcgacgg | gccacacgct | gggagcggcg | ggtggactgg | aagcaatcgc | gacagtcctg | 1200 |
| gccatagaga | cgaagacact | gccgcctacg | atcaattacg | agacgcctga | cccggattgc | 1260 |
| gacctaaacg | tagtgccgaa | caagcccatc | accctgaatg | agatcacagg | ggccgcctct | 1320 |
| cagtccgctg | gcttcggcgg | gcatgactcg | gtggtggtgt | tcaaaccatt | caaataa | 1377 |

<210> SEQ ID NO 69
<211> LENGTH: 482
<212> TYPE: PRT
<213> ORGANISM: Umbellularia californica

<400> SEQUENCE: 69

```
Met Gln Ile Leu Gln Thr Pro Ser Ser Arg Ser Pro Leu Arg Val
1               5                   10                  15

Ser Ser Met Glu Ser Leu Ser Leu Thr Pro Lys Ser Leu Pro Leu Lys
            20                  25                  30
```

```
Thr Leu Leu Pro Phe Arg Pro Arg Pro Lys Asn Leu Ser Arg Arg Lys
            35                  40                  45

Ser Gln Asn Pro Lys Pro Ile Ser Ser Ser Ser Pro Glu Arg Glu
 50                  55                  60

Thr Asp Pro Lys Lys Arg Val Val Ile Thr Gly Met Gly Leu Val Ser
 65                  70                  75                  80

Val Phe Gly Asn Asp Val Asp Ala Tyr Tyr Asp Arg Leu Leu Ser Gly
            85                  90                  95

Glu Ser Gly Ile Ala Pro Ile Asp Arg Phe Asp Ala Ser Lys Phe Pro
            100                 105                 110

Thr Arg Phe Ala Gly Gln Ile Arg Gly Phe Thr Ser Asp Gly Tyr Ile
            115                 120                 125

Asp Gly Lys Asn Asp Arg Arg Leu Asp Asp Cys Leu Arg Tyr Cys Ile
            130                 135                 140

Val Ser Gly Lys Lys Ala Leu Glu Asn Ala Gly Leu Gly Pro Asp Leu
145                 150                 155                 160

Met Asp Gly Lys Ile Asp Lys Glu Arg Ala Gly Val Leu Val Gly Thr
            165                 170                 175

Gly Met Gly Gly Leu Thr Val Phe Ser Asn Gly Val Gln Thr Leu His
            180                 185                 190

Glu Lys Gly Tyr Arg Lys Met Thr Pro Phe Phe Ile Pro Tyr Ala Ile
            195                 200                 205

Thr Asn Met Gly Ser Ala Leu Leu Ala Ile Asp Leu Gly Phe Met Gly
            210                 215                 220

Pro Asn Tyr Ser Ile Ser Thr Ala Cys Ala Thr Ser Asn Tyr Cys Phe
225                 230                 235                 240

Tyr Ala Ala Ala Asn His Ile Arg Arg Gly Glu Ala Asp Val Met Leu
            245                 250                 255

Ala Gly Gly Thr Glu Ala Ala Ile Ile Pro Ile Gly Leu Gly Gly Phe
            260                 265                 270

Val Ala Cys Arg Ala Leu Ser Gln Arg Asn Asp Asp Pro Gln Thr Ala
            275                 280                 285

Ser Arg Pro Trp Asp Lys Asp Arg Asp Gly Phe Val Met Gly Glu Gly
            290                 295                 300

Ala Gly Val Leu Val Met Glu Ser Leu Glu His Ala Met Lys Arg Asp
305                 310                 315                 320

Ala Pro Ile Ile Ala Glu Tyr Leu Gly Gly Ala Val Asn Cys Asp Ala
            325                 330                 335

Tyr His Met Thr Asp Pro Arg Ala Asp Gly Leu Gly Val Ser Thr Cys
            340                 345                 350

Ile Glu Arg Ser Leu Glu Asp Ala Gly Val Ala Pro Glu Glu Val Asn
            355                 360                 365

Tyr Ile Asn Ala His Ala Thr Ser Thr Leu Ala Gly Asp Leu Ala Glu
            370                 375                 380

Val Asn Ala Ile Lys Lys Val Phe Thr Asn Thr Ser Glu Ile Lys Ile
385                 390                 395                 400

Asn Ala Thr Lys Ser Met Ile Gly His Cys Leu Gly Ala Ala Gly Gly
            405                 410                 415

Leu Glu Ala Ile Ala Thr Ile Lys Ala Ile Asn Thr Gly Trp Leu His
            420                 425                 430

Pro Ser Ile Asn Gln Phe Asn Pro Glu Pro Ser Val Glu Phe Asp Thr
            435                 440                 445

Val Ala Asn Lys Lys Gln Gln His Glu Val Asn Val Ala Ile Ser Asn
```

Ser Phe Gly Phe Gly Gly His Asn Ser Val Val Phe Ser Ala Phe
465                 470                 475                 480

Lys Pro

<210> SEQ ID NO 70
<211> LENGTH: 1449
<212> TYPE: DNA
<213> ORGANISM: Umbellularia californica

<400> SEQUENCE: 70

| | | | | | |
|---|---|---|---|---|---|
| atgcaaatcc | tccaaacccc | atcatcatca | cggtctcctc | tccgcgtgtc | gtccatggaa | 60 |
| tctctctctc | tcaccccctaa | atctctccct | ctcaaaaccc | ttcttcccttt | tcgtcctcgc | 120 |
| cctaaaaacc | tctccagacg | caaatcccaa | aaccctaaac | ccatctcctc | ctcttcctcc | 180 |
| ccggagagag | agacggatcc | caagaagcga | gtcgtcatca | ccgggatggg | cctcgtctcc | 240 |
| gtcttcggca | cgacgtcga | tgcctactac | gaccgcctcc | tctccggaga | gagcggcatc | 300 |
| gcccccatcg | atcgcttcga | cgcctccaag | ttccccacca | gattcgccgg | tcagatccga | 360 |
| gggttcacct | ccgacggcta | cattgacggg | aagaacgacc | gccggttaga | cgattgtctc | 420 |
| agatactgta | tcgttagtgg | aagaaggcg | ctcgagaatg | ccggcctcgg | acccgatctc | 480 |
| atggacggaa | agattgacaa | ggagcgagct | ggtgtgcttg | tcgggacagg | catgggtggt | 540 |
| cttacagttt | tctctaatgg | ggttcagact | ctccatgaga | aaggttacag | aaaatgact | 600 |
| ccgttttttca | tcccttatgc | cataacaaac | atgggtctg | ccttgcttgc | aattgacctt | 660 |
| ggtttatgg | gcccaaacta | ttctatctca | actgcatgtg | ctacctccaa | ttattgcttt | 720 |
| tatgctgctg | ctaaccatat | acggagaggt | gaggctgatg | tgatgcttgc | tggtggaact | 780 |
| gaagctgcaa | ttattcctat | tggcttagga | ggctttgttg | catgtagagc | tttatcacag | 840 |
| agaaatgatg | accccagac | agcttcaaga | ccatgggaca | agatcgaga | cggttttgtt | 900 |
| atgggtgaag | gtgctggagt | attggtaatg | gagagcttgg | agcatgctat | gaaacgtgat | 960 |
| gcaccaatta | ttgctgagta | tttaggaggt | gcagtgaact | gtgatgcgta | tcatatgacg | 1020 |
| gatcctagag | ctgatgggct | cgggggtttca | acatgcatag | aaagaagtct | tgaagatgct | 1080 |
| ggtgtggcac | ctgaagaggt | taactacata | aatgcacatg | caacttccac | acttgcaggt | 1140 |
| gacctggccg | aggtgaatgc | catcaaaaag | gttttttacaa | acacttcaga | gatcaaaatc | 1200 |
| aatgcaacca | agtctatgat | agggcactgc | cttggagcgg | ccgggggttt | agaagccatt | 1260 |
| gccacaatca | aagcaataaa | tactggttgg | ctgcacccctt | ccataaaacca | atttaatcca | 1320 |
| gagccctctg | ttgagtttga | cactgtagca | aataaaagc | agcagcatga | agtgaatgtt | 1380 |
| gccatttcca | actctttcgg | gtttggtgga | cacaactcgg | tcgtggtgtt | ttcggcattc | 1440 |
| aagccttga | | | | | | 1449 |

<210> SEQ ID NO 71
<211> LENGTH: 567
<212> TYPE: PRT
<213> ORGANISM: Umbellularia californica

<400> SEQUENCE: 71

Met Val Val Ser Ser Val Ala Ser Pro Leu Cys Thr Trp Leu Val Ala
1               5                   10                  15

Ala Cys Met Ser Val Thr Cys Glu Lys Asp Ser Ser Met Arg Ile Ser
            20                  25                  30

```
Gly Leu Ala Pro Ser Lys Arg Trp Ser Lys Trp Met Met Arg Gln Arg
            35                  40                  45

Val Val Leu Lys Gly Gly Arg Glu Asp Phe Pro Lys Gly Leu Ile Ser
 50                  55                  60

Ala Phe Cys Gly Ala Ser Ile Gln Gly Leu Met Ser Ser Cys Leu Ala
 65                  70                  75                  80

Phe Glu Pro Cys Glu Glu Tyr Tyr Ser Ser Lys Gly Leu Ser Leu Ser
                 85                  90                  95

Pro Ser Ser Leu Ser Ser Phe Phe Gly Glu Ser Gly Phe Ser Leu Phe
             100                 105                 110

Gly Trp Lys Glu Gly Thr Thr Arg Arg Gln Arg Arg Met Val Asn His
            115                 120                 125

Ala Ala Ser Gly Lys Thr Met Asn Val Ala Val Glu Pro Ser Lys Glu
            130                 135                 140

Val Val Lys Lys Glu Lys Pro Val Thr Lys Gln Arg Arg Val Val
145                 150                 155                 160

Thr Gly Met Gly Val Val Thr Pro Leu Gly His Asp Pro Asp Val Phe
                165                 170                 175

Tyr Asn Asn Leu Leu Glu Gly Val Ser Gly Ile Ser Gly Ile Glu Ala
                180                 185                 190

Phe Asp Cys Ser His Phe Pro Thr Arg Ile Ala Gly Glu Ile Lys His
            195                 200                 205

Phe Ser Ser Asp Gly Cys Val Ala Pro Lys Leu Ser Lys Arg Met Asp
            210                 215                 220

Lys Phe Met Leu Tyr Leu Leu Thr Ala Gly Lys Lys Ala Leu Ala Asp
225                 230                 235                 240

Gly Gly Ile Thr Asn Asp Val Met Asn Met Leu Asp Lys Ser Lys Cys
                245                 250                 255

Gly Val Leu Ile Gly Ser Ala Met Gly Gly Met Lys Val Phe Asn Asp
                260                 265                 270

Ala Ile Glu Ala Leu Arg Val Ser Tyr Lys Lys Met Asn Pro Phe Cys
            275                 280                 285

Val Pro Phe Ala Thr Thr Asn Met Gly Ser Ala Ile Leu Ala Met Asp
            290                 295                 300

Leu Lys Trp Met Gly Pro Asn Tyr Ser Ile Ser Thr Ala Cys Ala Thr
305                 310                 315                 320

Ser Asn Phe Cys Ile Leu Asn Ala Ala Asn His Ile Lys Arg Asn Glu
                325                 330                 335

Ala Asp Met Met Leu Cys Gly Gly Ser Asp Ala Ala Ile Ile Pro Ile
            340                 345                 350

Gly Leu Gly Gly Phe Val Ala Cys Arg Ala Leu Ser Gln Arg Asn Glu
            355                 360                 365

Asp Pro Thr Lys Ala Ser Arg Pro Trp Asp Val His Arg Asp Gly Phe
            370                 375                 380

Val Met Gly Glu Gly Ala Gly Val Leu Leu Leu Glu Glu Leu Glu His
385                 390                 395                 400

Ala Lys Arg Arg Gly Ala Asn Ile Tyr Ala Glu Phe Leu Gly Gly Ser
                405                 410                 415

Phe Thr Cys Asp Ala Tyr His Met Thr Glu Pro His Pro Asp Gly Thr
            420                 425                 430

Gly Ile Ser Leu Cys Ile Glu Lys Ala Leu Ser Gln Ser Gly Val Ser
            435                 440                 445

Arg Glu Asp Val Asn Tyr Val Asn Ala His Ala Thr Ser Thr Gln Ser
```

```
                450            455            460
Gly Asp Leu Lys Glu Tyr Ser Ala Leu Ile Arg Cys Phe Gly Gln Asn
465             470                 475                 480

Pro Lys Leu Arg Val Asn Ser Thr Lys Ser Met Ile Gly His Leu Ile
            485                 490                 495

Gly Ala Ala Gly Ala Val Glu Ala Val Ala Thr Ile Gln Ala Ile Arg
            500                 505                 510

Thr Gly Trp Val His Pro Asn Ile Asn Leu Glu Thr Pro Glu Glu Thr
            515                 520                 525

Val Asp Pro Thr Leu Leu Val Gly Pro Lys Lys Glu Arg Leu Asp Ile
530             535                 540

Lys Val Ala Leu Ser Asn Ser Phe Gly Phe Gly His Asn Ser Ser
545             550                 555                 560

Ile Ile Phe Val Pro Tyr Thr
                565

<210> SEQ ID NO 72
<211> LENGTH: 1704
<212> TYPE: DNA
<213> ORGANISM: Umbellularia californica

<400> SEQUENCE: 72
atggtggtct cctctgttgc atctcctctc tgcacatggc tagttgccgc ttgcatgtcg      60
gtcacctgcg agaaggattc ctcgatgagg atttctgggc tcgctccttc gaagaggtgg     120
agtaagtgga tgatgaggca gagggtcgtt ttgaaaggag ggagagagga ttttccaaag     180
ggtctgatct cagctttctg tggagcgagc attcaagggc taatgagttc ttgcctggcc     240
ttcgagccct gtgaggagta ttatagctca aaggggcttt cattgtctcc atcttcctta     300 tcttcttct ttggagagag tggtttctct ttgtttgggt ggaaagaggg gactacacgc      360
agacagagaa ggatggtgaa tcatgctgct caggaaaaa ccatgaatgt agctgttgaa      420
ccttcgaagg aagttgtgaa gaaggagaaa cctgttacaa gcagagaag ggttgttgtg      480 acagggatgg gtgtggtgac acccctaggc cacgatcctg atgtattcta caataatctc     540
cttgagggtg taagcggtat aagtggaatt gaagcatttg actgttccca ttttccaacg     600
cgaattgctg gcgaaataaa acatttctca tcggatggat gtgttgctcc gaaactttct     660
aagaggatgg acaaatttat gctttaccta ctgactgctg gcaagaaagc attggcagat     720
ggagggatca ctaatgatgt catgaatatg ttggacaaat caaaatgcgg ggttcttatt     780
ggctccgcaa tgggtgggat gaaggtgttt aatgatgcaa tagaagcttt aagggtctcg     840
tacaagaaga tgaatccctt ttgtgttcct tttgcaacta ctaatatggg ctctgcaata     900
cttgcaatgg atttgaaatg gatggggcca actattcga tttcaactgc ttgtgcaact     960
agcaactttt gtatattgaa tgcagcaaac cacattaaaa gaaatgaagc tgatatgatg    1020
ctatgtggtg gtctgatgc agcaatcata ccgattgggt taggtggttt tgtagcgtgc    1080
agagcacttt cacagagaaa tgaggatcca accaaagctt cacgaccatg ggatgttcat    1140
cgtgatggtt tcgttatggg agagggagct ggcgttctac ttttggaaga attggaacat    1200
gcaaagagaa ggggagcaaa catctatgca gagttttta gtggaagctt cacgtgtgat    1260
gcttatcata tgactgagcc tcatcctgat gggacaggaa tttcccttg catagagaag    1320 gccttatctc aatctggggt gtccagaaa gatgtgaatt atgtgaatgc tcatgctact    1380
tcaacgcagt caggtgacct gaaagagtac agtgctctca ttcgttgttt cgggcagaac    1440
```

-continued

```
cccaagctga gagtaaactc tacaaaatcc atgattggcc acctcatagg agcagctggt    1500
gctgtagaag ctgttgcaac catacaggct atccggactg ggtgggtgca tccgaacatc    1560
aacctggaaa ccccagagga aactgtggac ccaactcttt tggtgggccc caagaaggag    1620
agattggaca tcaaggtggc actttctaat tcatttggct ttggtggcca caactcgtcc    1680 atcattttg ttccttacac ttga                                           1704
```

<210> SEQ ID NO 73
<211> LENGTH: 567
<212> TYPE: PRT
<213> ORGANISM: Cinnamomum camphora

<400> SEQUENCE: 73

```
Met Val Ser Ser Val Ala Ser Pro Leu Cys Thr Trp Leu Val Ala
1               5                   10                  15

Ala Cys Met Ser Val Ala Cys Glu Lys Asp Ser Ser Met Arg Ile Ser
            20                  25                  30

Gly Phe Ala Pro Ser Lys Arg Trp Ser Lys Trp Val Arg Arg Gln Arg
        35                  40                  45

Val Val Leu Lys Gly Gly Arg Glu Asp Phe Pro Lys Gly Leu Ile Ser
    50                  55                  60

Ala Phe Cys Gly Ala Ser Ile Gln Gly Leu Met Ser Ser Cys Leu Ala
65                  70                  75                  80

Phe Glu Pro Cys Glu Glu Tyr Tyr Ser Ser Lys Gly Leu Ser Leu Ser
                85                  90                  95

Pro Ser Ser Leu Ser Ser Phe Phe Gly Glu Ser Gly Phe Ser Leu Phe
            100                 105                 110

Gly Trp Lys Glu Gly Thr Thr Arg Arg Gln Arg Met Val Asn Arg
        115                 120                 125

Ala Ala Ser Gly Lys Thr Met Asn Val Ala Val Glu Pro Ser Lys Glu
    130                 135                 140

Val Val Lys Lys Glu Lys Pro Val Thr Lys Gln Arg Arg Val Val Val
145                 150                 155                 160

Thr Gly Met Gly Val Val Thr Pro Leu Gly His Asp Pro Asp Val Phe
                165                 170                 175

Tyr Asn Asn Leu Leu Glu Gly Val Ser Gly Ile Ser Glu Ile Glu Ala
            180                 185                 190

Phe Asp Cys Ser His Phe Pro Thr Arg Ile Ala Gly Glu Ile Lys Asn
        195                 200                 205

Phe Ser Ser Asp Gly Cys Val Ala Pro Lys Leu Ser Lys Arg Met Asp
    210                 215                 220

Lys Phe Met Leu Tyr Leu Leu Thr Ala Gly Lys Lys Ala Leu Ala Asp
225                 230                 235                 240

Gly Gly Ile Thr Asn Asp Val Met Asn Met Leu Asp Lys Ser Lys Cys
                245                 250                 255

Gly Val Leu Ile Gly Ser Ala Met Gly Gly Met Lys Val Phe Asn Asp
            260                 265                 270

Ala Ile Glu Ala Leu Arg Val Ser Tyr Lys Lys Met Asn Pro Phe Cys
        275                 280                 285

Val Pro Phe Ala Thr Thr Asn Met Gly Ser Ala Ile Leu Ala Met Asp
    290                 295                 300

Leu Lys Trp Met Gly Pro Asn Tyr Ser Ile Ser Thr Ala Cys Ala Thr
305                 310                 315                 320

Ser Asn Phe Cys Ile Leu Asn Ala Ala Asn His Ile Lys Arg Asn Glu
```

```
                 325                 330                 335
Ala Asp Met Met Leu Cys Gly Gly Ser Asp Ala Ala Ile Ile Pro Ile
            340                 345                 350
Gly Leu Gly Gly Phe Val Ala Cys Arg Ala Leu Ser Gln Arg Asn Glu
            355                 360                 365
Asp Pro Thr Lys Ala Ser Arg Pro Trp Asp Val His Arg Asp Gly Phe
        370                 375                 380
Val Met Gly Glu Gly Ala Gly Val Leu Leu Glu Glu Leu Glu His
385                 390                 395                 400
Ala Lys Arg Arg Gly Ala Asn Ile Tyr Ala Glu Phe Leu Gly Gly Ser
                405                 410                 415
Phe Thr Cys Asp Ala Tyr His Met Thr Glu Pro His Pro Asp Gly Thr
                420                 425                 430
Gly Ile Ser Leu Cys Ile Glu Lys Ala Leu Ser Gln Ser Gly Val Ser
                435                 440                 445
Arg Glu Asp Val Asn Tyr Val Asn Ala His Ala Thr Ser Thr Gln Ser
450                 455                 460
Gly Asp Leu Lys Glu Tyr Ser Ala Leu Ile Arg Cys Phe Gly Gln Asn
465                 470                 475                 480
Pro Lys Leu Arg Val Asn Ser Thr Lys Ser Met Ile Gly His Leu Ile
                485                 490                 495
Gly Ala Ala Gly Ala Val Glu Ala Val Ala Thr Ile Gln Ala Ile Arg
            500                 505                 510
Thr Gly Trp Val His Pro Asn Ile Asn Leu Glu Thr Pro Glu Glu Thr
            515                 520                 525
Val Asp Pro Thr Leu Leu Val Gly Pro Lys Lys Glu Arg Leu Asp Ile
        530                 535                 540
Lys Val Ala Leu Ser Asn Ser Phe Gly Phe Gly Gly His Asn Ser Ser
545                 550                 555                 560
Ile Ile Phe Val Pro Tyr Thr
                565

<210> SEQ ID NO 74
<211> LENGTH: 1704
<212> TYPE: DNA
<213> ORGANISM: Cinnamomum camphora

<400> SEQUENCE: 74
atggtggtct cctctgttgc ttctcctctc tgcacttggc tagttgccgc ttgcatgtcg      60
gtcgcctgcg agaaggattc ctcgatgagg atttctgggt tcgctccttc gaagaggtgg     120
agtaagtggg tgaggaggca gagggtcgtt ttgaaaggag ggagagagga ttttccaaag     180
ggtctgatct cagcttttctg tggagcgagc attcaagggc taatgagttc ttgcctggcc     240
ttcgagccct gtgaggagta ttatagctca aggggctttt cattgtctcc atcttcctta     300
tcttccttct ttggagagag tggttttctct ttgtttgggt ggaaagaggg gactacacgc     360
agacagagaa ggatggtgaa tcgtgctgct tcaggaaaaa ccatgaatgt agctgttgaa     420
ccttcgaagg aagttgtgaa gaaggagaaa cctgttacaa gcagagaagg gttgttgtg      480 acagggatgg gtgtggtgac acctctaggc acgatcctg atgtattcta caataatctc     540
cttgagggtg taagcggtat aagtgaaatt gaagcatttg actgttccca ttttccaacg     600
cgaattgctg cgaaataaa aaatttctca tcggatggat gtgttgctcc gaaactttct     660
aagaggatgg acaaatttat gctttaccta ctgactgctg gcaagaaagc attggcagat     720
```

-continued

```
ggagggatca ctaatgatgt catgaatatg ttggacaaat caaaatgcgg ggttctcatt    780
ggctccgcaa tgggtgggat gaaggtgttt aatgatgcaa tagaagcttt aagggtctcg    840
tacaagaaga tgaatcccttt ttgtgttcct tttgcaacta ctaatatggg ctctgcaata    900
cttgcaatgg atttgaaatg gatggggcca aactattcga tttcaactgc ttgtgcaact    960
agcaactttt gtatattgaa tgcagcaaac cacattaaaa gaaatgaagc tgatatgatg   1020
ctatgtggtg ggtctgatgc agcaatcata ccaatcgggt taggtggttt tgtagcatgc   1080
agagcacttt cacagagaaa tgaggatcca accaaagctt cacgaccatg ggatgttcat   1140
cgtgacggtt tcgttatggg agagggagct ggcgttctac ttttggaaga attggaacat   1200
gcaaagagaa ggggagcaaa catctatgca gagttttttag gtggaagctt cacgtgtgat   1260
gcttatcata tgactgagcc tcatcctgac gggacaggaa tttcccttttg catagagaag   1320
gccttatctc aatctggggt atccagagaa gatgtgaatt atgtgaatgc tcatgctact   1380
tcaacgcagt caggtgacct gaaagagtac agtgctctca ttcgttgttt cgggcagaac   1440
cctaagctga gagtaaactc tacaaaatcc atgattggcc acctcatagg agcagctggt   1500
gctgtagaag ctgttgcaac catacaggcg atccggactg ggtgggtgca tccgaacatc   1560
aacctggaaa ccccagagga aactgtggac ccaactcttc tggtggggcc caagaaggag   1620
agattggaca tcaaggtggc actttctaat tcatttggct ttggtggcca caactcgtcc   1680
atcattttttg ttccttacac ttga                                         1704
```

<210> SEQ ID NO 75
<211> LENGTH: 421
<212> TYPE: PRT
<213> ORGANISM: Nannochloropsis oculata

<400> SEQUENCE: 75

```
Met Lys Gln Cys Ser His His Val Met Pro Ser Arg Thr Pro Thr Ala
1               5                   10                  15

Phe Ser Phe Val Phe Leu Pro Ser Leu Val Leu Ser Phe Val Phe Leu
            20                  25                  30

Gln Cys Cys Thr Leu Phe Pro Ser Thr Ala Ala Phe Leu Leu Pro Ser
        35                  40                  45

Ser Ser Leu Ser Ser Thr Ser Ser Asp Tyr Tyr Ser Ser Ser Ser Leu
    50                  55                  60

Arg Arg Arg Val Ala Leu Gln Met Gln Gly Glu Gly Ser Gly Thr Gly
65                  70                  75                  80

Lys Ser Val Ala Gly Arg Ser Phe Leu Arg Ser Lys Pro Ile Gly Val
                85                  90                  95

Gly Ser Ala Ala Pro Ala Asp Val Ile Lys Asn Thr Asp Leu Glu Ser
            100                 105                 110

Val Val Glu Thr Ser Asp Glu Trp Ile Phe Thr Arg Thr Gly Ile Ser
        115                 120                 125

Gln Arg Arg Ile Leu Pro Ser Gly Gly Gln Ile Arg Gly Leu Ala Ala
    130                 135                 140

Thr Ala Ala Ala Arg Ala Leu Glu Asn Ala Gly Leu Glu Gly Lys Asp
145                 150                 155                 160

Ile Asp Val Val Ile Leu Ala Thr Ser Ser Pro Asp Asp Leu Phe Gly
                165                 170                 175

Asp Ala Thr Ser Val Ala Ala Ala Val Gly Ala Thr Gly Ala Val Ala
            180                 185                 190

Phe Asp Leu Thr Ala Ala Cys Ser Gly Phe Leu Phe Gly Val Val Thr
```

```
                  195                 200                 205
Ala Ser Gln Phe Leu His Ser Gly Cys Tyr Arg His Ala Leu Val Val
    210                 215                 220

Gly Ala Asp Ala Leu Ser Arg Trp Val Asp Trp Glu Asp Arg Asn Ser
225                 230                 235                 240

Cys Ile Leu Phe Gly Asp Gly Ala Gly Val Val Leu Thr Val Ala
                245                 250                 255

Glu Gly Asp Ala Asp Ser Gly Val Leu Gly Phe Ala Met His Ser Asp
                260                 265                 270

Gly Thr Gly Gln Gly Asp Leu Asn Leu Gln Phe Ala Lys Asp Glu Ser
                275                 280                 285

Gln Ser Pro Pro Glu Ile Asn Ala Val Thr Pro Tyr Lys Gly Lys Tyr
    290                 295                 300

Asn Asn Ile Ala Met Asn Gly Lys Glu Val Tyr Lys Phe Ala Thr Arg
305                 310                 315                 320

Lys Val Pro Thr Val Ile Glu Glu Ala Leu Ala Asn Ala Gly Leu Gly
                325                 330                 335

Val Glu Glu Val Asp Trp Leu Leu His Gln Ala Asn Ile Arg Ile
                340                 345                 350

Met Asp Val Val Ala Asp Arg Leu Gly Leu Ser Lys Asp Lys Ile Leu
                355                 360                 365

Thr Asn Leu Ser Asp Tyr Gly Asn Thr Ser Ala Gly Ser Ile Pro Leu
    370                 375                 380

Ala Leu Asp Glu Ala Val Lys Ser Gly Lys Val Lys Lys Gly Asp Ile
385                 390                 395                 400

Ile Ala Cys Ala Gly Phe Gly Ala Gly Leu Ser Trp Gly Ser Ala Ile
                405                 410                 415

Ile Arg Trp Gln Gly
            420

<210> SEQ ID NO 76
<211> LENGTH: 1266
<212> TYPE: DNA
<213> ORGANISM: Nannochloropsis oculata

<400> SEQUENCE: 76
atgaagcagt gcagtcatca cgtcatgcct tcacgcacac caacagcttt ctccttcgtc    60
ttcctaccct ccctcgtcct ctcgttcgtc ttcctacaat gttgcacact ttttccctcg   120
accgccgcct tcctccttcc ttcctcctcc ctctcttcca cctcctctga ctactattcc   180
tcatcctcct gcgacgacg tgtcgccctc caaatgcaag gagaaggctc tggcaccggc   240
aaatctgtgg caggtcgttc ttttctgagg tccaagccta ttggtgtggg cagtgcggcc   300
cctgctgacg tgataaagaa cacggacctt gaaagcgtgg tggagacttc ggatgaatgg   360
attttcaccc ggacaggtat ctctcaacgc cgcatcctc cctcgggcgg gcaaattcgg   420
ggcttggccg ccacggccgc tgcccgtgct ctagaaaacg cagggctgga aggaaaggac   480
attgatgtgg tgattctcgc cacgtcttcc ccggacgatc tcttcgggga tgccacgagc   540
gtggcggcgg ccgttggtgc aacgggcgcc gtggcgtttg atttaacggc cgcttgctcg   600
ggctttctct tcggcgtggt aacagcgtcg cagttcctcc actcggggtg ctaccgccac   660
gccctggtgg tgggcgctga cgccttgtcc agatgggttg actgggagga tcggaactcg   720
tgtattctgt tcggagatgg cgcaggcgcg gtggtgctga cggtggcaga aggagatgcc   780
gattcgggtg tcttgggctt tgccatgcac agcgatggga caggtcaagg cgacttgaac   840
```

-continued

```
ctccagttcg cgaaggacga gtctcagagc cccccccgaga tcaatgccgt cacgccctac    900
aagggaaagt acaacaacat tgccatgaac ggaaaggaag tgtacaaatt tgccacgcgc    960
aaggtgccta ccgtcatcga agaggccttg gctaacgcgg gctgggggt agaggaggtt   1020 gactggttgt tgctgcatca ggccaacatt cgcatcatgg acgtagtggc cgaccggcta   1080
ggtctgtcga aggacaagat cctgactaac ctctccgact atggcaacac ctccgctggc   1140
tcaattcccc ttgctctcga cgaggccgtc aagtccggga aggtcaagaa aggcgacatc   1200
attgcgtgcg ctggattcgg agccggtcta tcgtggggca gcgctatcat tagatggcag   1260
ggctag                                                               1266
```

<210> SEQ ID NO 77
<211> LENGTH: 563
<212> TYPE: PRT
<213> ORGANISM: Cocos nucifera

<400> SEQUENCE: 77

```
Met Ala Gly Tyr Ser Val Ala Ala Pro Leu Cys Thr Trp Leu Val Ala
1               5                   10                  15

Ala Cys Val Thr Ala Ser Gly Gly Lys Glu Gly Ser Leu Val Ala Pro
            20                  25                  30

Ala Val Gly Glu Ala Arg Arg Leu Ser Arg Ser Ala Arg Arg Arg
        35                  40                  45

Ala Ala Ala Leu Arg Val Glu Ala Arg Asp Ser Ser Gly Gly Leu Met
    50                  55                  60

Ser Ala Leu Arg Gly Ser Gly Ile Gln Gly Leu Met Ser Ser Cys Leu
65                  70                  75                  80

Ala Phe Glu Pro Cys Ala Glu Phe Tyr Gly Ser Lys Gly Ala Ser Ala
                85                  90                  95

Phe Phe Gly Glu Ser Gly Phe Ser Leu Phe Gly Thr Trp Lys Ala Glu
            100                 105                 110

Thr Thr Arg Arg Gln Arg Arg Ala Ala Arg Ala Ser Cys Val Ser Gly
        115                 120                 125

Lys Ala Met Ala Ile Ala Val Gln Pro Ala Lys Glu Ile Ala Glu Lys
    130                 135                 140

Lys Arg Ile His Met Lys Lys Arg Arg Val Val Thr Gly Met Gly
145                 150                 155                 160

Val Val Thr Pro Leu Gly Asp Asp Pro Asp Ile Phe Tyr Asn Asn Leu
                165                 170                 175

Leu Asp Gly Val Ser Gly Ile Ser Gln Ile Glu Thr Phe Asp Cys Thr
            180                 185                 190

Asn Phe Pro Thr Arg Ile Ala Gly Glu Ile Lys Ser Phe Ser Thr Asp
        195                 200                 205

Gly Leu Val Ala Pro Lys Leu Ser Lys Arg Met Asp Lys Phe Met Leu
    210                 215                 220

Tyr Leu Leu Ile Ala Gly Lys Lys Ala Leu Ala Asn Gly Gly Val Thr
225                 230                 235                 240

Glu Glu Val Met Ser Gln Leu Asp Lys Ala Lys Cys Gly Val Leu Ile
                245                 250                 255

Gly Ser Ala Met Gly Gly Met Lys Val Phe Asn Asp Ala Ile Glu Ala
            260                 265                 270

Leu Arg Val Ser Tyr Lys Lys Met Asn Pro Phe Cys Val Pro Phe Ala
        275                 280                 285
```

```
Thr Thr Asn Met Gly Ser Ala Ile Leu Ala Met Asp Leu Gly Trp Met
290                 295                 300

Gly Pro Asn Tyr Ser Ile Ser Thr Ala Cys Ala Thr Ser Asn Phe Cys
305                 310                 315                 320

Ile Leu Asn Ala Ala His His Ile Ile Arg Gly Glu Ala Asp Ala Met
            325                 330                 335

Leu Cys Gly Gly Ser Asp Ala Thr Ile Ile Pro Ile Gly Leu Gly Gly
            340                 345                 350

Phe Val Ala Cys Arg Ala Leu Ser Gln Arg Asn Ser Asp Pro Thr Lys
            355                 360                 365

Ala Ser Arg Pro Trp Asp Ile Asp Arg Asp Gly Phe Val Met Gly Glu
370                 375                 380

Gly Ala Gly Val Leu Leu Leu Glu Glu Leu Glu His Ala Lys Gln Arg
385                 390                 395                 400

Gly Ala Asn Ile Tyr Ala Glu Phe Leu Gly Gly Ser Phe Thr Cys Asp
            405                 410                 415

Ala Tyr His Met Thr Glu Pro His Pro Glu Gly Ala Gly Ile Ala Leu
            420                 425                 430

Cys Ile Glu Asn Ala Leu Ala Gln Ala Gly Val Ala Lys Glu Asp Val
            435                 440                 445

Asn Tyr Val Asn Ala His Ala Thr Ser Thr Pro Ala Gly Asp Leu Lys
450                 455                 460

Glu Tyr Gln Ala Leu Ile Arg Cys Phe Gly Gln Asn Pro Glu Leu Arg
465                 470                 475                 480

Val Asn Ser Thr Lys Ser Met Ile Gly His Leu Leu Gly Ala Ala Gly
            485                 490                 495

Ala Val Glu Ala Val Ala Ser Ile Gln Ala Ile Arg Thr Gly Trp Val
            500                 505                 510

His Pro Asn Ile Asn Leu Glu Asn Pro Glu Lys Ser Val Asp Ile Asn
            515                 520                 525

Val Leu Val Gly Ser Arg Lys Glu Arg Leu Asp Val Lys Val Ala Leu
530                 535                 540

Ser Asn Ser Phe Gly Phe Gly Gly His Asn Ser Ser Ile Leu Phe Ala
545                 550                 555                 560

Pro Tyr Lys

<210> SEQ ID NO 78
<211> LENGTH: 1692
<212> TYPE: DNA
<213> ORGANISM: Cocos nucifera

<400> SEQUENCE: 78
atggccgggt actcggtggc ggcgccgctg tgcacttggt tggtggcggc gtgcgtcacg      60
gcgtcgggcg gaaaggaggg gtctttggtg gcgccggcgg tcggggaggc gaggcggttg     120
agccggtcgg cgaggaggcg gagggcggcg cgctacgag tcgaagcccg ggattcctct     180 ggggggactga tgtcggcgct ccgtggatcg gggatccagg ggctgatgag ctcctgcctc     240
gccttcgagc cctgcgcgga gttctacggc tctaagggcg cgtcggcgtt cttcggggag     300
agtggcttct ctctctttgg gacgtggaag gcggagacta caagaaggca gcgaagggcc     360
gcgcgcgcct cttgcgtctc aggcaaagca atggcaatag ctgtgcagcc tgctaaggaa     420
attgcagaaa agaagagaat ccatatgaag aagaggagag tggtcgtgac agggatgggt     480
gtggtgactc cactgggcga tgatcctgat atcttctaca ataaccttct tgatggtgtc     540
```

```
agtggtataa gtcaaattga acatttgac tgtacaaact ttccaacaag aattgcagga      600
gaaattaaat ctttctcaac agatggattg gtggcaccta aattatctaa acgaatggac    660
aaattcatgc tctatttact tattgctgga agaaagcat tagccaatgg tggggttact     720
gaagaggtca tgagtcagct tgacaaggca aaatgcggag tgctcatagg ctctgcaatg    780
ggtggaatga aggttttttaa tgatgccatc gaagctttaa gggtctcata taagaagatg   840
aatccatttt gtgttccatt tgcaacaaca acatgggtt ctgcaatcct tgctatggat     900
ctgggttgga tgggcccaaa ttactctatt tcaactgctt gtgctacaag caatttctgt    960
atcctgaatg cagcacacca tataataaga ggggaagctg atgcaatgct ttgtggtgga   1020
tcagatgcta caattatacc gattggattg gggggggtttg ttgcttgcag agcactttcg  1080
cagagaaata gtgatccgac taaagcatcg cggccttggg acattgatcg tgatggattt   1140
gtgatggggg aaggggctgg tgtgcttcta ctggaagaat tagagcatgc taagcaaaga   1200
ggagctaata tctatgctga atttcttgga ggaagcttca cgtgtgatgc ttaccacatg   1260
actgagccac atcctgaggg ggcaggcatt gctctttgca ttgagaatgc attagcacaa   1320
gctggggtag ccaaagaaga tgttaattat gtaaatgctc atgcaacttc aacacctgct   1380
ggtgatctaa aagagtatca agctcttatt cgttgttttg ggcagaatcc tgagctgaga   1440
gtgaactcta caaaatccat gattggtcac ctactaggag ctgctggtgc agtggaagct   1500
gttgcttcaa ttcaggcaat tcgaacaggg tgggtccatc ccaatatcaa tctcgaaaac   1560
ccagaaaaaa gtgtggatat aaatgtgctg gtgggctcga aaaggaaag gttggatgtg    1620
aaggtggcat tatcaaactc attcggtttt ggtggccaca actcgtctat cttgtttgcg   1680
ccttacaaat ag                                                       1692
```

<210> SEQ ID NO 79
<211> LENGTH: 534
<212> TYPE: PRT
<213> ORGANISM: Cuphea hookeriana

<400> SEQUENCE: 79

```
Met Ala Thr Ala Ser Cys Met Val Ala Ser Pro Phe Cys Thr Trp Leu
1               5                   10                  15

Val Ala Ala Cys Met Pro Thr Ser Ser Asp Asn Asp Pro Arg Ser Leu
            20                  25                  30

Ser His Lys Arg Leu Arg Leu Ser Arg Arg Arg Thr Leu Ser Ser
        35                  40                  45

His Cys Ser Leu Arg Gly Ser Thr Phe Gln Cys Leu Asp Pro Cys Asn
    50                  55                  60

Gln Gln Arg Phe Leu Gly Asp Asn Gly Phe Ala Ser Leu Phe Gly Ser
65                  70                  75                  80

Lys Pro Leu Arg Ser Asn Arg Gly His Leu Arg Leu Gly Arg Thr Ser
                85                  90                  95

His Ser Gly Glu Val Met Ala Val Ala Met Gln Pro Ala Gln Glu Val
            100                 105                 110

Ser Thr Asn Lys Lys Pro Ala Thr Lys Gln Arg Arg Val Val Val Thr
        115                 120                 125

Gly Met Gly Val Val Thr Pro Leu Gly His Asp Pro Asp Val Tyr Tyr
    130                 135                 140

Asn Asn Leu Leu Asp Gly Ile Ser Gly Ile Ser Glu Ile Glu Asn Phe
145                 150                 155                 160

Asp Cys Ser Gln Phe Pro Thr Arg Ile Ala Gly Glu Ile Lys Ser Phe
```

```
                165                 170                 175
Ser Thr Asp Gly Trp Val Ala Pro Lys Phe Ser Glu Arg Met Asp Lys
                180                 185                 190

Phe Met Leu Tyr Met Leu Thr Ala Gly Lys Lys Ala Leu Ala Asp Gly
                195                 200                 205

Gly Ile Thr Glu Asp Ala Met Lys Glu Leu Asn Lys Arg Lys Cys Gly
            210                 215                 220

Val Leu Ile Gly Ser Gly Leu Gly Met Lys Val Phe Ser Asp Ser
225                 230                 235                 240

Ile Glu Ala Leu Arg Thr Ser Tyr Lys Lys Ile Ser Pro Phe Cys Val
                245                 250                 255

Pro Phe Ser Thr Thr Asn Met Gly Ser Ala Ile Leu Ala Met Asp Leu
            260                 265                 270

Gly Trp Met Gly Pro Asn Tyr Ser Ile Ser Thr Ala Cys Ala Thr Ser
        275                 280                 285

Asn Phe Cys Ile Leu Asn Ala Ala Asn His Ile Ile Lys Gly Glu Ala
    290                 295                 300

Asp Met Met Leu Cys Gly Gly Ser Asp Ala Ala Val Leu Pro Val Gly
305                 310                 315                 320

Leu Gly Gly Phe Val Ala Cys Arg Ala Leu Ser Gln Arg Asn Asn Asp
                325                 330                 335

Pro Thr Lys Ala Ser Arg Pro Trp Asp Ser Asn Arg Asp Gly Phe Val
            340                 345                 350

Met Gly Glu Gly Ala Gly Val Leu Leu Leu Glu Glu Leu Glu His Ala
        355                 360                 365

Lys Lys Arg Gly Ala Thr Ile Tyr Ala Glu Phe Leu Gly Gly Ser Phe
    370                 375                 380

Thr Cys Asp Ala Tyr His Met Thr Glu Pro His Pro Glu Gly Ala Gly
385                 390                 395                 400

Val Ile Leu Cys Ile Glu Lys Ala Leu Ala Gln Ser Gly Val Ser Arg
                405                 410                 415

Glu Asp Val Asn Tyr Ile Asn Ala His Ala Thr Ser Thr Pro Ala Gly
            420                 425                 430

Asp Ile Lys Glu Tyr Gln Ala Leu Ala His Cys Phe Gly Gln Asn Ser
        435                 440                 445

Glu Leu Arg Val Asn Ser Thr Lys Ser Met Ile Gly His Leu Leu Gly
    450                 455                 460

Gly Ala Gly Gly Val Glu Ala Val Ala Val Gln Ala Ile Arg Thr
465                 470                 475                 480

Gly Trp Ile His Pro Asn Ile Asn Leu Glu Asp Pro Asp Glu Gly Val
                485                 490                 495

Asp Ala Lys Leu Leu Val Gly Pro Lys Lys Glu Lys Leu Lys Val Lys
            500                 505                 510

Val Gly Leu Ser Asn Ser Phe Gly Phe Gly Gly His Asn Ser Ser Ile
        515                 520                 525

Leu Phe Ala Pro Cys Asn
    530
```

<210> SEQ ID NO 80
<211> LENGTH: 1605
<212> TYPE: DNA
<213> ORGANISM: Cuphea hookeriana

<400> SEQUENCE: 80

-continued

| | |
|---|---|
| atggcgaccg cttcttgcat ggttgcgtcc cctttctgta cgtggctcgt agctgcatgc | 60 |
| atgcccactt catccgacaa cgacccacgt tcccttttccc acaagcggct ccgcctctcc | 120 |
| cgtcgccgga ggactctctc ctcccattgc tccctccgcg gatccacctt ccaatgcctc | 180 |
| gatccttgca accagcaacg cttcctcggg gataacggat tcgcttccct cttcggatcc | 240 |
| aagcctcttc gttcaaatcg cggccacctg aggctcggcc gcacttccca ttccggggag | 300 |
| gtcatggctg tggctatgca acctgcacag gaagtctcca caaataagaa acctgctacc | 360 |
| aagcaaaggc gagtagttgt gacaggtatg ggcgtggtga ctcctctagg ccatgacccc | 420 |
| gatgttact acaacaatct cctagacgga ataagtggca taagtgagat agagaacttc | 480 |
| gactgctctc agtttcccac gagaattgcc ggagagatca agtcttttc cacagatggc | 540 |
| tgggtggccc caaagttctc cgagaggatg gacaagttca tgctttacat gctgactgca | 600 |
| ggcaagaaag cattagcaga tggtggaatc actgaagatg cgatgaaaga gctcaataaa | 660 |
| agaaagtgtg gagttctcat tggctccgga ttgggcggta tgaaggtatt cagcgattcc | 720 |
| attgaagctc tgaggacttc atataagaag atcagtccct tttgtgtacc ttttctacc | 780 |
| acaaatatgg gatccgctat tcttgcaatg gacttgggat ggatgggccc taactattcg | 840 |
| atatcaactg cctgtgcaac aagtaacttc tgtatactga atgctgcgaa ccacataatc | 900 |
| aaaggcgaag cagacatgat gctttgtggt ggctcggatg cggccgtttt acctgttggt | 960 |
| ttgggaggtt tcgtagcatg ccgagctttg tcacagagga taatgaccc taccaaagct | 1020 |
| tcgagaccat gggacagtaa tcgtgatgga tttgtgatgg gagaaggagc tggagtttta | 1080 |
| cttcttgagg agttagagca tgcaaagaaa agaggtgcaa ccatttatgc ggaatttcta | 1140 |
| ggtgggagtt tcacttgcga cgcctaccac atgaccgagc ctcaccctga aggagctggt | 1200 |
| gtgatcctct gcatagagaa ggccttggct cagtccggag tctcgaggga agacgtaaat | 1260 |
| tacataaatg cgcatgcaac ttccactcct gctggagata tcaaggaata ccaagctctc | 1320 |
| gcccactgtt tcggccaaaa cagtgagctg agagtgaatt ccaccaaatc gatgatcggt | 1380 |
| caccttcttg gaggagctgg tggcgtagaa gcagttgcag tagttcaggc aataaggaca | 1440 |
| ggatggatcc atccaaatat taatttggaa gacccggacg aaggcgtgga tgcaaaactg | 1500 |
| ctcgtcggcc ctaagaagga gaaactgaag gtcaaggtcg gtttgtccaa ttcatttggg | 1560 |
| ttcggcggcc ataactcatc catactattt gccccctgca actag | 1605 |

<210> SEQ ID NO 81
<211> LENGTH: 538
<212> TYPE: PRT
<213> ORGANISM: Cuphea lanceolata

<400> SEQUENCE: 81

Met Ala Ala Ser Ser Met Ala Ala Ser Pro Phe Cys Thr Trp Leu
1               5                   10                  15

Val Ala Ala Cys Met Ser Thr Ser Phe Glu Asn Asn Pro Arg Ser Pro
            20                  25                  30

Ser Ile Lys Arg Leu Pro Arg Arg Arg Val Leu Ser His Cys Ser
        35                  40                  45

Leu Arg Gly Ser Thr Phe Gln Cys Leu Val Thr Ser His Ile Asp Pro
    50                  55                  60

Cys Asn Gln Asn Cys Ser Ser Asp Ser Leu Ser Phe Ile Gly Val Asn
65                  70                  75                  80

Gly Phe Gly Ser Lys Pro Phe Ser Asn Arg Gly His Arg Arg Leu
            85                  90                  95

```
Gly Arg Ala Ser His Ser Gly Glu Ala Met Ala Val Ala Leu Gln Pro
            100                 105                 110

Ala Gln Glu Val Ala Thr Lys Lys Pro Ala Ile Lys Gln Arg Arg
        115                 120                 125

Val Val Val Thr Gly Met Gly Val Val Thr Pro Leu Gly His Glu Pro
130                 135                 140

Asp Val Phe Tyr Asn Asn Leu Leu Asp Gly Val Ser Gly Ile Ser Glu
145                 150                 155                 160

Ile Glu Asn Phe Asp Ser Thr Gln Phe Pro Thr Arg Ile Ala Gly Glu
                165                 170                 175

Ile Lys Ser Phe Ser Thr Asp Gly Trp Val Ala Pro Lys Leu Ser Lys
            180                 185                 190

Arg Met Asp Lys Leu Met Leu Tyr Leu Leu Thr Ala Gly Lys Lys Ala
        195                 200                 205

Leu Ala Asp Ala Gly Ile Thr Asp Asp Val Met Lys Glu Leu Asp Lys
    210                 215                 220

Arg Lys Cys Gly Val Leu Ile Gly Ser Gly Met Gly Gly Met Lys Leu
225                 230                 235                 240

Phe Tyr Asp Ala Leu Glu Ala Leu Lys Ile Ser Tyr Arg Lys Met Asn
                245                 250                 255

Pro Phe Cys Val Pro Phe Ala Thr Thr Asn Met Gly Ser Ala Met Leu
            260                 265                 270

Ala Met Asp Leu Gly Trp Met Gly Pro Asn Tyr Ser Ile Ser Thr Ala
        275                 280                 285

Cys Ala Thr Ser Asn Phe Cys Ile Leu Asn Ala Ala Asn His Ile Ile
    290                 295                 300

Arg Gly Glu Ala Asp Met Met Leu Cys Gly Gly Ser Asp Ala Val Ile
305                 310                 315                 320

Ile Pro Ile Gly Leu Gly Gly Phe Val Ala Cys Arg Ala Leu Ser Gln
                325                 330                 335

Arg Asn Asn Asp Pro Thr Lys Ala Ser Arg Pro Trp Asp Ser Asn Arg
            340                 345                 350

Asp Gly Phe Val Met Gly Glu Gly Ala Gly Val Leu Leu Leu Glu Glu
        355                 360                 365

Leu Glu His Ala Lys Lys Arg Gly Ala Thr Ile Tyr Ala Glu Phe Leu
    370                 375                 380

Gly Gly Ser Phe Thr Cys Asp Ala Tyr His Met Thr Glu Pro His Pro
385                 390                 395                 400

Glu Gly Ala Gly Val Ile Leu Cys Ile Glu Lys Ala Met Ala Gln Ala
                405                 410                 415

Gly Val Ser Arg Glu Asp Val Asn Tyr Ile Asn Ala His Ala Thr Ser
            420                 425                 430

Thr Pro Ala Gly Asp Ile Lys Glu Tyr Gln Ala Leu Ala His Cys Phe
        435                 440                 445

Gly Gln Asn Ser Glu Leu Arg Val Asn Ser Thr Lys Ser Met Ile Gly
    450                 455                 460

His Leu Leu Gly Ala Ala Gly Gly Val Glu Ala Val Thr Val Ile Gln
465                 470                 475                 480

Ala Ile Arg Thr Gly Trp Ile His Pro Asn Leu Asn Leu Glu Asp Pro
                485                 490                 495

Asp Lys Ala Val Asp Ala Lys Phe Leu Val Gly Pro Glu Lys Glu Arg
            500                 505                 510
```

Leu Asn Val Lys Val Gly Leu Ser Asn Ser Phe Gly Phe Gly Gly His
    515                 520                 525

Asn Ser Ser Ile Leu Phe Ala Pro Tyr Asn
    530                 535

<210> SEQ ID NO 82
<211> LENGTH: 1617
<212> TYPE: DNA
<213> ORGANISM: Cuphea lanceolata

<400> SEQUENCE: 82

| | | | | | |
|---|---|---|---|---|---|
| atggcggcgg | cctcttccat | ggctgcgtca | ccgttctgta | cgtggctcgt | agctgcttgc | 60 |
| atgtccactt | ccttcgaaaa | caacccacgt | tcgccctcca | tcaagcgtct | ccccgccgg | 120 |
| aggagggttc | tctcccattg | ctccctccgt | ggatccacct | tccaatgcct | cgtcacctca | 180 |
| cacatcgacc | cttgcaatca | gaactgctcc | tccgactccc | ttagcttcat | cggggttaac | 240 |
| ggattcggat | ccaagccatt | ccggtccaat | cgcggccacc | ggaggctcgg | ccgtgcttcc | 300 |
| cattccgggg | aggccatggc | tgtggctctg | caacctgcac | aggaagtcgc | cacgaagaag | 360 |
| aaacctgcta | tcaagcaaag | gcgagtagtt | gttacaggaa | tgggtgtggt | gactcctcta | 420 |
| ggccatgaac | ctgatgtttt | ctacaacaat | ctcctagatg | gagtaagcgg | cataagtgag | 480 |
| atagagaact | tcgacagcac | tcagtttccc | acgagaattg | ccggagagat | caagtctttt | 540 |
| tccacagatg | gctgggtggc | cccaaagctc | tccaagagga | tggacaagct | catgctttac | 600 |
| ttgttgactg | ctggcaagaa | agcattagca | gatgctggaa | tcaccgatga | tgtgatgaaa | 660 |
| gagcttgata | aagaaagtg | tggagttctc | attggctccg | gaatgggcgg | catgaagttg | 720 |
| ttctacgatg | cgcttgaagc | cctgaaaatc | tcttacagga | agatgaaccc | ttttgtgta | 780 |
| ccttttgcca | ccacaaatat | gggatcagct | atgcttgcaa | tggatctggg | atggatgggt | 840 |
| ccaaactact | ctatttcaac | tgcctgtgca | acaagtaatt | tctgtatact | gaatgctgca | 900 |
| aaccacataa | tcagaggcga | agctgacatg | atgctttgtg | gtggctcgga | tgcggtcatt | 960 |
| atacctatcg | gtttgggagg | ttttgtggcg | tgccgagctt | tgtcacagag | gaataatgac | 1020 |
| cctaccaaag | cttcgagacc | atgggatagt | aatcgtgatg | gatttgtaat | gggcgaagga | 1080 |
| gctggagtgt | tacttctcga | ggagttagag | catgcaaaga | aagaggtgc | aaccatttat | 1140 |
| gcagaattt | taggggggcag | tttcacttgc | gatgcctacc | acatgaccga | gcctcaccct | 1200 |
| gaaggagctg | gagtgatcct | ctgcatagag | aaggccatgg | ctcaggccgg | agtctctaga | 1260 |
| gaagatgtaa | attacataaa | tgcccatgca | acttccactc | ctgctggaga | tatcaaagaa | 1320 |
| taccaagctc | tcgcccactg | tttcggccaa | acagcgagc | tgagagtgaa | ttccactaaa | 1380 |
| tcgatgatcg | gtcatcttct | tggagcagct | ggtggcgtag | aagcagttac | tgtaattcag | 1440 |
| gcgataagga | ctgggtggat | ccatccaaat | cttaatttgg | aagacccgga | caaagccgtg | 1500 |
| gatgcaaaat | ttctcgtggg | acctgagaag | gagagactga | atgtcaaggt | cggtttgtcc | 1560 |
| aattcatttg | ggttcggtgg | gcataactcg | tctatactct | tcgcccctta | caattag | 1617 |